US009110305B2

(12) United States Patent
Yamada et al.

(10) Patent No.: US 9,110,305 B2
(45) Date of Patent: Aug. 18, 2015

(54) MICROSCOPE CELL STAINING OBSERVATION SYSTEM, METHOD, AND COMPUTER PROGRAM PRODUCT

(75) Inventors: Tatsuki Yamada, Tokyo (JP); Yuichi Ishikawa, Tokyo (JP); Kengo Takeuchi, Tokyo (JP)

(73) Assignees: OLYMPUS CORPORATION, Tokyo (JP); JAPANESE FOUNDATION FOX CANCER RESEARCH, Tokyo (JP)

( * ) Notice: Subject to any disclaimer, the term of this patent is extended or adjusted under 35 U.S.C. 154(b) by 922 days.

(21) Appl. No.: 12/950,268

(22) Filed: Nov. 19, 2010

(65) Prior Publication Data
US 2011/0212486 A1 Sep. 1, 2011

(30) Foreign Application Priority Data
Feb. 26, 2010 (JP) .................................. 2010-043441

(51) Int. Cl.
*H04N 7/18* (2006.01)
*G02B 21/36* (2006.01)
*G01N 1/30* (2006.01)

(52) U.S. Cl.
CPC ................ *G02B 21/365* (2013.01); *G01N 1/30* (2013.01)

(58) Field of Classification Search
CPC .................................. G02B 21/365; G01N 1/30
USPC ............ 348/79, 302; 356/338; 382/128, 133, 382/162; 435/29, 40.5
See application file for complete search history.

(56) References Cited

U.S. PATENT DOCUMENTS

| 8,111,897 B2 | 2/2012 | Yamashita et al. |
| 2001/0046689 A1* | 11/2001 | Yahiro ............................ 435/29 |
| 2001/0049114 A1 | 12/2001 | Bacus |
| 2003/0081209 A1* | 5/2003 | Takahashi et al. ............ 356/338 |
| 2003/0138140 A1* | 7/2003 | Marcelpoil et al. ........... 382/162 |
| 2004/0023320 A1* | 2/2004 | Steiner et al. ................ 435/40.5 |

(Continued)

FOREIGN PATENT DOCUMENTS

| JP | H07-120324 A | 5/1995 |
| JP | H09-281405 A | 10/1997 |

(Continued)

OTHER PUBLICATIONS

The Decision of a Patent Grant, issued on Feb. 18, 2014, in the corresponding Japanese application No. 2010-043441 and English translation thereof.

*Primary Examiner* — Young Lee
*Assistant Examiner* — Richard Carter

(57) ABSTRACT

A microscope system includes an acquisition unit that obtains a specimen image acquired by capturing the specimen stained by an element identification dye that visualizes a predetermined cell constituent element and a molecule target dye that visualizes a predetermined target molecule by using a microscope; a dye amount unit that obtains dye amounts of the element identification dye and the molecule target dye that stain corresponding positions on the specimen for each pixel of the image; an element area identification unit that identifies an area of the cell constituent element based on the dye amount of the element identification dye; a condition setting unit that sets the presence or absence of the predetermined target molecule on the cell constituent element as a condition; and an extraction unit that extracts an area of a target portion that satisfies the condition based on the dye amount of the molecule target dye.

10 Claims, 30 Drawing Sheets

(56) References Cited

U.S. PATENT DOCUMENTS

2005/0031183 A1* 2/2005 Wrigglesworth et al. .... 382/133
2008/0267469 A1* 10/2008 Kawabata et al. ............ 382/128
2008/0279441 A1* 11/2008 Matsuo et al. ................ 382/133
2009/0295963 A1* 12/2009 Bamford et al. .............. 348/302

FOREIGN PATENT DOCUMENTS

| JP | 2002-521682 A | 7/2002 |
| JP | 2006-343573 A | 12/2006 |
| JP | 2008-051654 A | 6/2008 |
| JP | 2009-175334 A | 6/2009 |

* cited by examiner

| ALIGNMENT NUMBER | | | POSITION OF ELECTRICALLY DRIVEN STAGE | | |
|---|---|---|---|---|---|
| x | y | z | X | Y | Z |
| 1 | 1 | – | $X_{11}$ | $Y_{11}$ | $Z_{11}$ |
| 1 | 2 | – | $X_{12}$ | $Y_{12}$ | $Z_{12}$ |
| ⋮ | ⋮ | ⋮ | ⋮ | ⋮ | ⋮ |

| LABEL | CIRCUMSCRIBED RECTANGLE | | | | CENTER OF GRAVITY | | AREA | BOUND-ARY LENGTH | DEGREE OF CIRCU-LARITY | LONG AXIS | SHORT AXIS | ASPECT RATIO |
|---|---|---|---|---|---|---|---|---|---|---|---|---|
| | x | y | W | H | x | y | | | | | | |
| | | | | | | | | | | | | |
| | | | | | | | | | | | | |
| | | | | | | | | | | | | |
| | | | | | | | | | | | | |
| | | | | | | | | | | | | |

FIG.23

| LABEL | CIRCUMSCRIBED RECTANGLE | | | | CENTER OF GRAVITY | | THICK-NESS | BOUND-ARY LENGTH | DEGREE OF CIRCU-LARITY | LONG AXIS | SHORT AXIS | ASPECT RATIO | PRESENCE OR ABSENCE OF NUCLEUS (THE NUMBER OF NUCLEI) |
|---|---|---|---|---|---|---|---|---|---|---|---|---|---|
| | x | y | W | H | x | y | | | | | | | |
| | | | | | | | | | | | | | |
| | | | | | | | | | | | | | |
| | | | | | | | | | | | | | |
| | | | | | | | | | | | | | |
| | | | | | | | | | | | | | |

(a) TARGET PORTION MAP OF CELL MEMBRANE (b) TARGET PORTION MAP OF CYTOPLASM (c) TARGET PORTION MAP

FIG.39

| ABNORMAL LEVEL IDENTIFICATION ITEM | | | | DETERMINATION RESULT | |
|---|---|---|---|---|---|
| N/C RATIO | AVERAGE DYE AMOUNT OF NUCLEUS | AREA OF NUCLEUS | DEGREE OF CIRCULARITY | CLASSI-FICATION | SCORE |
| 1 | 1 | 1 | 1 | NORMAL | 0 |
| 1 | 1 | 1 | 2 | NORMAL | 0 |
| 1 | 1 | 1 | 3 | NORMAL | 0 |
| 1 | 1 | 1 | 4 | NORMAL | 0 |
| ⋮ | ⋮ | ⋮ | ⋮ | ⋮ | ⋮ |
| 4 | 4 | 4 | 3 | ABNORMAL | 10 |
| 4 | 4 | 4 | 4 | ABNORMAL | 10 |

FIG.40

| ABNORMAL LEVEL IDENTIFICATION ITEM | | | | DETERMINATION RESULT | |
|---|---|---|---|---|---|
| N/C RATIO | AVERAGE DYE AMOUNT OF NUCLEUS | AREA OF NUCLEUS | DEGREE OF CIRCULARITY | CLASSIFI-CATION | SCORE |
| 1 | 1 | 1 | 1 | NORMAL | 0 |
| 1 | 1 | 1 | 2 | NORMAL | 0 |
| 1 | 1 | 1 | 3 | NORMAL | 0 |
| 1 | 1 | 1 | 4 | NORMAL | 0 |
| ⋮ | ⋮ | ⋮ | ⋮ | ⋮ | ⋮ |
| 4 | 4 | 4 | 3 | ABNORMAL | 10 |
| 4 | 4 | 4 | 4 | ABNORMAL | 10 |

FIG.41A

| LABEL | | | | CIRCUMSCRIBED RECTANGLE | | | | CENTER OF GRAVITY | | AREA | BOUND-ARY LENGTH | DE-GREE OF CIRCU-LARITY | LONG AXIS | SHORT AXIS | AS-PECT RATIO |
|---|---|---|---|---|---|---|---|---|---|---|---|---|---|---|---|
| CELL/ CELL CLUMP | CELL NU-CLEUS | CELL MEM-BRANE | CYTO-PLASM | x | y | W | H | x | y | | | | | | |
| | | | | | | | | | | | | | | | |
| | | | | | | | | | | | | | | | |
| | | | | | | | | | | | | | | | |
| | | | | | | | | | | | | | | | |
| | | | | | | | | | | | | | | | |

FIG.41B

| LABEL | | | | THE NUMBER OF NUCLEI | AREA OF NU-CLEUS | AVERAGE DYE AMOUNT OF NUCLEUS | DISPER-SION OF AREAS OF NUCLEI | N/C RATIO | AV-ERAGE DYE AMOUNT OF CYTO-PLASM | DETERMINATION | |
|---|---|---|---|---|---|---|---|---|---|---|---|
| CELL/ CELL CLUMP | CELL NU-CLEUS | CELL MEM-BRANE | CYTO-PLASM | | | | | | | CLASSIFI-CATION (NORMAL/ ABNORMAL) | SCORE |
| | | | | | | | | | | | |
| | | | | | | | | | | | |
| | | | | | | | | | | | |
| | | | | | | | | | | | |
| | | | | | | | | | | | |

MICROSCOPE CELL STAINING OBSERVATION SYSTEM, METHOD, AND COMPUTER PROGRAM PRODUCT

CROSS-REFERENCE TO RELATED APPLICATIONS

This application is based upon and claims the benefit of priority from Japanese Patent Application No. 2010-043441, filed on Feb. 26, 2010, the entire contents of which are incorporated herein by reference.

BACKGROUND OF THE INVENTION

1. Field of the Invention

The present invention relates to a microscope system, a specimen observation method, and a computer program product for acquiring a specimen image obtained by capturing the image of the specimen using a microscope and observing the specimen by displaying the acquired specimen image.

2. Description of the Related Art

For example, in a pathological diagnosis, it is widely performed that a tissue sample obtained by organ harvesting or needle biopsy is thinly sliced to a thickness of several microns to create a specimen, and the specimen is magnified and observed by using an optical microscope to obtain various findings. Here, the specimen hardly absorbs or scatters light and is nearly clear and colorless, so that it is generally stained by dye before the observation.

Various types of staining methods are proposed. In particular, for a tissue specimen, as morphological observation staining for observing morphology of the specimen, hematoxylin-eosin staining (hereinafter referred to as "HE staining") that uses two types of dyes, hematoxylin and eosin, is normally used. For example, a method is disclosed in which an image of an HE-stained specimen is captured by multiband imaging, an amount of dye that stains the specimen is calculated (estimated) by estimating a spectrum at a specimen position, and an RGB image to be displayed is synthesized (for example, refer to Japanese Laid-open Patent Publication No. 2008-51654, Japanese Laid-open Patent Publication No. 07-120324, Japanese National Publication of International Patent Application No. 2002-521682, or the like). As another morphological observation staining, for example, in cytological diagnosis, Papanicolaou staining (Pap staining) is known.

In a pathological diagnosis, molecule target staining to check an expression of molecule information is performed on a specimen to be used for diagnosis of function abnormality, such as expression abnormality of a gene or a protein. For example, the specimen is fluorescently labeled using an IHC (immunohistochemistry) method, an ICC (immunocytochemistry) method, and an ISH (in situ hybridization) method and fluorescently observed, or is enzyme-labeled and observed in a bright field. In this case, in the fluorescent observation of the specimen by the fluorescent labeling, for example, a confocal laser microscope is used. In this observation by the fluorescent labeling, a highly-sensitive and sharp image can be acquired, and the specimen can be three-dimensionally observed or the specimen can be observed from a desired direction. Also, there is an advantage that a plurality of target molecules can be labeled at the same time. However, there is a problem that the observation by the fluorescent labeling cannot be performed easily because the specimen cannot be preserved for a long period of time, the diagnosis takes a long time, and a dedicated dark room is required. In addition, there is also a problem that the observation by the fluorescent labeling is difficult to be performed at the same time as the morphological observation of the specimen, so that the observation by the fluorescent labeling is not so practical in the pathological diagnosis.

Meanwhile, in the bright field observation by the enzyme-labeling (the IHC method, the ICC method, and the CISH method), the specimen can be semi-permanently preserved. Since an optical microscope is used, the observation can be performed together with the morphological observation, and is used as the standard in the pathological diagnosis.

On the other hand, in recent years, as a medical treatment for cancer or the like, a medical treatment called molecular target treatment that uses a therapeutic drug (antibody therapeutic drug) acting on a specific molecular target is performed, and therapeutic effects and side-effect-reducing effects are expected. For example, in the cancer treatment by the molecular target treatment, an antibody therapeutic drug targeting molecules (antigenic proteins) specific to cancer cells is used. Drugs that are allowed to be used as the antibody therapeutic drug include, for example, Trastuzumab (Herceptin (registered trademark)) that is an anti-HER2 antibody drug against breast cancer, and Cetuximab (Erbitax (registered trademark)) that is an anti-EGFR antibody drug against large intestine cancer.

In diagnosis of cancer, for example, whether or not an antigen (target molecule) that is a target molecule of the antibody therapeutic drug is expressed on the surface of a cell or a cell membrane is observed by the IHC method or the like, and suitable patients are selected.

Or, antibodies against a plurality of antigens are applied to label each antigen, and the combination of presences and absences of the expressions of the antigens is evaluated (antigen panel evaluation). For example, a cancer stem cell is identified by evaluating a combination of antigens expressed on a cell membrane. As a specific example, in diagnosis of breast cancer, a cell in which CD44 molecule is expressed on the cell membrane and CD24 molecule is not expressed (or expression rate of the CD24 molecule is low) on the cell membrane is identified as the cancer stem cell. On the other hand, in diagnosis of large intestine cancer, a cell in which CD44 molecule and CD133 molecule are expressed on the cell membrane is identified as the cancer stem cell. Further, various antibody panel evaluations such as estimation of a primary site of a cancer of unknown primary site (for example, differentiation of large intestine cancer, breast cancer, and lung epithelial cancer), differentiation of B-cell lymphoma and T-cell lymphoma, identification of mesothelioma, and differentiation of squamous cell cancer and adenocarcinoma are performed by applying antibodies for an intended purpose to label antigens.

SUMMARY OF THE INVENTION

A microscope system according to an aspect of the present invention includes an image acquisition unit that obtains a specimen image acquired by capturing an image of the specimen stained by an element identification dye that visualizes a predetermined cell constituent element and a molecule target dye that visualizes a predetermined target molecule by using a microscope; a dye amount obtaining unit that obtains dye amounts of the element identification dye and the molecule target dye that stain corresponding positions on the specimen for each pixel of the specimen image; an element area identification unit that identifies an area of the predetermined cell constituent element in the specimen image on the basis of the dye amount of the element identification dye; an extraction condition setting unit that sets the presence or absence of the predetermined target molecule at least on the predetermined cell constituent element as an extraction condition; a target portion extraction unit that extracts an area of a target portion that satisfies the extraction condition on the basis of the dye amount of the molecule target dye obtained with respect to pixels in the area of the predetermined cell constituent element; a display image generator that generates a display image representing the area of the target portion; and a display processing unit that performs processing for displaying the display image on a display unit.

A specimen observation method according to another aspect of the present invention includes obtaining a specimen image acquired by capturing an image of the specimen stained by an element identification dye that visualizes a predetermined cell constituent element and a molecule target dye that visualizes a predetermined target molecule by using a microscope; obtaining dye amounts of the element identification dye and the molecule target dye that stain corresponding positions on the specimen for each pixel of the specimen image; identifying an area of the predetermined cell constituent element in the specimen image on the basis of the dye amount of the element identification dye; setting the presence or absence of the predetermined target molecule at least on the predetermined cell constituent element as an extraction condition; extracting an area of a target portion that satisfies the extraction condition on the basis of the dye amount of the molecule target dye obtained with respect to pixels in the area of the predetermined cell constituent element; generating a display image representing the area of the target portion; and displaying the display image.

A computer program product according to still another aspect of the present invention has a computer readable medium including programmed instructions. The instructions, when executed by a computer, cause the computer to perform obtaining a specimen image acquired by capturing an image of the specimen stained by an element identification dye that visualizes a predetermined cell constituent element and a molecule target dye that visualizes a predetermined target molecule by using an operation instruction to a microscope; obtaining dye amounts of the element identification dye and the molecule target dye that stain corresponding positions on the specimen for each pixel of the specimen image; identifying an area of the predetermined cell constituent element in the specimen image on the basis of the dye amount of the element identification dye; setting the presence or absence of the predetermined target molecule at least on the predetermined cell constituent element as an extraction condition; extracting an area of a target portion that satisfies the extraction condition on the basis of the dye amount of the molecule target dye obtained with respect to pixels in the area of the predetermined cell constituent element; generating a display image representing the area of the target portion; and displaying the display image.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 20 is a schematic diagram for explaining a data configuration example of map data of a cell nucleus;

FIG. 21 is a schematic diagram for explaining a data configuration example of map data of a cell membrane;

FIG. 22 is a diagram for explaining a data configuration example of morphological characteristic data of a cell nucleus;

FIG. 23 is a diagram for explaining a data configuration example of morphological characteristic data of a cell membrane;

FIG. 39 is a diagram showing an example of a score determination table applied to a cell area;

FIG. 40 is a diagram showing an example of a score determination table applied to a cell clump area;

FIG. 41A is a diagram for explaining a data configuration example of a cell list table;

FIG. 41B is a diagram for explaining another data configuration example of the cell list table.

DETAILED DESCRIPTION OF THE PREFERRED EMBODIMENTS

Figure 1:
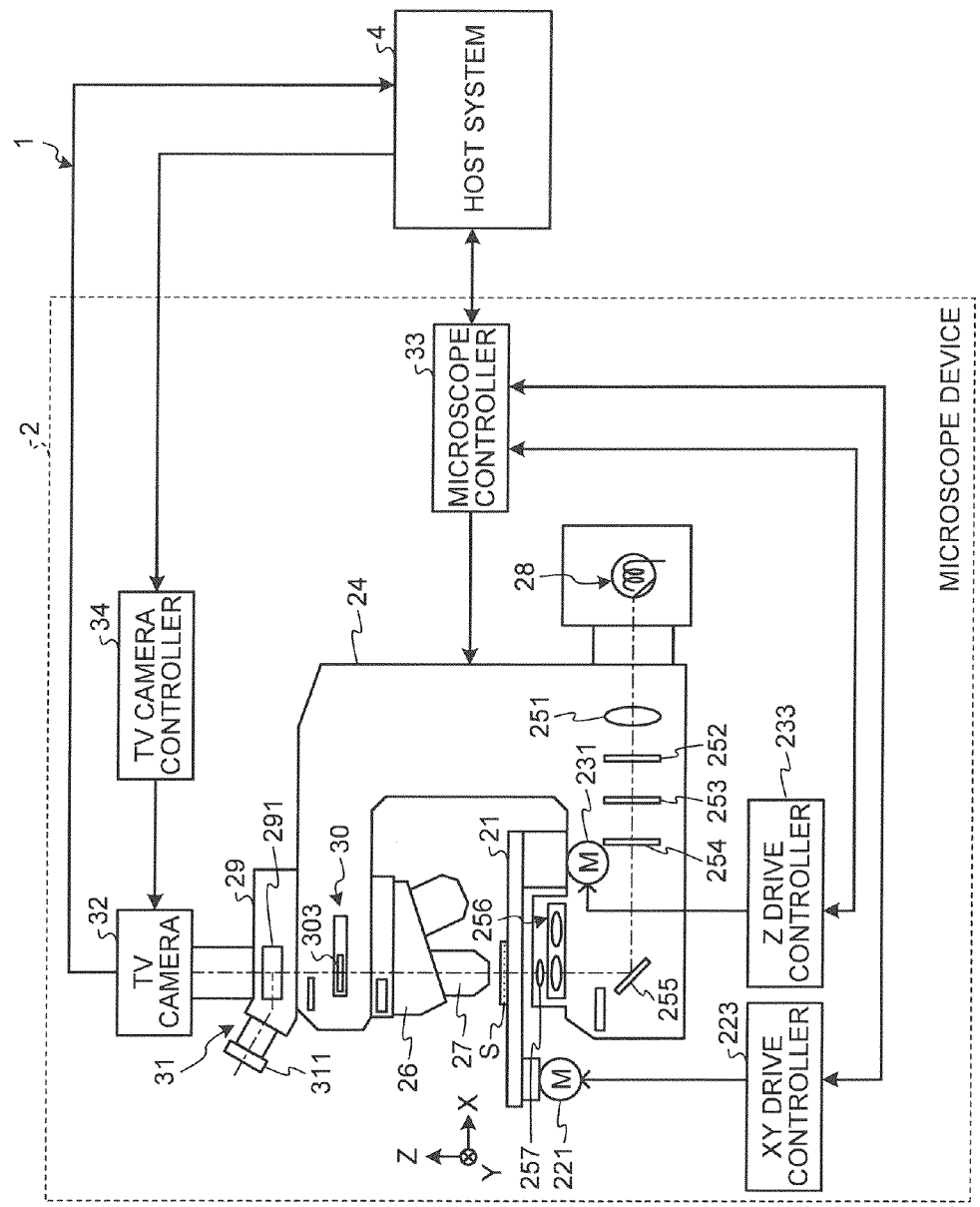
FIG. 1 is a schematic diagram for explaining an entire configuration example of a microscope system according to a first embodiment.

Hereinafter, preferred embodiments of the present invention will be described in detail with reference to the drawings. The present invention is not limited to the embodiments. In the drawings, the same reference numerals are given to the same components.

When observing a specimen by using a microscope, an area (visual field) that can be observed at a time is determined by a magnification of an objective lens. Here, the higher the magnification of the objective lens is, the higher the resolution of an image that can be obtained, but the smaller the visual field is. To solve this type of problem, conventionally, an operation is performed in which an image with high resolution and large visual field is generated by capturing partial images of a specimen for each portion of the specimen by using a high resolution objective lens while moving a visual field by moving an electrically driven stage or the like on which the specimen is mounted, and combining the captured partial images (for example, refer to Japanese Laid-open Patent Publication No. 09-281405 and Japanese Unexamined Patent Application Publication No. 2006-343573), and a system performing the above operation is called a virtual microscope system. Hereinafter, the image with high resolution and large visual field generated by the virtual microscope system is referred to as "VS image".

According to the virtual microscope system, an observation can be performed even when there is no actual specimen. If the generated VS image is opened so that the VS image can be viewed via a network, the specimen can be observed regardless of time and place. Therefore, the virtual microscope system is used in a field of pathological diagnosis education or a consultation between pathologists distant from each other. Hereinafter, a case in which the present invention is applied to the virtual microscope system will be described as an example.

In a first embodiment, the presence or absence of a target molecule located (expressed) on a predetermined cell component is set as an extraction condition, and a portion in a specimen that matches the extraction condition is extracted as a target portion. Here, the cell component is a collective name of cell nucleus, cell membrane, cytoplasm, and the like that are cell constituent elements constituting a cell.

First, a specimen to be observed and diagnosed (hereinafter referred to as "target specimen") will be described. The target specimen is a multistained specimen that is multistained with a plurality of dyes. More specifically, the target specimen is a specimen on which the morphological observation staining for observing the morphology of the specimen and the molecule target staining for checking an expression of molecule information are performed, and includes a specimen used for a tissue diagnosis and a specimen used for a cytological diagnosis. In the cytological diagnosis, a specimen (cell block) may be made by a cell block method to observe a structure inside a cell, such as, for example, three-dimensional structure of a cell clump. The specimen used for the cytological diagnosis includes the cell block.

The morphological observation staining stains cell nucleus, cytoplasm, connective tissue, and the like to visualize them. According to the morphological observation staining, it is possible to grasp the size of elements constituting a tissue, the positional relationship between them, and the like, so that the state of the specimen can be determined morphologically. Here, the morphological observation staining includes the HE staining and Pap staining described above, special staining such as hematoxylin staining (E staining), Giemsa staining, and Elastica van Gieson staining, and trichrome staining that performs HE staining along with Victoria blue staining that specifically stains an elastic fiber. The Pap staining and the Giemsa staining are staining methods targeting a specimen used for a cytological diagnosis.

On the other hand, the IHC method and the ICC method in the molecule target staining are methods in which a specific antibody against a material (mainly proteins) whose localization is desired to be checked is applied to a tissue and linked to the material, and thus the state is visualized. For example, an enzyme antibody method for visualizing localization of an antibody linked to an antigen by coloring of enzyme reaction is known. As the enzyme, for example, peroxidase and alkaline phosphatase are generally used.

In the description below, the dye that stains a specimen includes a color component visualized by staining, and a color component visualized by, for example, coloring of enzyme reaction or the like. Hereinafter, a dye visualized by the morphological observation staining is called "morphological observation dye", a dye visualized by the molecule target staining is called "molecule target dye", and a dye that actually stains a target specimen is called "staining dye".

In the first embodiment, at least either one of the morphological observation staining and the molecule target staining, which are staining dyes staining the target specimen as described above, corresponds to cell component identification staining for identifying a cell component. The cell component identification staining specifically stains cell nucleus, cell membrane, or cytoplasm that are a cell component. Hereinafter, a staining dye that is visualized by the cell component identification staining for identifying cell nucleus is accordingly referred to as "cell nucleus identification dye". A staining dye that is visualized by the cell component identification staining for identifying cell membrane is accordingly referred to as "cell membrane identification dye". A staining dye that is visualized by the cell component identification staining for identifying cytoplasm is accordingly referred to as "cytoplasm identification dye". The cell nucleus identification dye, the cell membrane identification dye, and the cytoplasm identification dye are collectively referred to as "cell component identification dye". The cell component identification dye corresponds to an element identification dye.

More specifically, the target specimen exemplified as a specimen to be observed and diagnosed in the first embodiment is a tissue specimen on which the HE staining using two dyes of hematoxylin (hereinafter referred to as "H dye") and eosin (hereinafter referred to as "E dye") as the morphological observation staining is performed. In addition, the target specimen is a specimen obtained by labeling the tissue specimen by coloring of DAB reaction (hereinafter referred to as "DAB dye") using an EGFR antibody that recognizes an EGFR receptor as the molecule target staining. Further, the target specimen is a specimen obtained by labeling the tissue specimen by coloring of New Fuchsin (hereinafter referred to as "NF dye") using an ESA antibody that recognizes an epithelial-specific antigen ESA (Epithelial Specific Antigen) that is a kind of glycoprotein expressed (located) on cell membrane of epithelial cells. In summary, there are four types of dyes, H dye, E dye, DAB dye, and NF dye which are the staining dyes of the target specimen to be observed and diagnosed in the first embodiment. The target specimen is a specimen in which the cell nucleus is stained blue-purple by H dye, the cytoplasm and the connective tissue are stained pink by E dye, the EGFR receptor is labeled brownish-red by DAB dye, and the cell membrane of epithelial cells is labeled red by NF dye. In the first embodiment, as an example, a case is described in which, among the four dyes, the H dye is used as the cell nucleus identification dye and the NF dye is used as the cell membrane identification dye, and a portion where the EGFR receptor is expressed on the cell membrane in the target specimen is extracted as the target portion.

The identification of cell membrane is not limited to the case in which the ESA antibody that recognizes the epithelial-specific antigen ESA that is a kind of glycoprotein on cell membrane of epithelial cells is used and labeling with the NF dye is performed. For example, an E Cadherin antibody that is an adhesion molecule expressed on cell membrane of epithelial cells may be used, or both the ESA antibody and the E Cadherin antibody may be used. And/or, a special staining that specifically stains cell membrane may be performed.

The present invention can also be applied to a case in which a specimen multistained by the enzyme antibody method is observed. This is not limited to a specimen multistained by the enzyme antibody method, and the present invention can also be applied to a specimen labeled by the CISH method. Or, the present invention can also be applied to a specimen labeled (multistained) by the INC method and the CISH method at the same time.

Figure 2:
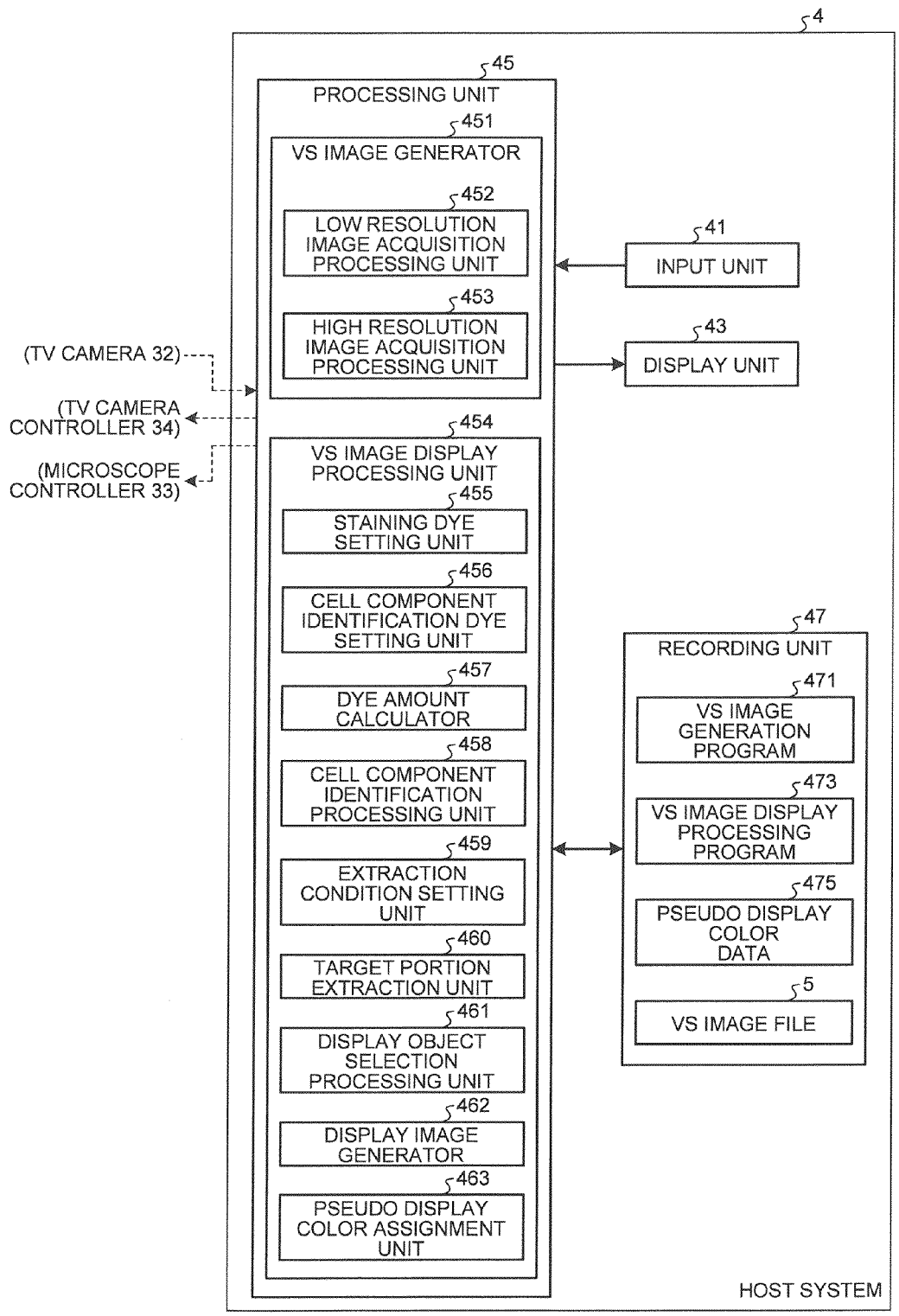
FIG. 2 is a block diagram showing a main functional configuration of a host system.

Next, a configuration of a microscope system 1 according to the first embodiment will be described. FIG. 1 is a schematic diagram for explaining an entire configuration of the microscope system 1. FIG. 2 is a block diagram showing a main functional configuration of a host system 4 which constitutes the microscope system 1. As shown in FIG. 1, the microscope system 1 is configured by a microscope device 2 and the host system 4 that are connected to each other so that data can be transmitted and received between them. Hereinafter, an optical axis of an objective lens 27 shown in FIG. 1 is defined as a Z direction, and a plane perpendicular to the Z direction is defined as an XY plane.

The microscope device 2 includes an electrically driven stage 21 on which a target specimen S is mounted, a microscope main body 24 having an approximate C shape in side view, a light source 28 disposed in a bottom back portion of the microscope main body 24 (a right portion in FIG. 1), and a lens barrel 29 mounted in an upper portion of the microscope main body 24. The microscope main body 24 supports the electrically driven stage 21 and holds the objective lens 27 through a revolver 26. A binocular unit 31 for visually observing a specimen image of the target specimen S and a TV camera 32 for capturing the specimen image of the target specimen S are attached to the lens barrel 29.

The electrically driven stage 21 is configured to be movable in the XYZ directions. Specifically, the electrically driven stage 21 can be moved in the XY plane by a motor 221 and an XY drive controller 223 that controls the drive of the motor 221. Under a control of a microscope controller 33, the XY drive controller 223 detects a predetermined origin position in the XY plane of the electrically driven stage 21 by an XY position origin sensor not shown in FIG. 1, and moves an observation point on the target specimen S by controlling a driving amount of the motor 221 by using the origin position as a base point. The XY drive controller 223 properly outputs an X position and a Y position of the electrically driven stage 21 during observation to the microscope controller 33. The electrically driven stage 21 can be moved in the Z direction by a motor 231 and a Z drive controller 233 that controls the drive of the motor 231. Under a control of the microscope controller 33, the Z drive controller 233 detects a predetermined origin position in the Z direction of the electrically driven stage 21 by a Z position origin sensor not shown in FIG. 1, and moves the target specimen S to an arbitrary Z position within a predetermined height range to focus the target specimen S by controlling a driving amount of the motor 231 by using the origin position as a base point. The Z drive controller 233 then properly outputs a Z position of the electrically driven stage 21 during observation to the microscope controller 33.

The revolver 26 is held rotatably to the microscope main body 24, and places the objective lens 27 over the target specimen S. The objective lens 27 is exchangably attached to the revolver 26 along with another objective lens having a different magnification (observation magnification), and only one objective lens 27 which is inserted in an optical path of an observation light to be used to observe the target specimen S is exclusively selected in accordance with rotation of the revolver 26. It is assumed that, in the first embodiment, the revolver 26 includes at least one objective lens with a relatively low magnification such as 2× or 4× magnification (hereinafter may be referred to as "low magnification objective lens") and at least one objective lens with high magnification such as 10×, 20×, or 40× magnification (hereinafter may be referred to as "high magnification objective lens") which is higher than that of the low magnification objective lens as the objective lenses 27. However, the low magnifications and the high magnifications as mentioned above are just an example, and only a magnification of one objective lens has to be higher than that of the other objective lens.

The microscope main body 24 internally includes an illumination optical system for transparently illuminating the target specimen S at a bottom portion thereof. The illumination optical system includes a collector lens 251 for collecting illumination light emitted from the light source 28, an illumination system filter unit 252, a field stop 253, an aperture stop 254, a folding mirror 255 for deflecting an optical path of the illumination light along the optical axis of the objective lens 27, a condenser optical element unit 256, and a top lens unit 257 which are arranged at appropriate positions along the optical path of the illumination light. The illumination light emitted from the light source 28 is irradiated to the target specimen S by the illumination optical system, and enters the objective lens 27 as the observation light.

The microscope main body 24 internally includes a filter unit 30 at an upper portion thereof. The filter unit 30 rotatably holds an optical filter 303 for limiting wavelength range of light formed into a specimen image within a predetermined range, and properly inserts the optical filter 303 into an optical path of the observation light in a post stage of the objective lens 27. The observation light passing through the objective lens 27 enters the lens barrel 29 via the filter unit 30.

The lens barrel 29 internally includes a beam splitter 291 for switching the optical path of the observation light passing through the filter unit 30 and guiding the optical path to the binocular unit 31 or the TV camera 32. The specimen image of the target specimen S is guided in the binocular unit 31 by the beam splitter 291 and visually observed by a microscope inspector via eyepieces 311. Or the specimen image is captured by the TV camera 32. The TV camera 32 includes an image sensor such as CCD or CMOS for forming the image of the specimen (specifically, visual field of the objective lens 27), captures the image of the specimen, and outputs image data of the image of the specimen to the host system 4.

Figure 3:
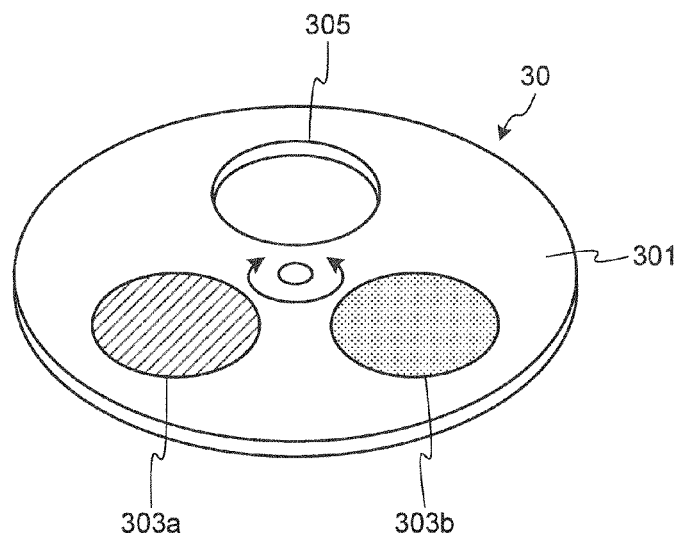
FIG. 3 is a schematic diagram for explaining a configuration of a filter unit.

Here, the filter unit 30 will be described in detail. The filter unit 30 is used when performing multiband imaging of the specimen image by the TV camera 32. FIG. 3 is a schematic diagram for explaining a configuration of the filter unit 30. The filter unit 30 shown in FIG. 3 includes a rotating optical filter switching unit 301 in which, for example, three mounting holes for mounting optical elements are formed, two optical filters 303 (303a and 303b) having spectral transmittance characteristics different from each other are mounted in two out of the three mounting holes, and the remaining hole is configured to be an empty hole 305.

Figure 4:
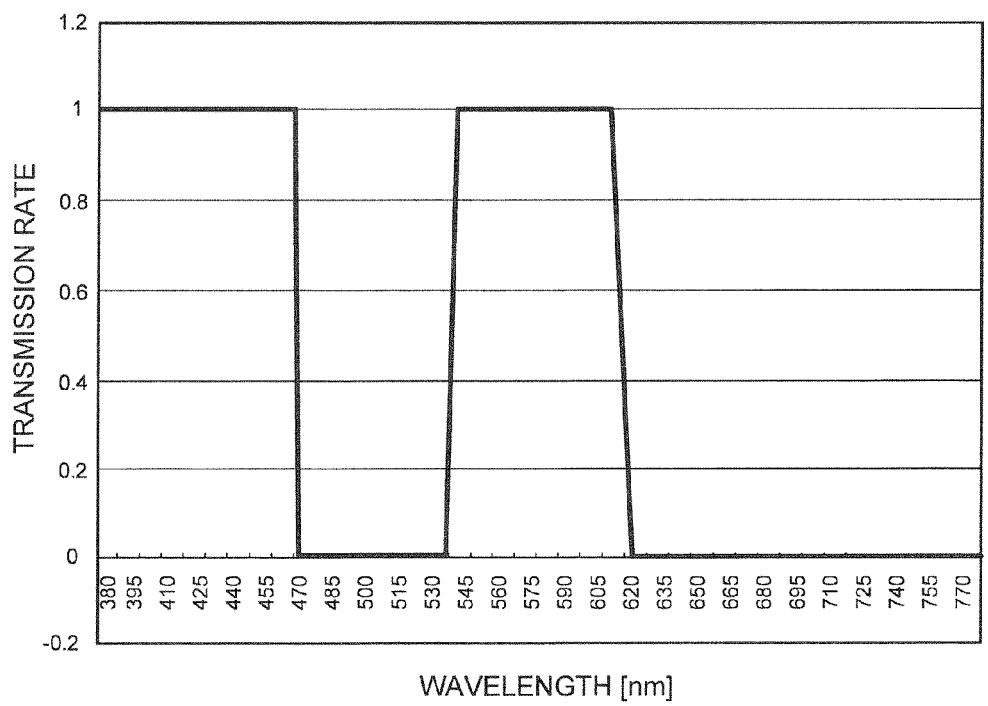
FIG. 4 is a diagram showing a spectral transmittance characteristic of one optical filter.
Figure 5:
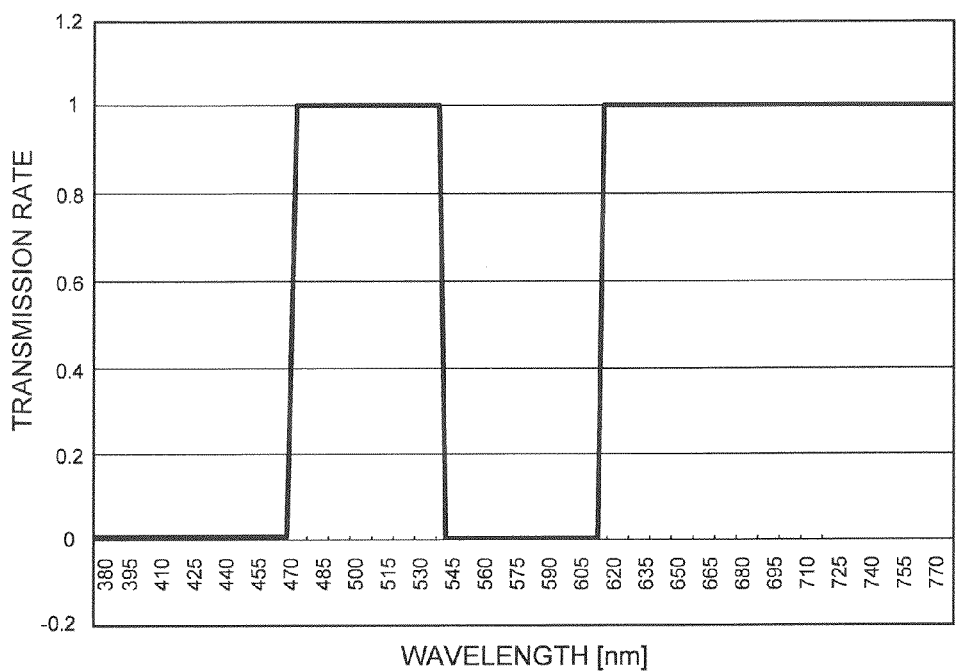
FIG. 5 is a diagram showing a spectral transmittance characteristic of the other optical filter.

FIG. 4 is a diagram showing the spectral transmittance characteristic of one optical filter 303a, and FIG. 5 is a diagram showing the spectral transmittance characteristic of the other optical filter 303b. As shown in FIGS. 4 and 5, the optical filters 303a and 303b respectively have spectral characteristics dividing R, G, and B bands of the TV camera 32 into two bands. When performing multiband imaging of the target specimen S, first, the optical filter switching unit 301 is rotated to insert the optical filter 303a into the optical path of the observation light, and a first imaging of the specimen image is performed by the TV camera 32. Next, the optical filter switching unit 301 is rotated to insert the optical filter 303b into the optical path of the observation light, and a second imaging of the specimen image is performed by the TV camera 32. By the first imaging and the second imaging, a three-band image is respectively obtained, and a multiband image (spectral image) of six bands is obtained by combining the two images.

Figure 6:
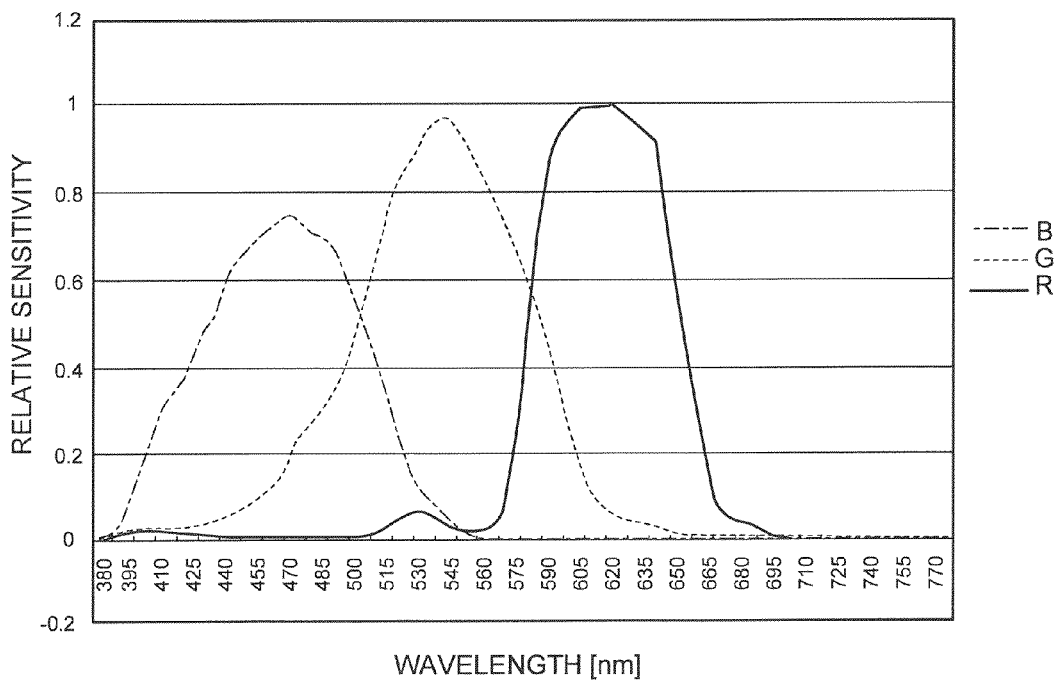
FIG. 6 is a diagram showing an example of spectral sensitivities of each of R, G, and B bands.

As described above, when performing multiband imaging of the specimen image by using the filter unit 30, the illumination light that is emitted from the light source 28 and irradiated to the target specimen S by the illumination optical system enters the objective lens 27 as the observation light. Thereafter, the light forms an image on the image sensor of the TV camera 32 via the optical filter 303a or the optical filter 303b. FIG. 6 is a diagram showing an example of spectral sensitivities of each of R, G, and B bands when capturing the specimen image by the TV camera 32.

When performing normal imaging (when capturing an RGB image of the specimen image), the optical filter switching unit 301 of FIG. 2 is rotated to place the empty hole 305 in the optical path of the observation light. Although, here, a case in which the optical filters 303a and 303b are arranged in a post stage of the objective lens 27 is described as an example, it is not limited to this, but the optical filters 303a and 303b may be arranged in any place in the optical path from the light source 28 to the TV camera 32. The number of the optical filters is not limited to two, but the filter unit may include three or more optical filters as necessary, and the number of the bands of the multiband image is not limited to six. For example, by using the technique disclosed in Japanese Laid-open Patent Publication No. 2008-51654, a 16-band multiband image may be captured by capturing a multiband image using a frame sequential method while switching 16 band-pass filters. The method for capturing a multiband image is not limited to the method in which the optical filters are switched. For example, a plurality of TV cameras is prepared. Then, the observation light is guided to each TV camera via a beam splitter or the like, and an imaging optical system in which spectral characteristics are complemented to each other may be configured. Based on this, it is possible to capture the specimen images by the TV cameras at the same time and obtain a multiband image at one time by combining the captured images, so that the process can be speeded up.

As shown in FIG. 1, the microscope device 2 includes the microscope controller 33 and a TV camera controller 34. The microscope controller 33 integrally controls operations of each component constituting the microscope device 2 under control of the host system 4. For example, the microscope controller 33 performs adjustments of each component of the microscope device 2 when the observation of the target specimen S is carried out, such as switching the objective lens 27 placed in the optical path of the observation light by rotating the revolver 26, controlling a light amount of the light source 28 and switching various optical elements according to the magnification and the like of the switched objective lens 27, and instructing the XY drive controller 223 and the Z drive controller 233 to move the electrically driven stage 21, and appropriately notifies the host system 4 of states of each component. The TV camera controller 34 drives the TV camera 32 and controls the image capturing operation of the TV camera 32 by performing on/off switching of automatic gain control, setting gain, on/off switching of automatic exposure control, setting exposure time, and the like under the control of the host system 4.

Meanwhile, the host system 4 includes an input unit 41, a display unit 43, a processing unit 45, a recording unit 47, and the like.

The input unit 41 is realized by, for example, a keyboard, a mouse, a touch panel, various switches, and the like, and outputs an operation signal responding to an operational input to the processing unit 45. The display unit 43 is realized by a display device such as an LCD or an EL display, and displays various screens on the basis of a display signal inputted from the processing unit 45.

The processing unit 45 is realized by hardware such as a CPU. The processing unit 45 integrally controls operations of the entire microscope system 1 by transmitting instructions and data to each component constituting the host system 4 and transmitting instructions to the microscope controller 33 and the TV camera controller 34 to operate each component of the microscope device 2 on the basis of an input signal inputted from the input unit 41, the states of each component of the microscope device 2 inputted from the microscope controller 33, the image data inputted from the TV camera 32, a program and data recorded in the recording unit 47, and the like. For example, the processing unit 45 performs AF (Auto Focus) processing to detects a focus position (focal position) where the image is focused by evaluating the contrast of the image at each Z position on the basis of the image data inputted from the TV camera 32 while moving the electrically driven stage 21 in the Z direction. The processing unit 45 performs compression process or decompression process based on a compression method such as JPEG and JPEG2000 when recording or displaying the image data inputted from the TV camera 32 to the recording unit 47 or the display unit 43. The processing unit 45 includes a VS image generator 451 and a VS image display processing unit 454 as a display processing unit.

The VS image generator 451 obtains a low resolution image and a high resolution image of the specimen image and generates a VS image. Here, the VS image is an image in which one or more images captured by the microscope device 2 are combined and generated. Hereinafter, an image, which is generated by combining a plurality of high resolution images which are partial images of the target specimen S captured by using the high magnification objective lens, and is a wide view and high resolution multiband image covering the entire area of the target specimen S, is referred to as the VS image.

The VS image generator 451 includes a low resolution image acquisition processing unit 452 and a high resolution image acquisition processing unit 453 as an image acquisition unit and a specimen image generator. The low resolution image acquisition processing unit 452 issues operation instructions to each component of the microscope device 2 and acquires a low resolution image of the specimen image. The high resolution image acquisition processing unit 453 issues operation instructions to each component of the microscope device 2 and acquires a high resolution image of the specimen image. Here, the low resolution image is acquired as an Rail image by using the low magnification objective lens to observe the target specimen S. On the other hand, the high resolution image is acquired as a multiband image by using the high magnification objective lens to observe the target specimen S.

The VS image display processing unit 454 calculates an amount of staining dye that stains a specimen position for each staining dye on the target specimen S on the basis of the VS image, extracts an area of the target portion in accordance with a predetermined extraction condition, generates an RGB image (display image) for displaying the VS image, and displays the RGB image (display image) on the display unit 43. The VS image display processing unit 454 includes a staining dye setting unit 455, a cell component identification dye setting unit 456, a dye amount calculator 457 as a dye amount acquisition unit, a cell component identification processing unit 458 as an element area identification unit, an extraction condition setting unit 459, a target portion extraction unit 460, a display object selection processing unit 461, a display image generator 462, and a pseudo display color assignment unit 463.

The staining dye setting unit 455 receives a registration operation of a staining dye by a user through the input unit 41, and sets the staining dye according to the operation input. The cell component identification dye setting unit 456 receives a selection operation of a cell component identification dye by the user through the input unit 41, and sets the cell component identification dye according to the operation input.

The dye amount calculator 457 estimates a spectral transmission rate at each specimen position on the target specimen S for each corresponding pixel constituting the VS image, and calculates an amount of dye at each specimen position on the basis of the estimated spectral transmission rate (estimated spectrum). The cell component identification processing unit 458 identifies a cell component whose cell component identification dye is set by the cell component identification dye setting unit 456.

The extraction condition setting unit 459 receives a setting operation of an extraction condition by the user through the input unit 41, and sets the extraction condition of the target portion according to the operation input. The target portion extraction unit 460 extracts an area of the target portion in the target specimen S satisfying the extraction condition set by the extraction condition setting unit 459.

The display object selection processing unit 461 receives a selection operation of a staining dye and/or a target portion to be displayed by the user through an input unit 41, and selects display object(s) according to the operation input. The display image generator 462 generates a display image of the VS image showing the display object(s) selected by the display object selection processing unit 461, and performs processing for displaying the display object(s) on the display unit 43. In the first embodiment, when a staining dye is selected as the display object, the display image generator 462 generates a display image showing a staining state of the selected staining dye. When a target portion is selected as the display object, the display image generator 462 generates a display image showing an area of the target portion. When a staining dye and a target portion are selected as the display objects, the display image generator 462 generates a display image showing a staining state of the selected staining dye and an area of the target portion. The pseudo display color assignment unit 463 receives an assignment operation of a pseudo display color by the user through the input unit 41, and arbitrarily assigns the pseudo display color to a staining dye according to the operation input.

The recording unit 47 is realized by a various IC memories such as a ROM including a flash memory that can be updated and a RAM, and storage media such as a hard disk and a CD-ROM that are installed inside the host system 4 or connected via a data communication terminal and reading devices thereof. In the recording unit 47, a program for operating the host system 4 and realizing various functions included in the host system 4, data used while the program is being executed, and the like are recorded.

The recording unit 47 records a VS image generation program 471 for causing the processing unit 45 to function as the VS image generator 451 and realizing VS image generation processing, and a VS image display processing program 473 for causing the processing unit 45 to function as the VS image display processing unit 454 and realizing VS image display processing. Further, the recording unit 47 records a VS image file 5. The details of the VS image file 5 will be described below.

Figure 7:
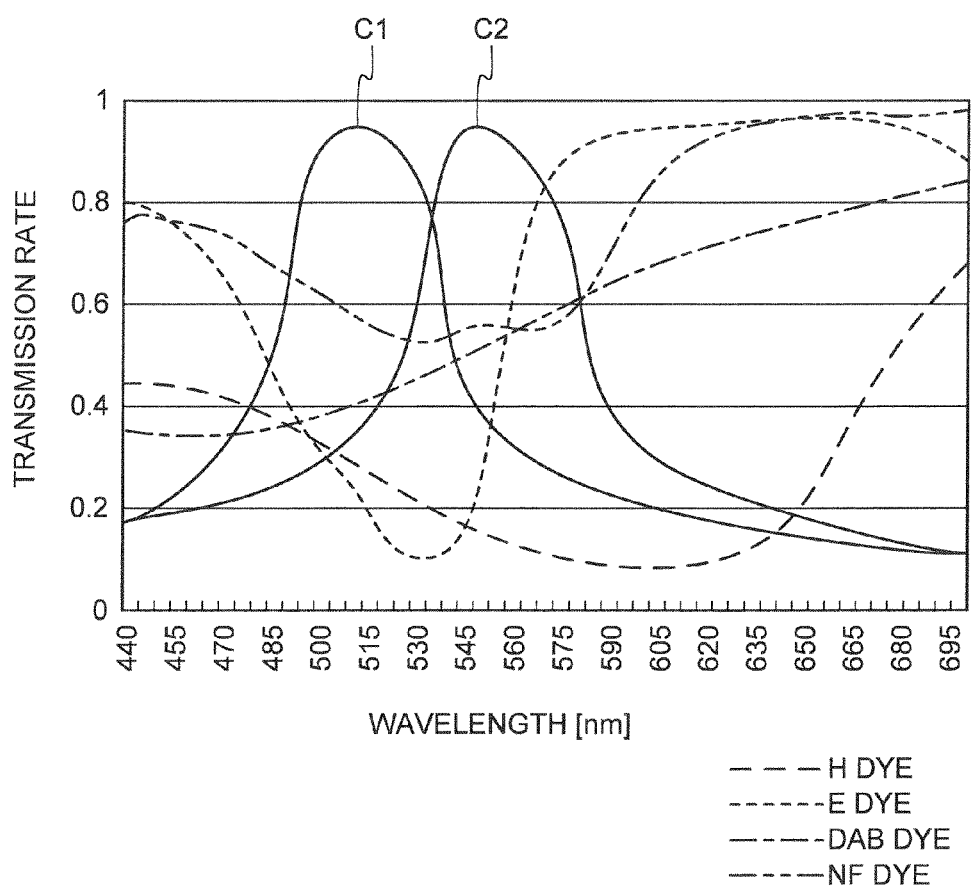
FIG. 7 is a diagram showing an example of a spectral transmittance characteristic of a pseudo display color.

Furthermore, the recording unit 47 records pseudo display color data 475. FIG. 7 is a diagram showing an example of spectral transmittance characteristics (spectra) of pseudo display colors. FIG. 7 shows spectra of two types of pseudo display colors C1 and C2 along with spectra of H dye, E dye, DAB dye, and NF dye that are staining dyes. In the first embodiment, spectra of pseudo display colors, such as the pseudo display color C1 and the pseudo display color C2 shown by solid lines in FIG. 7, that have spectra which are different from the spectra of the staining dyes and whose color intensities are higher than those of, for example, H dye and E dye are prepared. The spectra of pseudo display colors are recorded in the recording unit 47 as pseudo display color data 475 in advance, and the spectra of pseudo display colors are arbitrarily used as spectra of the staining dyes in accordance with a user operation.

The host system 4 can be realized by a publicly known hardware configuration including a CPU, a video board, a main storage device such as a main memory, an external storage device such as a hard disk and various storage media, a communication device, an output device such as a display device and a printing device, an input device, an interface device for connecting each unit or connecting an external input, and the like, and for example a general purpose computer such as a workstation and a personal computer can be used as the host system 4.

Figure 8:
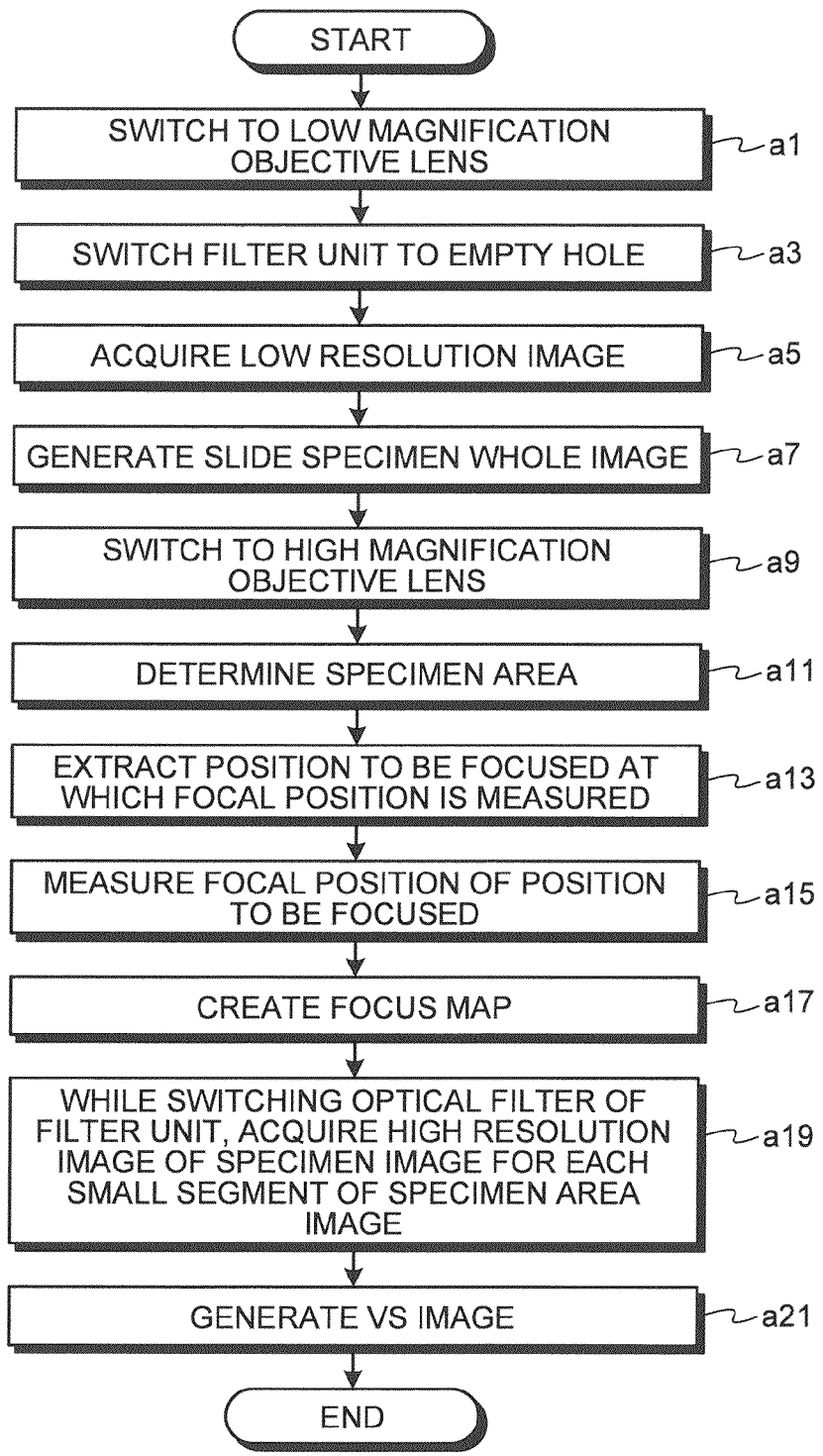
FIG. 8 is a flowchart showing an operation of the microscope system.

Next, the VS image generation process and the VS image display process according to the first embodiment will be described in this order. First, the VS image generation process will be described. FIG. 8 is a flowchart showing an operation of the microscope system 1 realized by the processing unit 45 of the host system 4 performing the VS image generation process. The operation of the microscope system 1 described here is realized by the VS image generator 451 reading and executing the VS image generation program 471 recorded in the recording unit 47.

As shown in FIG. 8, first, the low resolution image acquisition processing unit 452 of the VS image generator 451 outputs an instruction for switching the objective lens 27 used to observe the target specimen S to the low magnification objective lens to the microscope controller 33 (step a1). Responding to this, the microscope controller 33 rotates the revolver 26 as necessary and places the low magnification objective lens in the optical path of the observation light.

Next, the low resolution image acquisition processing unit 452 outputs an instruction for switching the filter unit 30 to the empty hole 305 to the microscope controller 33 (step a3). Responding to this, the microscope controller 33 rotates the optical filter switching unit 301 of the filter unit 30 as necessary and places the empty hole 305 in the optical path of the observation light.

Next, the low resolution image acquisition processing unit 452 issues operation instructions to operate each component of the microscope device 2 to the microscope controller 33, and the TV camera controller 34 and acquires a low resolution image (RGB image) of the specimen image (step a5).

Figure 9:
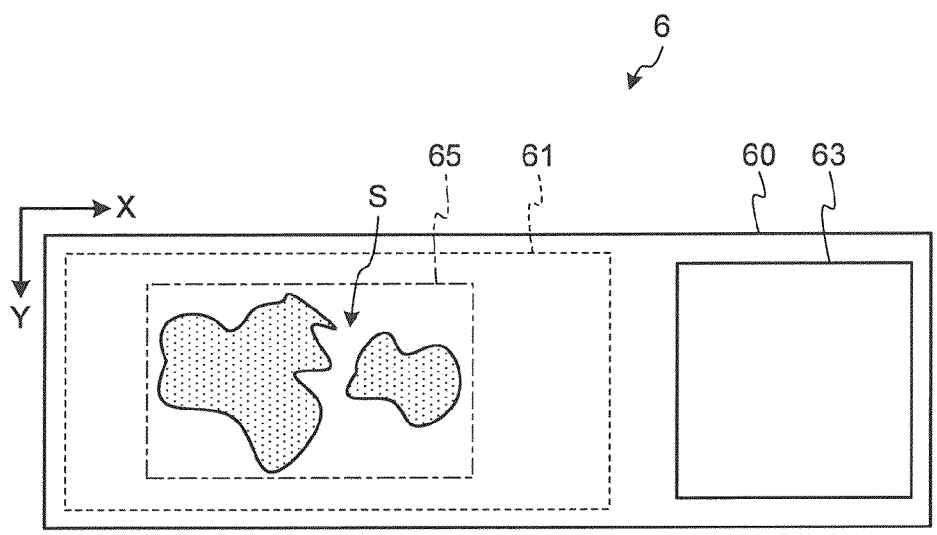
FIG. 9 is a diagram showing an example of a slide glass specimen.

FIG. 9 is a diagram showing an example of a slide glass specimen 6 mounted on an electrically driven stage 21. Actually, the target specimen S on the electrically driven stage 21 shown in FIG. 1 is mounted on the electrically driven stage 21 as the slide glass specimen 6 in which the target specimen S is mounted on a slide glass 60 as shown in FIG. 9. The target specimen S is mounted in a specimen search range 61 that is a predetermined area on the slide glass 60 (for example, an area of height: 25 mm×width: 50 mm in the left side of the slide glass 60 in FIG. 9). A label 63 on which information related to the target specimen S mounted on the specimen search range 61 is written is attached to a predetermined area on the slide glass 60 (for example, an area on the right side of the specimen search range 61). For example, a barcode, which is formed by encoding a slide specimen number that is identification information for identifying the target specimen S in accordance with a predetermined specification, is printed on the label 63, and the barcode is read by a barcode reader (not shown in the figures) included in the microscope system 1.

Responding to the operation instruction issued by the low resolution image acquisition processing unit 452 in step a5 in FIG. 8, the microscope device 2 captures an image of the specimen search range 61 on the slide glass 60 shown in FIG. 9. Specifically, the microscope device 2 divides the specimen search range 61 on the basis of the size of visual field determined in accordance with the magnification of the low magnification objective lens switched in step a1 (in other words, on the basis of the image capturing range of the TV camera 32 when using the low magnification objective lens to observe the target specimen S), and sequentially captures the specimen image of the specimen search range 61 for each divided section by the TV camera 32 while moving the electrically driven stage 21 in the XY plane according to the size of the divided section. The image data captured here is outputted to the host system 4, and is acquired by the low resolution image acquisition processing unit 452 as the low resolution image of the specimen image.

As shown in FIG. 8, the low resolution image acquisition processing unit 452 then combines the low resolution images of each divided section acquired in step a5, and generates one image covering the specimen search range 61 in FIG. 9 as a slide specimen whole image (step a7).

Next, the high resolution image acquisition processing unit 453 outputs an instruction for switching the objective lens 27 used to observe the target specimen S to the high magnification objective lens to the microscope controller 33 (step a9). Responding to this, the microscope controller 33 rotates the revolver 26 and places the high magnification objective lens in the optical path of the observation light.

Next, the high resolution image acquisition processing unit 453 automatically extracts and determines a specimen area 65 where the target specimen S is actually mounted in the specimen search range 61 in FIG. 9 on the basis of the slide specimen whole image generated in step a7 (step a11). The automatic extraction of the specimen area can be performed by appropriately employing a publicly known method. For example, the presence or absence of the specimen is determined for each pixel by binarizing each pixel in the slide specimen whole image, and a rectangular area enclosing a range of pixels determined to be pixels reflecting the target specimen S is determined to be the specimen area. It is also possible to receive a selection operation of the specimen area by a user through the input unit 41, and determine the specimen area according to the operation input.

Next, the high resolution image acquisition processing unit 453 cuts out an image of the specimen area (specimen area image) determined in step a11 from the slide specimen whole image, and selects a position at which the focal position is measured from the specimen area image to extract the position to be focused (step a13).

Figure 10:
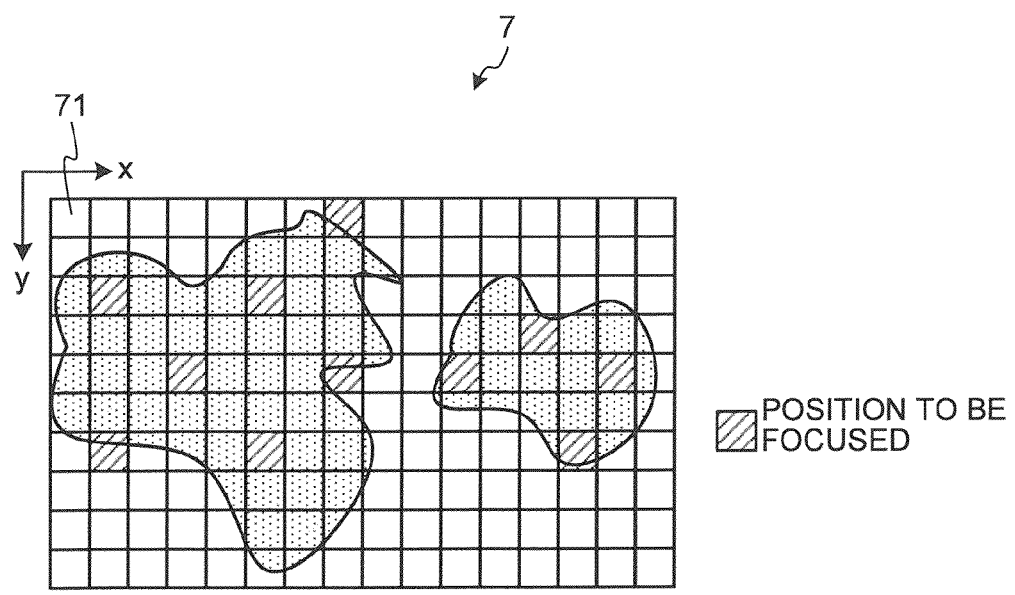
FIG. 10 is a diagram showing an example of a specimen area image.

FIG. 10 is a diagram showing an example of a specimen area image 7 cut out from the slide specimen whole image, and FIG. 10 shows an image of the specimen area 65 in FIG. 9. First, as shown in FIG. 10, the high resolution image acquisition processing unit 453 divides the specimen area image 7 into a grid-like pattern, and forms a plurality of small segments. Here, the segment size of the small segment corresponds to the size of the visual field determined according to the magnification of the high magnification objective lens switched in step a9 (in other words, the size of the image capturing range of the TV camera 32 when using the high magnification objective lens to observe the target specimen S).

Next, the high resolution image acquisition processing unit 453 selects a small segment used as the position to be focused from the plurality of small segments having been formed as shown in FIG. 10. This is because if the focal point is measured for every small segment, the processing time increases. Therefore, for example, a predetermined number of small segments are randomly selected from the small segments. Or, the small segments used as the position to be focused may be selected in accordance with a predetermined rule, such as, a small segment used as the position to be focused is selected from every predetermined number of small segments. When the number of the small segments is small, all the small segments may be selected as the position to be focused. The high resolution image acquisition processing unit 453 calculates the center coordinates of the selected small segment in the coordinates system (x, y) of the specimen area image 7, and converts the calculated center coordinates into the coordinate system (X, Y) of the electrically driven stage 21 of the microscope device 2 to obtain the position to be focused. The coordinate conversion is performed on the basis of the magnification of the objective lens 27 used to observe the target specimen S, the number of pixels and the pixel size of the image sensor included in the TV camera 32, or the like, and for example, can be realized by applying the publicly known technique described in Japanese Laid-open Patent Publication No. 09-281405.

Next, as shown in FIG. 8, the high resolution image acquisition processing unit 453 issues instructions to operate each component of the microscope device 2 to the microscope controller 33 and the TV camera controller 34 and measures the focal position of the position to be focused (step a15). At this time, the high resolution image acquisition processing unit 453 outputs the extracted positions to be focused to the microscope controller 33. Responding to this, the microscope device 2 moves the electrically driven stage 21 in the XY plane, and sequentially moves the positions to be focused to the optical axis position of the objective lens 27. The microscope device 2 then obtains image data at the position to be focused by the TV camera 32 while moving the electrically driven stage 21 in the Z direction at each position to be focused. The obtained image data is outputted to the host system 4, and acquired by the high resolution image acquisition processing unit 453. The high resolution image acquisition processing unit 453 evaluates the contrast of the image data at each Z position, and measures the focal position (Z position) of the target specimen S at each position to be focused.

After measuring the focal positions at each position to be focused as described above, the high resolution image acquisition processing unit 453 creates a focus map on the basis of the measurement result of the focal positions at each position to be focused and records the focus map to the recording unit 47 (step a17). Specifically, the high resolution image acquisition processing unit 453 sets the focal positions for all the small segments by interpolating focal positions of small segments not extracted as the position to be focused in step a13 by using nearby focal positions of the position to be focused, and creates the focus map.

Figures 11, 12:
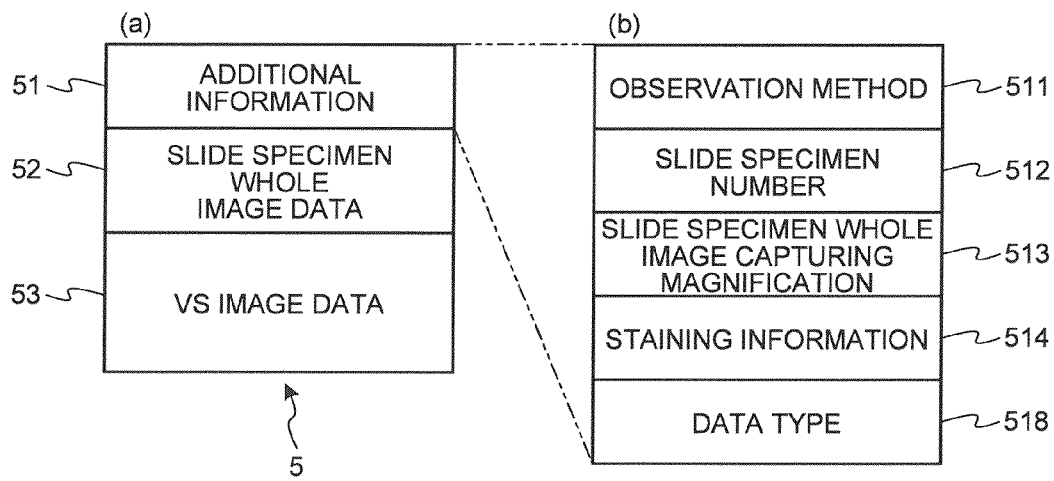
FIG. 11 is a diagram for explaining a data configuration example of a focus map.
FIG. 12 is a diagram for explaining a data configuration example of a VS image file.

FIG. 11 is a diagram showing a data configuration example of the focus map. As shown in FIG. 11, the focus map is a data table in which alignment numbers and positions of the electrically driven stage are associated with each other. The alignment numbers indicate each small segment in the specimen area image 7 shown in FIG. 10. Specifically, the alignment number represented by x is a serial number sequentially given to each column along the x direction starting from the left end to which the first number is given, and the alignment number represented by y is a serial number sequentially given to each row along the y direction starting from the uppermost row to which the first number is given. The alignment number represented by z is a value set when generating the VS image as a three-dimensional image. The positions of the electrically driven stage are positions of X, Y, and Z of the electrically driven stage 21 which are set as the focal position of the small segment of the specimen area image indicated by corresponding alignment numbers. For example, the alignment number of (x, y, z)=(1, 1, –) indicates a small segment 71 in FIG. 10, and the X position and the Y position, which are obtained by converting the center coordinates of the small segment 71 in the coordinate system (x, y) into the coordinate system (X, Y) of the electrically driven stage 21, correspond to $X_{11}$ and $Y_{11}$ respectively. The focal position (Z position) set for the small segment corresponds to $Z_{11}$.

Next, as shown in FIG. 8, the high resolution image acquisition processing unit 453 sequentially outputs instructions for switching the filter unit 30 to the optical filters 303a and 303b to the microscope controller 33. Along with the above operation, while referring to the focus map, the high resolution image acquisition processing unit 453 issues instructions to operate each component of the microscope device 2 to the microscope controller 33 and the TV camera controller 34, captures the specimen image for each small segment of the specimen area image by multiband imaging, and acquires a high resolution image (hereinafter may be referred to as "specimen area segment image") (step a19).

Responding to this, the microscope device 2 rotates the optical filter switching unit 301 of the filter unit 30, and first, sequentially captures the specimen image for each small segment of the specimen area image at the focal position thereof by the TV camera 32 while moving the electrically driven stage 21 with the optical filter 303a being placed in the optical path of the observation light. Next, the optical filter 303a is switched to the optical filter 303b and the optical filter 303b is placed in the optical path of the observation light, and thereafter the microscope device 2 captures the specimen image for each small segment of the specimen area image in the same way as described above. The image data captured here is outputted to the host system 4, and the image data is acquired by the high resolution image acquisition processing unit 453 as the high resolution image of the specimen image (specimen area segment image).

Next, the high resolution image acquisition processing unit 453 combines the specimen area segment images which are the high resolution images acquired in step a19, and generates one image covering the entire area of the specimen area 65 in FIG. 9 as the VS image (step a21).

In the above steps a13 to a21, the specimen area image is divided into small segments corresponding to the visual field of the high magnification objective lens. The specimen area segment images are acquired by capturing the specimen image for each small segment, and the VS image is generated by combining the specimen area segment images. On the other hand, the small segments may be set so that the specimen area segment images next to each other partially overlap each other at the border therebetween. And, one VS image may be generated by combining the specimen area segment images so that the positional relationship between the specimen area segment images next to each other is adjusted. Specific processing can be realized by applying publicly known techniques described in Japanese Laid-open Patent Publication No. 09-281405 and Japanese Laid-open Patent Publication No. 2006-343573, and in this case, the segment size of the small segment is set to a size smaller than the visual field of the high magnification objective lens so that edge portions of acquired specimen area segment images overlap each other between the specimen area segment images next to each other. In this way, even when the accuracy of movement control of the electrically driven stage 21 is low and the specimen area segment images next to each other are not connected continuously, a VS image in which connection portions are continuously connected by the overlapping portions can be generated.

As a result of the VS image generation process described above, a wide view and high resolution multiband image covering the entire area of the target specimen S can be acquired. Here, the processes of step a1 to step a21 is performed automatically. Therefore, a user only has to mount the target specimen S (specifically, the slide glass specimen 6 in FIG. 9) on the electrically driven stage 21, and input a start instruction operation of the VS image generation process via the input unit 41. The processes may be interrupted as necessary at any of steps a1 to a21, and a user operation may be inputted. For example, process for changing the high magnification objective lens to be used to another objective lens with different magnification in accordance with an operation input after step a9, process for changing the determined specimen area in accordance with an operation input after step a11, process for changing, adding, or deleting the extracted position to be focused in accordance with an operation input after step a13, and the like may be performed as necessary.

Figure 13:
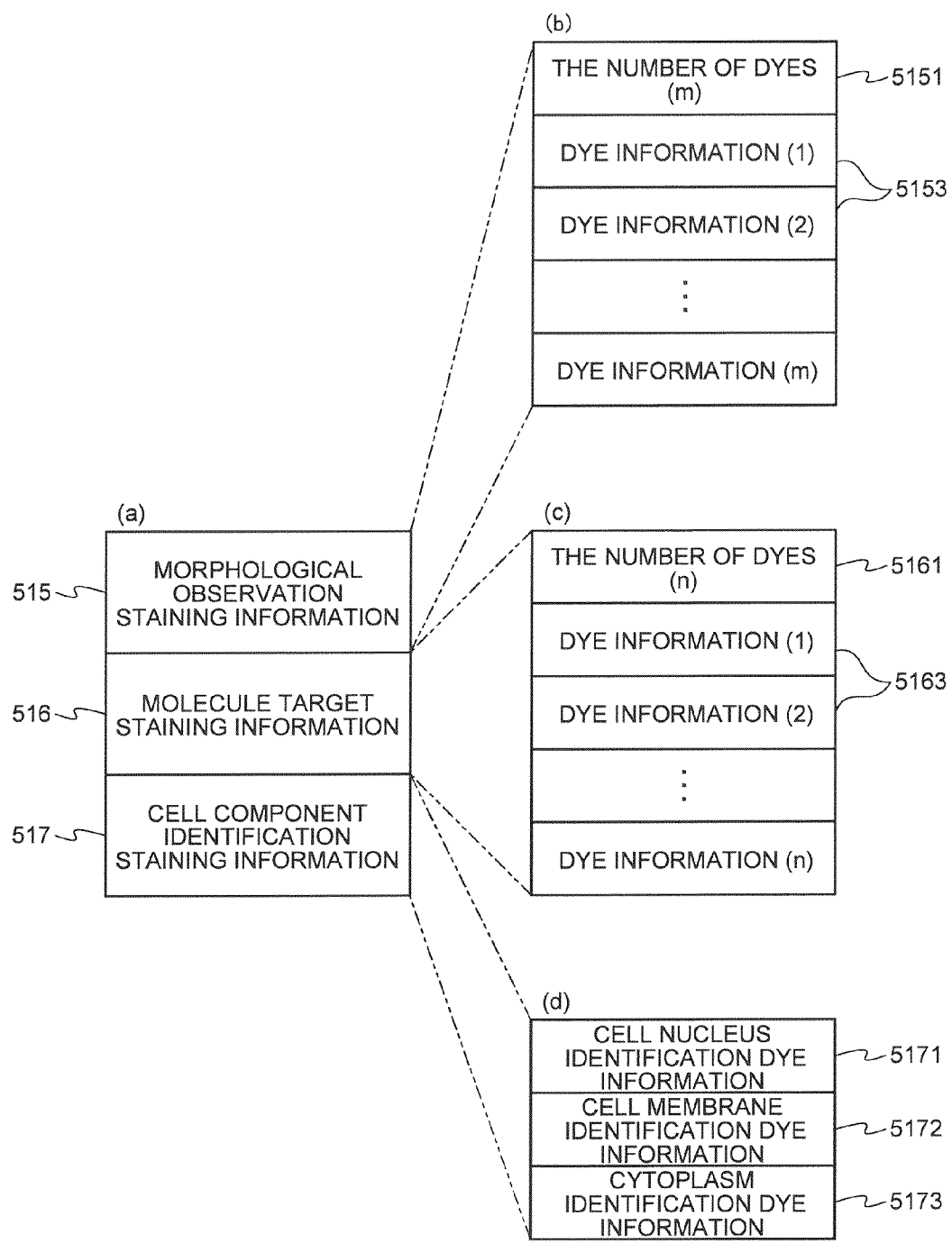
FIG. 13 is a diagram for explaining a data configuration example of staining information.
Figure 14:
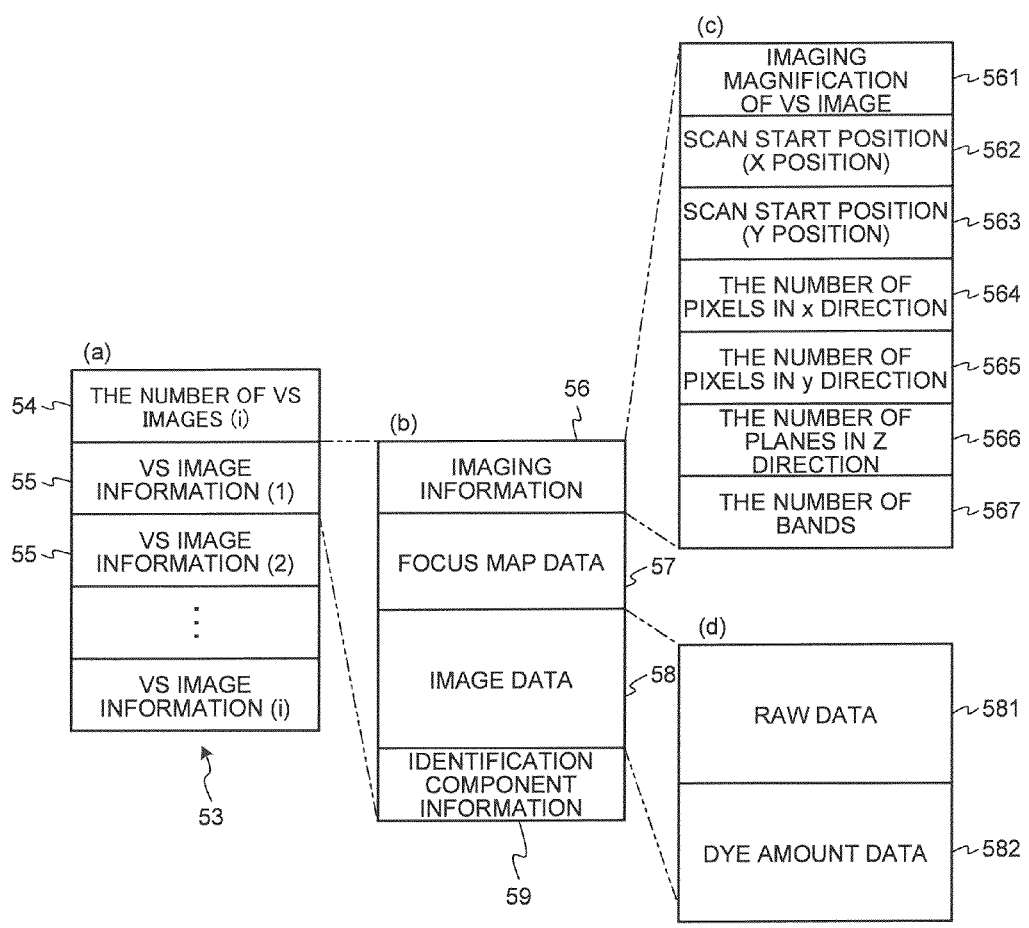
FIG. 14 is a diagram for explaining a data configuration example of VS image data.

FIGS. 12 to 14 are diagrams for explaining a data configuration example of a VS image file 5 acquired as a result of the VS image generation process and recorded in the recording unit 47. As shown in (a) of FIG. 12, the VS image file 5 includes additional information 51, slide specimen whole image data 52, and VS image data 53.

As shown in (b) of FIG. 12, in the additional information 51, an observation method 511, a slide specimen number 512, a slide specimen whole image capturing magnification 513, staining information 514, data type 518, and the like are set.

The observation method 511 is an observation method of the microscope device 2 used to generate the VS image, and for example "bright field observation method" is set in the first embodiment. When a microscope device in which a specimen can be observed by another observation method such as dark field observation, fluorescence observation, differential interference observation, and the like is used, the observation method used when the VS image is generated is set.

In the slide specimen number 512, for example, a slide specimen number read from the label 63 of the slide glass specimen 6 shown in FIG. 9 is set. The slide specimen number is, for example, an ID uniquely assigned to the slide glass specimen 6, and the target specimen S can be identified by the ID. In the slide specimen whole image capturing magnification 513, the magnification of the low magnification objective lens used when the slide specimen whole image is acquired is set. The slide specimen whole image data 52 is image data of the slide specimen whole image.

In the staining information 514, the staining dye that stains the target specimen S is set. Specifically, although H dye, E dye, DAB dye, and NF dye are set in the first embodiment, the staining information 514 is set when a user manually inputs and registers the dye that stains the target specimen S in a process of the VS image display processing described below.

Specifically, as shown in (a) of FIG. 13, the staining information 514 includes morphological observation staining information 515 in which the morphological observation dye among the staining dyes is set, molecule target staining information 516 in which the molecule target dye is set, and cell component identification staining information 517 selected from the staining dyes (the morphological observation dye and the molecule target dye) set in the morphological observation staining information 515 or the molecule target staining information 516.

As shown in (b) of FIG. 13, the morphological observation staining information 515 includes the number of dyes 5151 and dye information (1) to (m) 5153, the number of which corresponds to the number of dyes 5151. In the number of dyes 5151, the number of the morphological observation dyes staining the target specimen S is set, and in the dye information (1) to (m) 5153, for example, dye names of the morphological observation dyes are set. In the first embodiment, "2" is set as the number of dyes 5151, and "H dye" and "E dye" are set as two dye information items 5153. The molecule target staining information 516 is configured in a similar manner, and as shown in FIG. 13(c), the molecule target staining information 516 includes the number of dyes 5161 and dye information (1) to (n) 5163, the number of which corresponds to the number of dyes 5161. In the number of dyes 5161, the number of the molecule target dyes staining the target specimen S is set, and in the dye information (1) to (n) 5163, for example, dye names of the molecule target dyes are set. In the dye information (1) to (n) 5163, comment information inputted by a user with respect to a corresponding molecule target dye on a dye registration screen (refer to FIG. 17) described below is arbitrarily set. In the first embodiment, "2" is set as the number of dyes 5161, and "DAB dye" and "NF dye" are set as two dye information items 5163.

As shown in (d) of FIG. 13, the cell component identification staining information 517 includes cell nucleus identification dye information 5171, cell membrane identification dye information 5172, and cytoplasm identification dye information 5173. In the cell nucleus identification dye information 5171, a dye name of the cell nucleus identification dye and a dye amount threshold value used as a standard when identifying the cell nucleus. In the cell membrane identification dye information 5172, a dye name of the cell membrane identification dye and a dye amount threshold value used as a standard when identifying the cell membrane. In the cytoplasm identification dye information 5173, a dye name of the cytoplasm identification dye and a dye amount threshold value used as a standard when identifying the cytoplasm. In the dye amount threshold values, a value is set which is inputted by a user with respect to a corresponding cell component (cell nucleus, cell membrane, or cytoplasm) on an identification dye selection screen (refer to FIG. 18) described below. In the first embodiment, as the cell nucleus identification dye information 5171, "H dye" and a dye amount threshold value inputted by a user with respect to the cell nucleus identification dye that is the "H dye" are set. As the cell membrane identification dye information 5172, "NF dye" and a dye amount threshold value inputted by a user with respect to the cell membrane identification dye that is the "NF dye" are set. Since the cytoplasm is not identified in the first embodiment, "Not in use" is set (or nothing is set) in the cytoplasm identification dye information 5173.

The data type 518 in (b) of FIG. 12 shows a data type of the VS image. For example, the data type 518 is to distinguish whether, in the VS image data 53, only image data (raw data) 581 (refer to (d) of FIG. 14) of the VS image is recorded as image data 58 (refer to (b) of FIG. 14) or the dye amount has been already calculated for each pixel and dye amount data 582 ((d) of FIG. 14) is recorded. For example, when VS image generation processing is performed, only the raw data 581 of the VS image is recorded as the image data 58, so that identification information indicating the raw data is set in the data type 518. When VS image display processing described below is performed, the dye amount of each dye is calculated for each pixel of the VS image and recorded as the dye amount data 582. At this time, the data type 518 is updated to identification information indicating the dye amount data.

In the VS image data 53, various information related to the VS image is set. Specifically, as shown in (a) of FIG. 14, the VS image data 53 includes the number of VS images 54 and VS image information 55 (1) to (I), the number of which corresponds to the number of VS images 54. The number of VS images 54 is the number of VS image information 55 recorded in the VS image data 53, and corresponds to I. Regarding the data configuration example of the VS image data 53 shown in (a) of FIG. 14, it is assumed a case that a plurality of VS images is generated from one specimen. Although, in the example described above and shown in FIG. 9, the slide glass specimen 6 in which one specimen area 65 is extracted as an area where the target specimen S is actually mounted is described, there are slide glass specimens in which a plurality of specimens are placed separately. In this case, it is not necessary to create the VS image of an area not including a specimen. Therefore, when a plurality of specimens is placed separately from each other by a certain distance, an area of each specimen placed separately is extracted individually, and the VS image is generated for each area of the extracted specimens. The number of VS images generated at this time is set as the number of VS images 54. Various information related to each VS image is set as the VS image information 55 (1) to (I). In the example of FIG. 9, although two specimen areas are included in the specimen area 65, the two specimen areas are extracted as one specimen area 65 because the distance between the two specimen areas is small.

In each VS image information 55, as shown in (b) of FIG. 14, imaging information 56, focus map data 57, image data 58, identification component information 59, and the like are set.

In the imaging information 56, as shown in (c) of FIG. 14, an imaging magnification of VS image 561, a scan start position (X position) 562, a scan start position (Y position) 563, the number of pixels in the x direction 564, the number of pixels in the y direction 565, the number of planes in the Z direction 566, the number of bands 567, and the like are set.

In the imaging magnification of VS image 561, the magnification of the high magnification objective lens used when the VS image is acquired is set. The scan start position (X position) 562, the scan start position (Y position) 563, the number of pixels in the x direction 564, and the number of pixels in the y direction 565 indicate an image capturing range of the VS image. Specifically, the scan start position (X position) 562 is the X position of the scan start position of the electrically driven stage 21 when the image capturing of the specimen area segment images constituting the VS image is started, and the scan start position (Y position) 563 is the Y position from which the scan is started. The number of pixels in the x direction 564 is the number of pixels of the VS image in the x direction, the number of pixels in the y direction 565 is the number of pixels of the VS image in the y direction, and both numbers indicate the size of the VS image.

The number of planes in the Z direction 566 corresponds to the number of sectioning levels in the Z direction, and when generating the VS image as a three-dimensional image, the number of imaging planes in the Z direction is set in the number of planes in the Z direction 566. In the first embodiment, "1" is set in the number of planes in the Z direction 566. The VS image is generated as a multiband image. The number of bands of the multiband image is set in the number of bands 567, and "6" is set in the first embodiment.

The focus map data 57 shown in (b) of FIG. 14 is the data of the focus map shown in FIG. 11. The image data 58 is image data of the VS image. As shown in (d) of FIG. 14, the image data 58 includes the raw data 581 in which raw data of 6 bands is set and the dye amount data 582 in which data of the dye amounts of each staining dye calculated for each pixel in a process of the VS image display processing described below is set.

In the identification component information 59, map data in which whether or not each pixel of the VS image is a pixel of a cell component is set, morphological characteristic data in which morphological characteristic amounts of an area identified as a cell component is set, a list of pixel positions in the area identified as a cell component, and the like are stored. The details of the identification component information 59 will be described below with reference to FIGS. 24 and 25.

Figure 15:
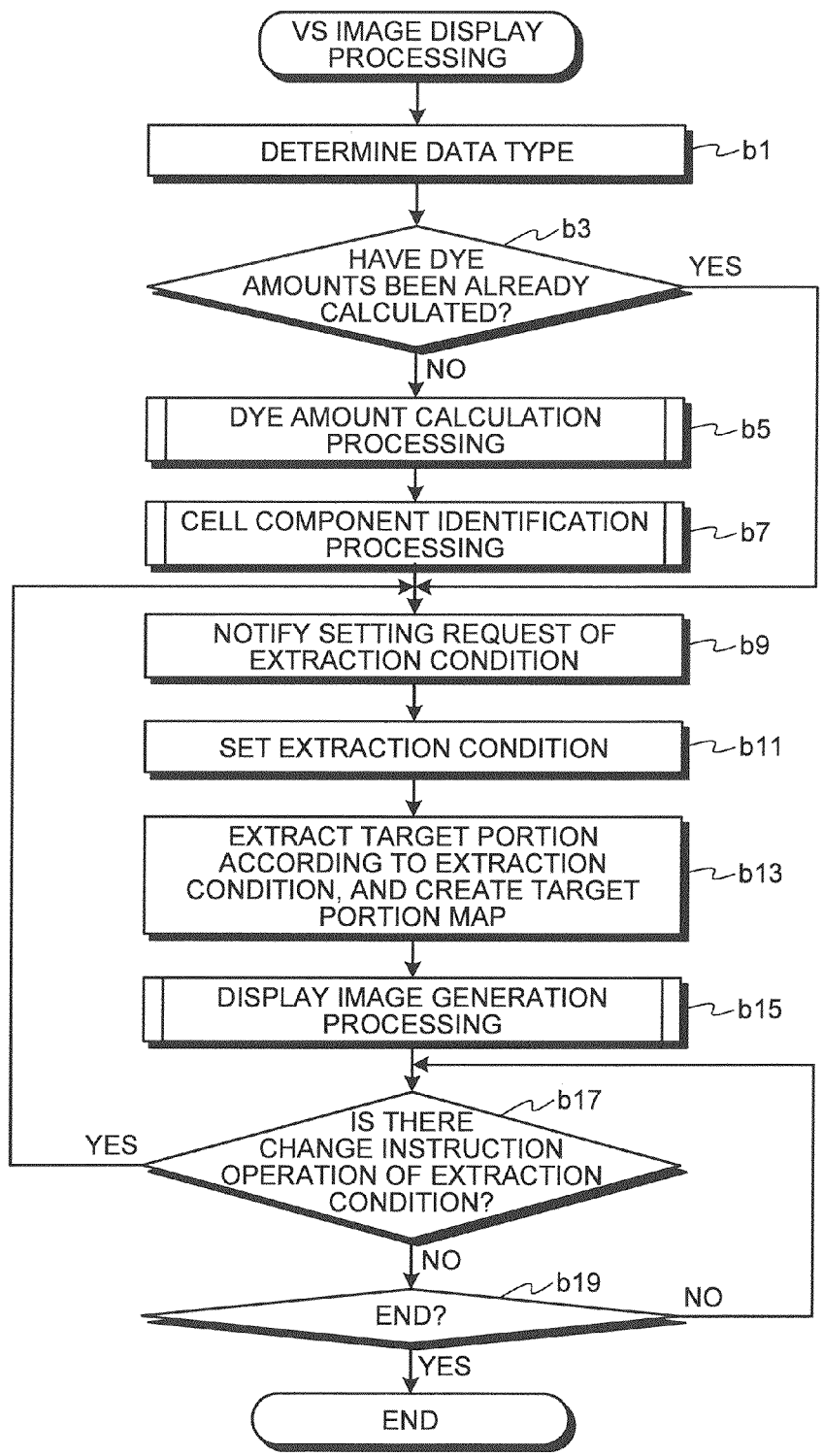
FIG. 15 is a flowchart showing a processing procedure of VS image display processing according to the first embodiment.

Next, the VS image display processing according to the first embodiment will be described. FIG. 15 is a flowchart showing a processing procedure of the VS image display processing according to the first embodiment. The processing described here is realized by the VS image display processing unit 454 reading and executing the VS image display processing program 473 recorded in the recording unit 47.

In the VS image display processing, first, the VS image display processing unit 454 reads the data type 518 (refer to (b) of FIG. 12) from the VS image file 5, and determines the data type of the VS image (step b1). When the identification information indicating the dye amount data is set in the data type 518 and the dye amounts have been already calculated for each pixel of the VS image (step b3: Yes), the process proceeds to step b9.

Figure 16:
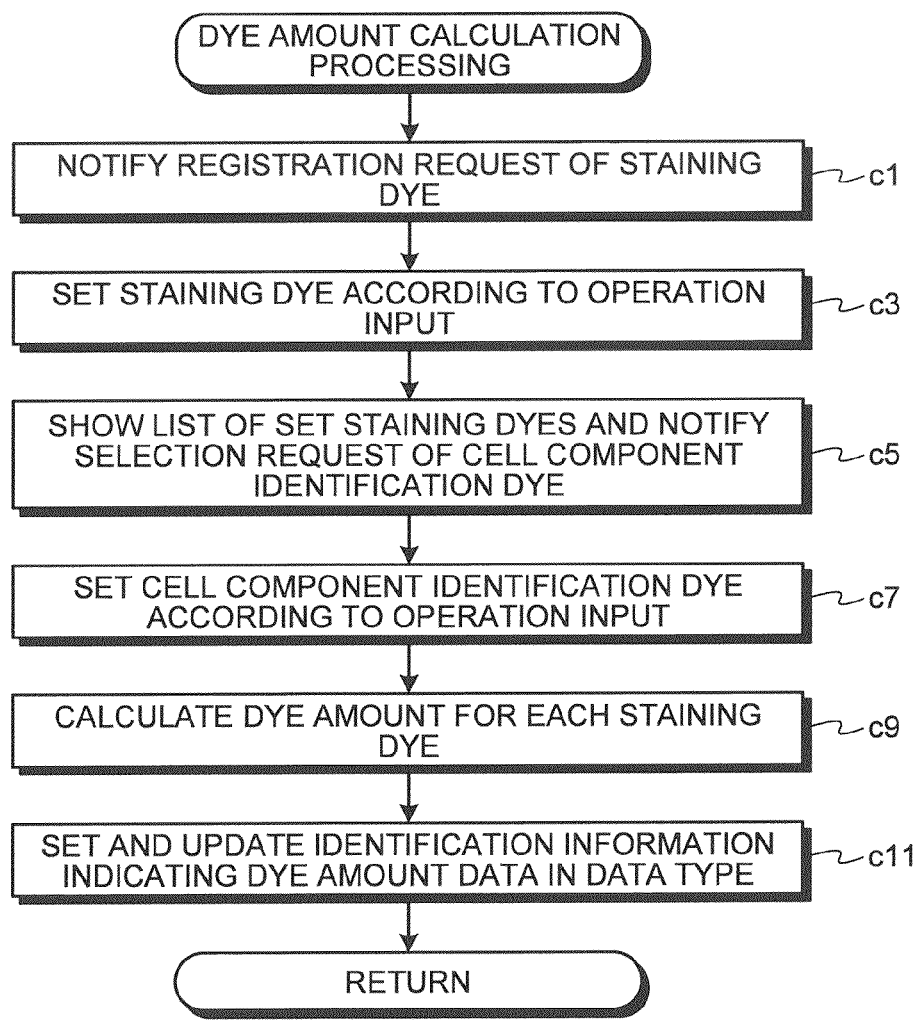
FIG. 16 is a flowchart showing a processing procedure of dye amount calculation processing.

On the other hand, when the identification information indicating the raw data is set in the data type 518 and the dye amounts have not been calculated yet for each pixel of the VS image (step b3: No), the process proceeds to dye amount calculation processing (step b5). FIG. 16 is a flowchart showing a processing procedure of the dye amount calculation processing.

Figure 17:
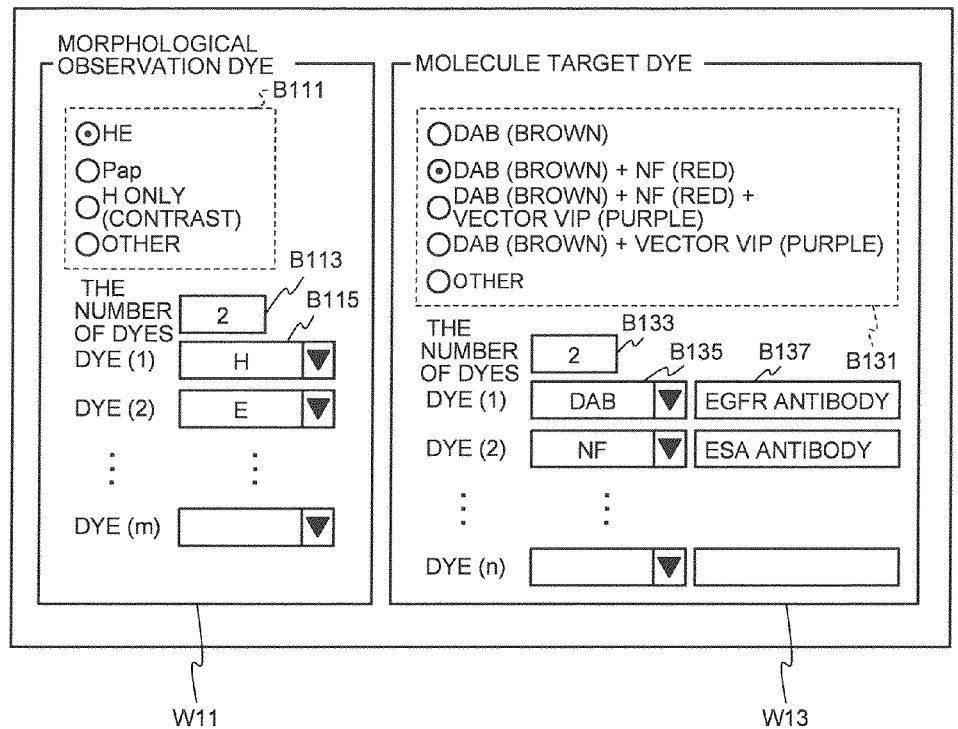
FIG. 17 is a diagram showing an example of a dye registration screen.

In the dye amount calculation processing, first, the staining dye setting unit 455 performs processing for displaying a notification of a registration request of the staining dye staining the target specimen S on the display unit 43 (step c1). For example, the staining dye setting unit 455 performs processing for displaying a dye registration screen on the display unit 43 to notify the registration request of the staining dye, and receives a registration operation of the staining dye by a user on the dye registration screen. FIG. 17 is a diagram showing an example of the dye registration screen. As shown in FIG. 17, the dye registration screen includes two screens which are a morphological observation dye registration screen W11 and a molecule target dye registration screen W13.

In the morphological observation dye registration screen W11, an input box B113 for inputting the number of morphological observation dyes and a plurality of (m) spin boxes B115 for selecting the morphological observation dyes are arranged. The spin box B115 shows a list of dyes as options, and prompts to select one of the dyes. Although the dyes shown in the list are not illustrated as an example, dyes known as a morphological observation dye are appropriately included in the list. A user operates the input unit 41 to input the number of the morphological observation dyes that actually stain the target specimen S into the input box B113, and registers the staining dye by selecting the name of the dye in the spin box B115. When the number of the morphological observation dyes is two or more, the names of the dyes are respectively selected in the other spin boxes B115.

The morphological observation dye registration screen W11 also includes a typical staining selection unit B111. In the typical staining selection unit B111, four options are shown, which are a dye (HE) used for HE staining typical for the morphological observation staining, a dye (Pap) used for Pap staining, a dye (H only) used for H staining, and another dye. The options shown in the typical staining selection unit B111 are not limited to those illustrated in the example, and a user may set the options. However, the dyes shown in the example can be registered only by checking the corresponding item, so that the registration operation is simplified. For example, as shown in FIG. 17, when "HE" is checked, "2" is automatically inputted into the input box B113, and "H" and "E" are automatically inputted into the spin boxes B115 of Dye (1) and Dye (2) respectively. In the first embodiment, the target specimen S is HE-stained, and thus a user can register staining dyes (morphological observation dyes) by checking the "HE" in the typical staining selection unit B111.

On the other hand, in the molecule target dye registration screen W13, an input box B133 for inputting the number of molecule target dyes, a plurality of (n) spin boxes B135 for selecting the molecule target dyes, and a plurality of (n) comment input fields B137 corresponding to each of the spin boxes B135 are arranged. The spin box B135 shows a list of dyes as options, and prompts to select one of the dyes. Although the dyes shown in the list are not illustrated as an example, dyes known as a molecule target dye are appropriately included in the list. A user operates the input unit 41 to input the number of the molecule target dyes that actually stain the target specimen S into the input box B133, and registers the staining information by selecting the name of the dye in the spin box B135. In the comment input field B137, the user can freely write information (comment information) related to the molecule target dye selected in the corresponding spin box B135. For example, in FIG. 17, a case in which a name of antibody stained (visualized) by the corresponding molecule target dye is inputted into the comment input field B137 as the comment information is illustrated as an example. As the other comment information, for example, there are names of antigens (in other words, target molecules) labeled by the above-described antibodies.

In a similar manner to the morphological observation dye registration screen W11, the molecule target dye registration screen W13 includes a typical staining selection unit B131 that shows main labeling enzymes and combinations thereof. The options shown in the typical staining selection unit B131 are not limited to those illustrated in the example, and a user may set the options. The molecule target dyes according to the first embodiment are the DAB dye and the NF dye, and as shown in FIG. 17, the staining dyes (molecule target dyes) can be registered by checking "DAB (brown)+NF (red)" in the typical staining selection unit B131. Specifically, at this time, "2" is automatically inputted into the input box B133, and "DAB" and "NF" are automatically inputted into the spin boxes B135 of Dye (1) and Dye (2) respectively.

Return to FIG. 16. The staining dye setting unit 455 defines information of the morphological observation dyes manually inputted and registered by the user on the dye registration screen as described above as the morphological observation staining information 515 (refer to (a) and (b) of FIG. 13) of the staining information 514 (refer to (b) of FIG. 12), defines information of the molecule target dyes as the molecule target staining information 516 (refer to (a) and (c) of FIG. 13), and sets them in the VS image file 5 (step c3). In the first embodiment, H dye, E dye, DAB dye, and NF dye are set as the staining dyes by this processing.

Figure 18:
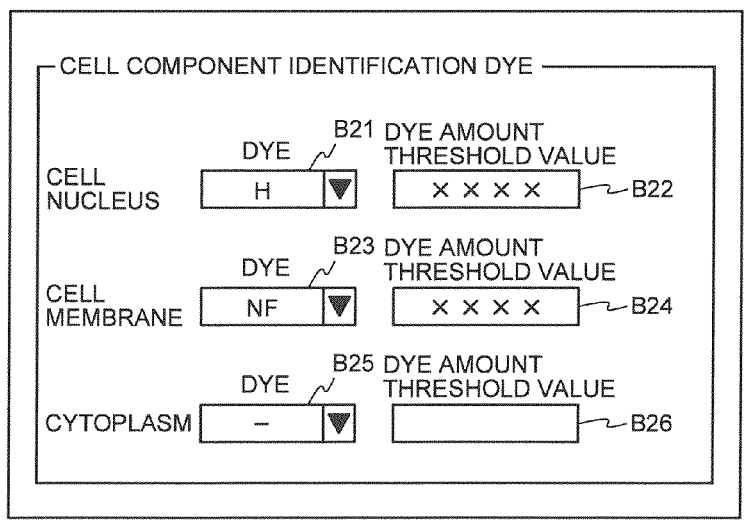
FIG. 18 is a diagram showing an example of an identification dye selection screen.

Next, the cell component identification dye setting unit 456 performs processing for displaying a notification of a selection request of the cell component identification dye (step c5). For example, the cell component identification dye setting unit 456 performs processing for displaying an identification dye selection screen on the display unit 43 to notify the selection request of the cell component identification dye, and receives a selection operation of the cell component identification dye by the user on the identification dye selection screen. At this time, the cell component identification dye setting unit 456 shows the list of the staining dyes set in step c3, and receives the selection operation selecting a cell component identification dye from the list. FIG. 18 is a diagram showing an example of the identification dye selection screen.

As shown in FIG. 18, on the identification dye selection screen, a spin box 321 for selecting the cell nucleus identification dye and an input box 322 for inputting the dye amount threshold value thereof, a spin box 323 for selecting the cell membrane identification dye and an input box 324 for inputting the dye amount threshold value thereof, and a spin box B25 for selecting the cytoplasm identification dye and an input box 326 for inputting the dye amount threshold value thereof are arranged.

Here, in the spin boxes B21, 323, and 325, a list of the morphological observation dyes and the molecule target dyes set as the staining dyes in step c3 in FIG. 16 is shown as options. The dye amount threshold values inputted into the input boxes B22, 324, and 326 are used as references when identifying a corresponding cell component in the processing thereafter. For example, when identifying the cell nucleus, a pixel whose dye amount of the cell nucleus identification dye selected in the spin box B21 is greater than or equal to the value inputted into the input box 322 is selected as a candidate pixel of the cell nucleus. In a similar manner, when identifying the cell membrane, a pixel whose dye amount of the cell membrane identification dye selected in the spin box 323 is greater than or equal to the value inputted into the input box 324 is selected as a candidate pixel of the cell membrane. When identifying the cytoplasm, a pixel whose dye amount of the cytoplasm identification dye selected in the spin box 325 is greater than or equal to the value inputted into the input box B26 is selected as a candidate pixel of the cytoplasm.

The user operates the input unit 41, selects staining dyes used as the cell nucleus identification dye, the cell membrane identification dye, and the cytoplasm identification dye from the staining dyes in the spin boxes 321, 323, and B25, and inputs the dye amount threshold values for identifying a corresponding cell component into the input box 322, 324, and B26. In the first embodiment, for example, the cell nucleus identification dye "H" is selected in the spin box B21, and the dye amount threshold value thereof is inputted. The cell membrane identification dye "NF" is selected in the spin box B23, and the dye amount threshold valued thereof is inputted.

Return to FIG. 16. The cell component identification dye setting unit 456 defines the names of the dyes and the dye amount threshold values manually inputted by the user on the identification dye selection screen as described above as the cell component identification staining information 517 (refer to (a) and (d) of FIG. 13), and sets them in the VS image file 5 (step c7). In the first embodiment, by this processing, the H dye and the dye amount threshold value thereof are set as the cell nucleus identification dye information 5171 and the NF dye and the dye amount threshold value thereof are set as the cell membrane identification dye information 5172. In the processing thereafter (cell component identification processing in FIG. 19), the cell nucleus and the cell membrane are identified.

Next, the dye amount calculator 457 calculates the dye amounts at each specimen position on the target specimen S corresponding to each pixel value in the generated VS image for each staining dye set in step c3 on the basis of each pixel value in the generated VS image (step c9). The calculation of the dye amounts can be performed by, for example, applying the publicly known technique described in Japanese Laid-open Patent Publication No. 2008-51654.

Processing procedure will be briefly described. First, the dye amount calculator 457 estimates a spectrum (estimated spectrum) at each corresponding specimen position on the target specimen S for each pixel on the basis of the pixel values in the VS image. As the method for estimating spectrum from a multiband image, for example, Wiener estimation can be used. Next, the dye amount calculator 457 estimates (calculates) a dye amount of the target specimen S for each pixel by using a reference dye spectrum of the dye (staining dye) to be calculated that is measured in advance and recorded in the recording unit 47.

Here, the calculation of the dye amount will be briefly described. It is known that, generally, a material that transmits light follows Lambert-Beer law represented by the following Equation (1) described below between the strength of incoming light $I_0(\lambda)$ for each wavelength $\lambda$ and the strength of outgoing light $I(\lambda)$.

$$\frac{I(\lambda)}{I_0(\lambda)} = e^{-k(\lambda) \cdot d} \tag{1}$$

where $k(\lambda)$ represents a value which is unique to the material and determined depending on wavelength, and d represents a depth of the material. The left-hand side of Equation (1) indicates a spectral transmission rate $t(\lambda)$.

For example, when the specimen is stained by n types of dyes dye 1, dye 2, . . . , dye n, the following Equation (2) is established for each wavelength $\lambda$ by Lambert-Beer law.

$$\frac{I(\lambda)}{I_0(\lambda)} = e^{-(k_1(\lambda) \cdot d_1 + k_2(\lambda) \cdot d_2 + \ldots + k_n(\lambda) \cdot d_n)} \tag{2}$$

where $k_1(\lambda)$, $k_2(\lambda)$, . . . , $k_n(\lambda)$ respectively represent $k(\lambda)$ corresponding to dye 1, dye 2, . . . , dye n, and for example, they are reference dye spectra of each dye which stains the specimen. And $d_1, d_2, \ldots, d_n$ represent virtual thicknesses of the dye 1, dye 2, . . . , dye n at specimen positions on the target specimen S corresponding to each image position of the multiband image. Naturally, dyes are present in a distributive manner in a specimen, so that the concept of thickness is not correct. However the thickness can be a relative indicator representing what amount of dye is contained compared with a case in which the specimen is assumed to be stained with a single dye. In other words, it can be said that $d_1, d_2, \ldots, d_n$ respectively represent dye amounts of the dye 1, dye 2, . . . , dye n. Here, $k_1(\lambda)$, $k_2(\lambda)$, . . . , $k_n(\lambda)$ can be easily obtained from Lambert-Beer law by preparing specimens stained with each dye of dye 1, dye 2, . . . , dye n respectively in advance, and measuring spectral transmission rates thereof by a spectrometer.

When taking the logarithm of both sides of Equation (2), the following Equation (3) is obtained.

$$-\log\frac{I(\lambda)}{I_0(\lambda)} = k_1(\lambda) \cdot d_1 + k_2(\lambda) \cdot d_2 + \ldots + k_n(\lambda) \cdot d_n \tag{3}$$

When an element corresponding to the wavelength $\lambda$ of the estimated spectrum estimated for each pixel of the VS image is defined as $\hat{t}(x, \lambda)$, and this is substituted in the equation (3), the following Equation (4) is obtained.

$$-\log \hat{t}(x,\lambda) = k_1(\lambda) \cdot d_1 + k_2(\lambda) \cdot d_2 + \ldots + k_n(\lambda) \cdot d_n \tag{4}$$

There are n unknown variables $d_1, d_2, \ldots, d_n$ in Equation (4). Hence, when at least n simultaneous Equations (4) are used for at least n different wavelengths $\lambda$, the simultaneous equations can be solved. To further improve accuracy, n or more simultaneous Equations (4) may be used for n or more different wavelengths $\lambda$, and a multiple regression analysis may be performed.

While the procedure of the dye amount calculation has been briefly described, the staining dyes to be calculated in the first embodiment are H dye, E dye, DAB dye, and NF dye, and hence, n=4. The dye amount calculator 457 estimates the dye amount of each of H dye, E dye, DAB dye, and NF dye fixed to a corresponding specimen position on the basis of the estimated spectrum estimated for each pixel of the VS image.

Figure 19:
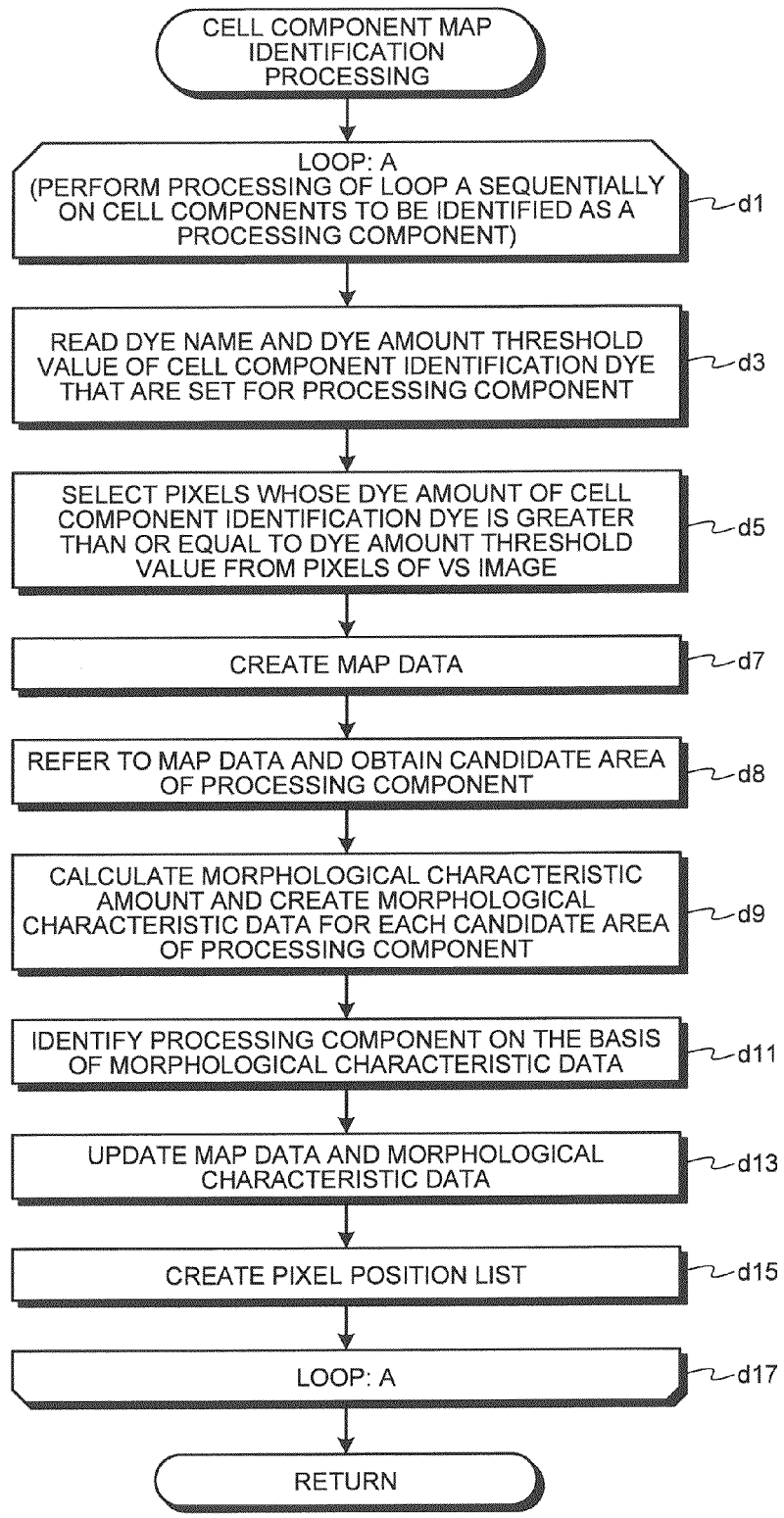
FIG. 19 is a flowchart showing a processing procedure of cell component identification processing.

When the dye amounts of each staining dye are calculated as described above, the dye amount calculator 457 sets and updates identification information indicating the dye amount data in the data type (step c11), and ends the dye amount calculation processing. Then, the process returns to step b5 in FIG. 15, and thereafter the process proceeds to cell component identification processing in step b7. FIG. 19 is a flowchart showing a processing procedure of the cell component identification processing.

In the cell component identification processing, the cell component identification processing unit 458 defines that the cell components for which the dye name and the dye amount threshold value are set in step c7 in FIG. 16 as the cell components to be identified, and performs processing of loop A (step d1 to step d17) for each cell component to be identified. Hereinafter, the cell component to be identified in the loop A is referred to as "processing component". In the first embodiment, the processing of loop A is performed sequentially on the cell nucleus and the cell membrane as the processing components.

Specifically, in the loop A, first, the cell component identification processing unit 458 reads the dye name and the dye amount threshold value of the cell component identification dye that are set for the processing component from the cell component identification staining information 517 (step d3). For example, when processing the cell nucleus as the processing component, the cell component identification processing unit 458 reads the dye name (in the first embodiment, H dye) and the dye amount threshold value thereof from the cell nucleus identification dye information 5171. In a similar manner, when processing the cell membrane as the processing component, the cell component identification processing unit 458 reads the dye name (in the first embodiment, NF dye) and the dye amount threshold value thereof from the cell membrane identification dye information 5172. Although, in the first embodiment, the cytoplasm is not identified, when processing the cytoplasm as the processing component, the cell component identification processing unit 458 reads the dye name and the dye amount threshold value thereof from the cytoplasm identification dye information 5173. As the cytoplasm identification dye, for example, there is E dye that stains cytoplasm, connective tissue, or the like.

Next, the cell component identification processing unit 458 refers to the dye amount data 582 and selects pixels whose dye amount of the cell component identification dye whose dye name is read in step d3 is greater than or equal to the dye amount threshold value read in step d3 from the pixels of the VS image (step d5). Then, the cell component identification processing unit 458 creates map data in which the selection results are set (step d7).

Figures 20, 21:
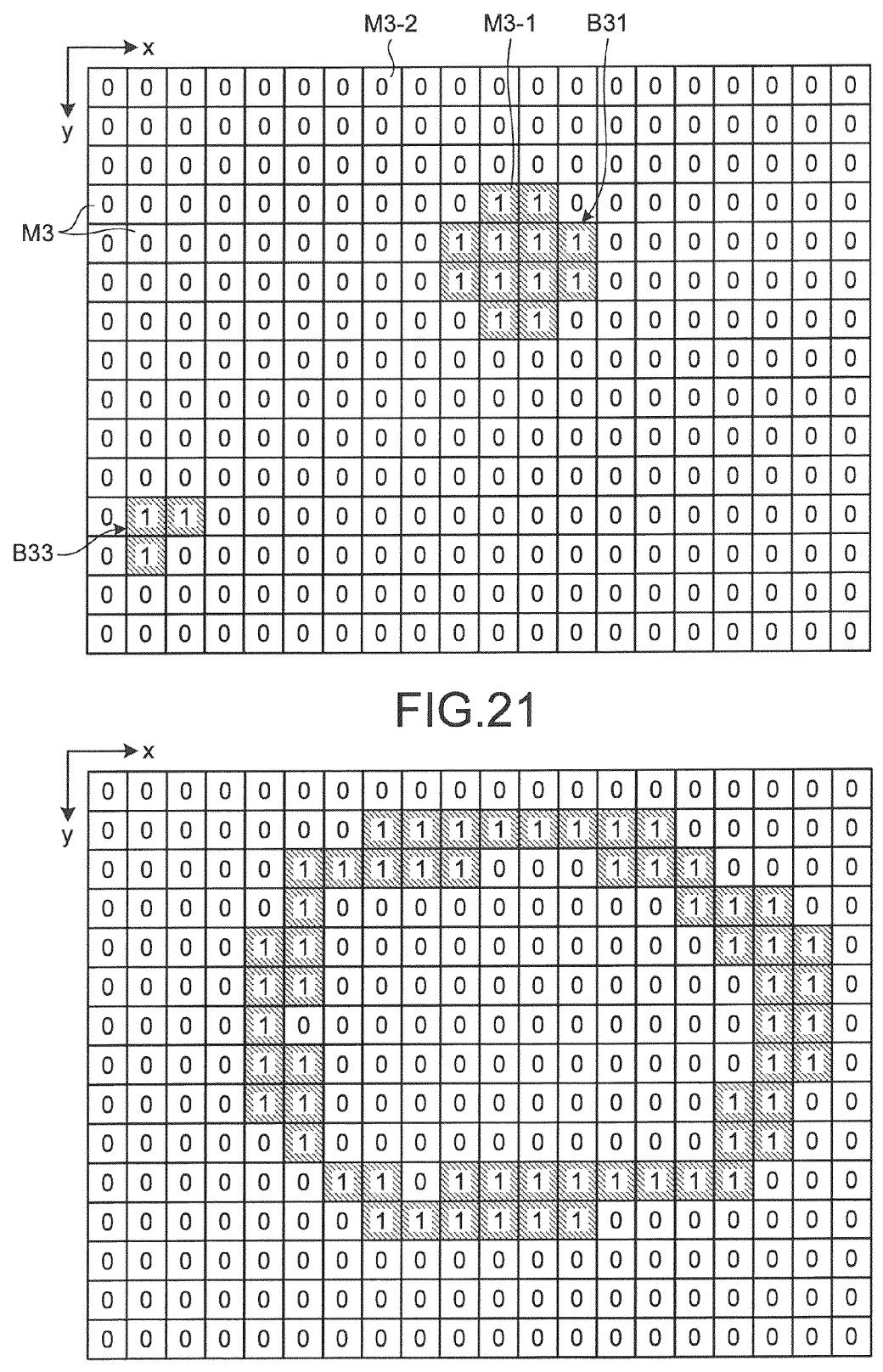

FIG. 20 is a schematic diagram for explaining a data configuration example of the map data of the cell nucleus created as a result of the processing from step d3 to step d7 in FIG. 19 when the cell nucleus is defined as the processing component. As shown in FIG. 20, the map data of the cell nucleus has a data configuration in which "0" or "1" is set in each block M3 corresponding to each pixel position of the pixels constituting the VS image. In FIG. 20, for simplicity, the map data constituted by blocks M3 of 20×15 pixels is illustrated as an example, and "1" is set in the blocks M3 corresponding to the pixels selected in step d5 as shown in the blocks M3-1 for example. "0" is set in the blocks M3 corresponding to pixels that are not selected in step d5 as shown in the blocks M3-2 for example.

On the other hand, FIG. 21 is a schematic diagram for explaining a data configuration example of the map data of the cell membrane created as a result of the processing from step d3 to step d7 in FIG. 19 when the cell membrane is defined as the processing component. As shown in FIG. 21, in a similar manner to the map data of the cell nucleus, the map data of the cell membrane has a data configuration in which "0" or "1" is set in each of a plurality of blocks M3 corresponding to each pixel position of the pixels constituting the VS image. In FIG. 21, in the same manner as in FIG. 20, the map data constituted by blocks of 20×15 pixels is illustrated as an example, and "1" is set in the blocks corresponding to the pixels selected in step d5. "0" is set in the blocks corresponding to pixels that are not selected in step d5.

Although not shown in the figures, also the map data of the cytoplasm created as a result of the processing from step d3 to step d7 in FIG. 19 when the cytoplasm is defined as the processing component has a similar data configuration, and "1" is set in the blocks corresponding to the pixels selected in step d5 among the blocks corresponding to each pixel position of the pixels constituting the VS image. "0" is set in the blocks corresponding to pixels that are not selected in step d5.

Return to FIG. 19. Next, the cell component identification processing unit 458 segments the pixels selected in step d5 into link components by referring to the map data created in step d7, provides a unique label for identifying individual processing component to each segmented pixel group, and thus obtains each of the pixel groups as a candidate area of a processing component (step d8). Next, the cell component identification processing unit 458 creates morphological characteristic data for each candidate area of a processing component obtained in step d8 (step d9). Then, the cell component identification processing unit 458 determines whether or not the candidate area of a processing component is an area of the processing component on the basis of the created morphological characteristic data, and hence identifies the corresponding cell component (step d11). This identification of the cell component can be realized by, for example, applying a publicly known technique described in Japanese Laid-open Patent Publication No. 2009-175334. Thereafter, the cell component identification processing unit 458 modifies and updates the map data and the morphological characteristic data on the basis of the identification result of the processing component (step d13).

Here, processing from step d8 to step d13 when the processing component is cell nucleus, cell membrane, and cytoplasm will be sequentially and briefly described.

When the processing component is the cell nucleus, first, in processing of step d8, the map data of the cell nucleus is referred to, and a candidate area of the cell nucleus (cell nucleus candidate area) is obtained. Specifically, for example, a unique label is attached to pixel (block) groups in which "1" is set continuously, and the pixel groups to which the same label is attached are obtained as one cell nucleus candidate area.

Next, in processing of step d9, for example, first, a publicly known method such as contour tracing is applied, and a contour is extracted from each cell nucleus candidate area. Then, the morphological characteristic amounts showing morphological characteristics are calculated on the basis of the extracted contour of the cell nucleus candidate area, and the calculated morphological characteristic amounts are set to create morphological characteristic data of the cell nucleus.

FIG. 22 is a diagram for explaining a data configuration example of the morphological characteristic data of the cell nucleus. As shown in FIG. 22, as the morphological characteristic amounts of the cell nucleus, for example, there are the circumscribed rectangle, the center of gravity, the area, the boundary length, the degree of circularity, the long axis, the short axis, the aspect ratio, and so forth.

Here, the circumscribed rectangle is a rectangle which circumscribes the cell nucleus candidate area and whose sides are in parallel with the x coordinate axis or the y coordinate axis. For example, the circumscribed rectangle is calculated as the x-coordinate, the y-coordinate, the width in the x direction (the number of pixels in the x direction: W), and the height in the y direction (the number of pixels in the y direction: H) in the VS image whose vertex is upper left corner.

The center of gravity is calculated as the x-coordinate and the y-coordinate in the VS image. The area is the area of the cell nucleus candidate area. The boundary length is calculated as the length of the external contour of the cell nucleus candidate area.

The degree of circularity is calculated according to, for example, the following Equation (5). Here, the value calculated by Equation (5) becomes the maximum value (=1) when the contour shape of the cell nucleus candidate area is a true circle, and the more complex the contour shape is, the smaller the value is.

$$\text{Degree of circularity} = 4\pi \times \text{area}/\text{boundary length} \quad (5)$$

The long axis and the short axis are calculated as the length of the long axis and the length of the short axis when the area of the bounding rectangle circumscribing the cell nucleus candidate area becomes the smallest.

The aspect ratio is a ratio between the long axis and the short axis, and calculated according to, for example, the following Equation (6).

$$\text{Aspect ratio} = \text{long axis}/\text{short axis} \quad (6)$$

The cell component identification processing unit 458 associates the values of the morphological characteristic amounts with the labels assigned to the cell nucleus candidate area, and creates the morphological characteristic data. For example, in the example of FIG. 20, different labels are attached to two pixel groups 331 and 333 respectively, and each of the pixel groups 331 and 333 is obtained as a cell nucleus candidate area. The morphological characteristic data is calculated for each of the two cell nucleus candidate areas, and two records of the morphological characteristic data are created.

Next, in processing of step d11, it is determined whether or not the cell nucleus candidate area is an area of the cell nucleus on the basis of the created morphological characteristic data. Generally, it is said that the size of the cell nucleus is around 10 μm. Therefore, in the first embodiment, for example, when the values of the morphological characteristic amounts match the size, the cell nucleus candidate area is determined to be the area of the cell nucleus, and when the values do not match the size, the cell nucleus candidate area is determined not to be the area of the cell nucleus. Here, the actual size of one pixel of the VS image can be obtained from the size of one pixel (assumed to be square pixel) of the TV camera 32 and the observation magnification, so that conversion from the number of pixels to the actual size can be easily performed. It is also possible to set standard values of the morphological characteristic amounts of the cell nucleus appearing in the VS image as reference values in advanced and determine whether or not the cell nucleus candidate area is an area of the cell nucleus by comparison with the standard values.

Next, in processing of step d13, the map data of the cell nucleus is modified on the basis of the cell nucleus candidate area that is determined not to be the area of the cell nucleus, the morphological characteristic data of the cell nucleus candidate area is deleted, and the map data of the cell nucleus and the morphological characteristic data are updated. For example, it is assumed that, among the pixel groups B31 and B33 shown in FIG. 20, the cell nucleus candidate area of the pixel group B31 is determined to be the area of the cell nucleus, the cell nucleus candidate area of the pixel group B33 is determined not to be the area of the cell nucleus, and only the cell nucleus candidate area of the pixel group B31 is identified as the cell nucleus. In this case, the map data is updated by modifying the value of each pixel (block) constituting the pixel group B33 in FIG. 20 from "1" to "0". Then, the morphological characteristic data is updated by deleting the morphological characteristic data created in step d9 in FIG. 19 and one record of the morphological characteristic data in which the label of the cell nucleus candidate area of the pixel group B33 is set.

Next, a case in which the processing component is the cell membrane will be described. Although identification of the cell membrane is performed by a processing procedure similar to that of the case in which the processing component is the cell nucleus, when the processing component is the cell membrane, in step d9 in FIG. 19, for example, the circumscribed rectangle, the center of gravity, the thickness, the boundary length, the degree of circularity, the long axis, the short axis, the aspect ratio, the presence or absence of nucleus (the number of nuclei), and so forth are calculated as the morphological characteristic amounts, and the morphological characteristic data is created. FIG. 23 is a diagram for explaining a data configuration example of the morphological characteristic data of the cell membrane. Here, the cell membrane forms the outermost layer of the cell, and has a predetermined thickness. The thickness calculated as the morphological characteristic amount of the cell membrane corresponds to the width in the radial direction of the cell membrane candidate area. The circumscribed rectangle, the center of gravity, the boundary length, the degree of circularity, the long axis, the short axis, and the aspect ratio are calculated on the basis of, for example, the outer contour. The calculation method is the same as that in the case of the cell nucleus. In the presence or absence of nucleus, information indicating whether or not an area of the cell nucleus is included inside the cell membrane candidate area (or the number of the areas of the cell nucleus) is set. The presence or absence of nucleus (the number of nuclei) can be set by referring to the map data of the cell nucleus created by the method described above when the cell nucleus is included as a cell component to be identified. Specifically, when an area of the cell nucleus is included inside the cell membrane candidate area, "presence (or the number of nuclei)" is set, and when the area is not included, "absence" is set.

For example, a standard thickness range of the cell membrane is set in advance. When a thickness value calculated as one of the morphological characteristic amounts is within the range, the cell membrane candidate area is determined to be an area of the cell membrane, and when the thickness value is not within the range, the cell membrane candidate area is determined not to be an area of the cell membrane. Or, a standard size range of the cell is set in advance. When the values of the morphological characteristic amounts match the size, the cell membrane candidate area may be determined to be an area of the cell membrane, and when the values do not match the size, the cell membrane candidate area may be determined not to be an area of the cell membrane. When the cell component to be identified includes the cell nucleus, and the presence or absence of nucleus as the morphological characteristic amount is known, the cell membrane candidate area may be determined to be an area of the cell membrane when "presence" is set, and the cell membrane candidate area may be determined not to be an area of the cell membrane when "absence" is set.

Next, a case in which the processing component is the cytoplasm will be described. Although identification of the cytoplasm is performed by a processing procedure similar to that of the case in which the processing component is the cell nucleus or the cell membrane, when the processing component is the cytoplasm, in step d9 in FIG. 19, for example, the circumscribed rectangle, the center of gravity, the area, the boundary length, the degree of circularity, the long axis, the short axis, the aspect ratio, the presence or absence of nucleus (the number of nuclei), and so forth are calculated as the morphological characteristic amounts, and the morphological characteristic data is created. Here, the cytoplasm forms an area inside the cell membrane and except for the area of the cell nucleus. Therefore, the values of the morphological characteristic amounts are calculated on the basis of, for example, the outer contour. The calculation method is the same as that in the case of the cell nucleus or the cell membrane.

For example, the area of the cytoplasm is determined by referring to the map data of the cell nucleus and/or the map data of the cell membrane created by the methods described above. This determination method assumes that at least the cell nucleus or the cell membrane is included as a cell component to be identified. Specifically, when the area of the cell membrane is present outside the cytoplasm candidate area, the cytoplasm candidate area is determined to be the area of the cytoplasm, and when the area of the cell membrane is not present outside the cytoplasm candidate area, the cytoplasm candidate area is determined not to be the area of the cytoplasm. Or, when the area of the cell nucleus is present inside the cytoplasm candidate area, the cytoplasm candidate area is determined to be the area of the cytoplasm, and when the area of the cell nucleus is not present inside the cytoplasm candidate area, the cytoplasm candidate area is determined not to be the area of the cytoplasm. Or, when the area of the cell membrane is present outside the cytoplasm candidate area and the area of the cell nucleus is present inside the cytoplasm candidate area, the cytoplasm candidate area may be determined to be the area of the cytoplasm.

Return to FIG. 19. Next, the target portion extraction unit 460 creates a list (pixel position list) of position coordinates of the pixels for which "1" is set in the map data for each assigned label (step d15), and ends the processing of loop A for the processing component.

After the processing of loop A is performed using all the cell components to be identified as the processing component, the cell component identification processing is completed, and the process returns to step b7 in FIG. 15, and then proceeds to step b9.

Figure 24:
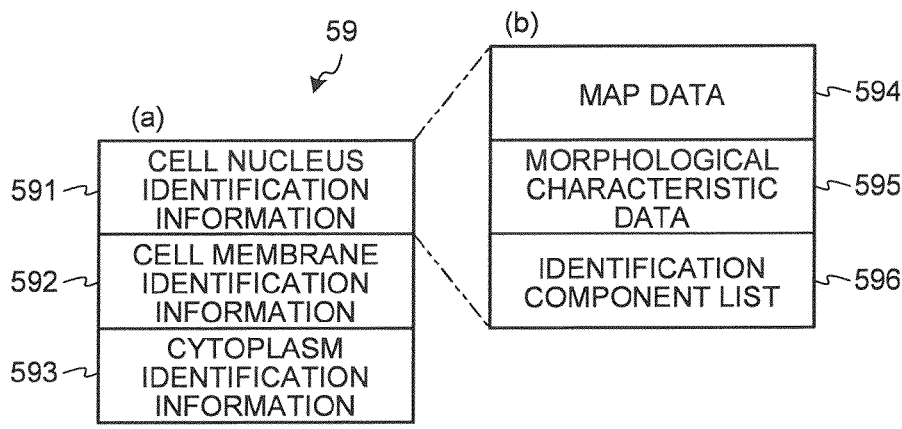
FIG. 24 is a diagram for explaining a data configuration example of identification component information.

FIG. 24 is a diagram for explaining a data configuration example of the identification component information 59 (refer to (b) of FIG. 14) that is obtained as a result of the cell component identification processing and set in the VS image file 5. As shown in (a) of FIG. 24, the identification component information 59 includes cell nucleus identification information 591, cell membrane identification information 592, and cytoplasm identification information 593. The cell nucleus identification information 591, the cell membrane identification information 592, and the cytoplasm identification information 593 have the same data configuration, and, as shown in (b) of FIG. 24, include map data 594, morphological characteristic data 595, and an identification component list 596.

Figure 25:
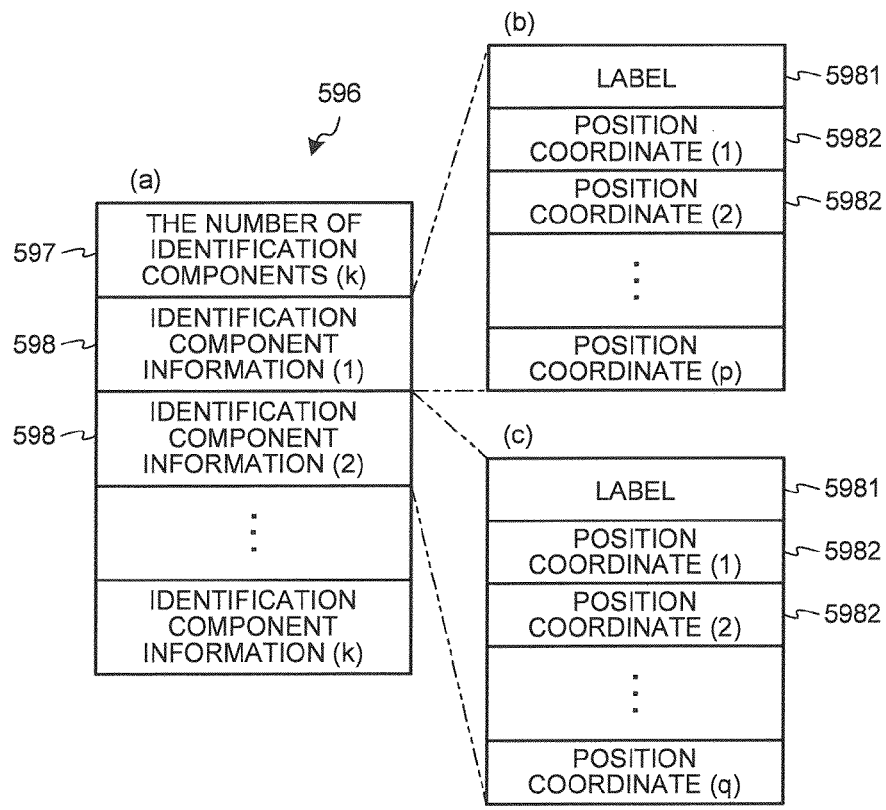
FIG. 25 is a diagram for explaining a data configuration example of an identification component list.

FIG. 25 is a diagram for explaining a data configuration example of the identification component list 596. As shown in (a) of FIG. 25, the identification component list 596 includes the number of identification components 597 and identification component information (1) to (k) 598, the number of which corresponds to the number of identification components 597.

In the number of identification components 597, the number of identified cell components is set. For example, the number of areas identified as an area of the cell nucleus is set in the number of identification components 597 set in the identification component list 596 of the cell nucleus identification information 591. Information related to area of each cell nucleus is set in the identification component information (1) to (k) 598. Specifically, as shown in (b) and (c) of FIG. 25, a label 5981 attached to the area of the cell nucleus and position coordinates (1) to (p)/(1) to (q) 5982 which are the pixel position list in the area of the cell nucleus are set in the identification component information (1) to (k) 598.

For example, in the first embodiment, as the cell nucleus identification information 591, the map data 594 of the cell nucleus and the morphological characteristic data 595 of the cell nucleus that are created in step d7 and step d9 and modified and updated in step d13 are set. In the identification component list 596, the number of areas of the cell nucleus is set as the number of identification components 597. In each of the identification component information (1) to (k) 598, the label 5981 attached to a corresponding area of the cell nucleus is set, and the pixel position list of the cell nucleus created in step d15 is set as the position coordinates (1) to (p)/(1) to (q) 5982. In the same way, as the cell membrane identification information 592, the map data 594 of the cell membrane and the morphological characteristic data 595 of the cell membrane that are created in step d7 and step d9 and modified and updated in step d13 are set. In the identification component list 596, the number of areas of the cell membrane is set as the number of identification components 597. In each of the identification component information (1) to (k) 598, the label 5981 attached to a corresponding area of the cell membrane is set, and the pixel position list of the cell membrane created in step d15 is set as the position coordinates (1) to (p)/(1) to (q) 5982. Since the cell nucleus and the cell membrane are identified in the first embodiment, no value is set in the cytoplasm identification information 593.

Figure 26:
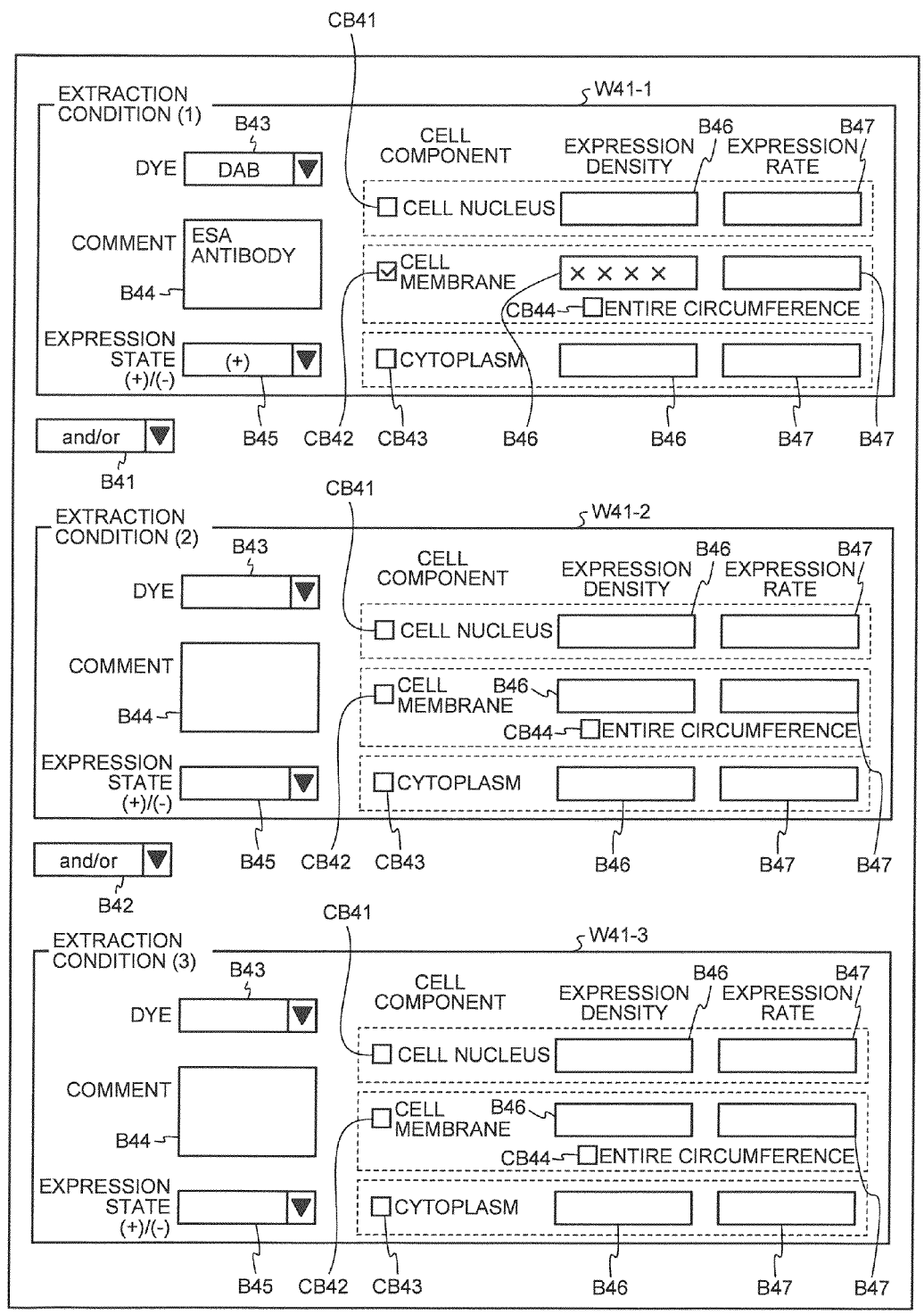
FIG. 26 is a diagram showing an example of an extraction condition setting screen.

Return to FIG. 15. In the next step b9, the extraction condition setting unit 459 performs processing for displaying a notification of a setting request of an extraction condition for extracting the target portion on the display unit 43. For example, the extraction condition setting unit 459 performs processing for displaying an extraction condition setting screen on the display unit 43 to notify the setting request of the extraction condition, and receives a setting operation of the extraction condition by a user on the extraction condition setting screen. FIG. 26 is a diagram showing an example of the extraction condition setting screen.

As shown in FIG. 26, the extraction condition setting screen includes a plurality of target portion setting screens W41 (three target portion setting screens W41-1 to W41-3) that are configured in the same way, and spin boxes B41 and B42 that prompt to select AND condition or OR condition are disposed between the target portion setting screens W41. The user sets an expression state (presence or absence of expression) of the target molecule in the target portion setting screen W41. When setting an extraction condition in which a plurality of expression states of target molecules are combined, the user sets an extraction condition individually on the plurality of target portion setting screens W41, and selects the AND condition or the OR condition between the extraction conditions set on the target portion setting screens W41 by using the spin boxes B41 and B42. The number of the target portion setting screens W41 may be one or more. It is possible to realize a screen configuration on which an extraction condition in which expression states of one or more target molecules are combined can be set.

The target portion setting screen W41 includes a spin box B43 for selecting a dye (molecule target dye) of the molecule target staining performed on the target specimen S to label the target molecule. A comment display field B44 is disposed under the spin box B43.

The spin box B43 displays a list of the molecule target dyes set as the staining dye in step c3 in FIG. 16 as options, and prompts to select one of the molecule target dyes. In the first embodiment, DAB dye and NF dye are displayed as options. By using the spin box B43, the user sets the staining dye that is the molecule target dye for labeling the target molecule among the staining dyes that stain the target specimen S. When the molecule target dyes set as the staining dye includes the cell component identification dye, it is possible to employ a configuration in which the cell component identification dye is removed from the options and the options are displayed. In this configuration, in the first embodiment, only DAB dye is displayed as the option. In this way, user operability improves.

In the comment display field B44, comment information such as names of the antibody and the antigen (target molecule) inputted on the dye registration screen (refer to FIG. 17) described above with respect to the molecule target dye selected in the spin box B43 is displayed. Therefore, even when a plurality of different molecule target stainings are performed on the target specimen to be observed and diagnosed, and different target molecules are labeled, the user can select a molecule target dye for labeling a desired target molecule in the corresponding spin box B43 while referring to the comment display field B44.

The target portion setting screen W41 includes a spin box B45 for selecting an expression state of the target molecule. When extracting a portion where the target molecule is expressed, in other words, a portion which is stained by the selected molecule target dye, as the target portion, "expression is present" (+) is selected in the spin box B45. On the other hand, when extracting a portion where the target molecule is not expressed, in other words, a portion which is not stained by the selected molecule target dye, as the target portion, "expression is absent" (−) is selected in the spin box B45.

The target portion setting screen W41 includes three checkboxes CB41, CB42, and CB43 for selecting the cell component in which the target molecule is present, and two input boxes B46 and B47 are arranged for each of the three checkboxes CB41, CB42, and CB43.

The checkboxes CB41, CB42, and CB43 are used to respectively select the cell nucleus, the cell membrane, and the cytoplasm, which are the cell components. Two or more of the checkboxes CB41, CB42, and CB43 can be checked. When extracting a portion where the same target molecule is expressed on the cell membrane and on the cytoplasm located inside the cell membrane as the target portion, the checkbox CB42 and the checkbox CB43 are checked.

The cell components that can be set by checking the checkboxes CB41, CB42, and CB43 are limited to the cell components that are identified in the cell component identification processing shown and described in FIG. 19. Therefore, it is possible to employ a configuration in which the checkbox for the cell component that is not identified cannot be selected. In this way, user operability improves.

The input box B46 is used to set expression density corresponding to a presence density of the target molecule on the corresponding cell component as an extraction condition. The expression density is used as a criterion to determine whether or not the target molecule expresses the expression density when the target portion is extracted in step b13 in FIG. 15 described below. For example, the user inputs a value of the dye amount of the selected molecule target dye as the expression density of the target molecule into the input box B46. Based on this, among the pixels in the area of the corresponding cell component, pixels where the dye amount of the selected molecule target dye is greater than or equal to a value of desired dye amount can be extracted as pixels where the target molecule is expressed. Or, among the pixels in the area of the corresponding cell component, pixels where the dye amount of the selected molecule target dye is smaller than a value of desired dye amount can be extracted as pixels where the target molecule is not expressed.

When observing and diagnosing the target molecule present in the target specimen S, not only the cell component on which the target molecule is present, but also the expression density of the target molecule may be important. For example, even a target molecule present on a predetermined cell component may be a problem when the expression density is high, and may not be a problem when the expression density is low. The opposite is true. In such cases, the user inputs the range of the dye amount of the selected molecule target dye as the expression density of the target molecule into the input box B46. In this way, an area where the target molecule is expressed at desired density on the corresponding cell component (specifically, among the pixels in the area of the corresponding cell component, pixels where the dye amount of the selected molecule target dye is within the range of the dye amount inputted into the input box B46) can be extracted as the target portion. When simply extracting pixels that include the dye amount of the molecule target dye or extracting pixels that do not include the dye amount of the molecule target dye, no value is inputted into the input box B46. The expression density can be set for each cell component.

The input box B47 is used to set an expression rate corresponding to a presence rate of the target molecule on the corresponding cell component as an extraction condition. When observing and diagnosing the target molecule present in the target specimen S, not only the expression density described above, but also the rate by which the target molecules occupy areas on a predetermined cell component may be important. In such a case, the user inputs a value of the expression rate of the target molecule on the cell component into the input box B47. For example, when setting an extraction condition that the target molecule is expressed in an area of 10% or more of the area in the cell membrane, the checkbox CB42 of the cell membrane is checked and "10% or more" is inputted into the corresponding input box B47.

Under the input box B47, a checkbox CB44 for setting an extraction condition that the target molecules are present on an approximately entire area (entire circumference) of the cell membrane is disposed. For example, in an HER2 protein test performed for Herceptin (registered trademark) treatment against breast cancer, it is necessary to determine whether or not HER2 receptors are present on the entire circumference of the cell membrane. In such a case, the checkbox CB44 is checked. When actually extracting the target portion, if the checkbox CB44 is checked, the extraction can be realized by a procedure in which pixels in an area where the target molecule is expressed at an expression rate greater than or equal to a predetermined expression rate (for example, 80%) in the cell membrane are extracted as the target portion.

The expression rate can be set for each cell component in the same manner as for the expression density. Here, for example, there is a case in which the target molecules that are strongly expressed on the cell membrane and moderately or strongly expressed on the cytoplasm are desired to be extracted as the target portion. In such a case, the checkbox CB42 of the cell membrane is checked, a value of the dye amount corresponding to the strong expression is inputted into the corresponding input box B46, and a value of the expression rate (for example, 80% or more) corresponding to the strong expression is inputted into the corresponding input box B47. Further, the checkbox CB43 of the cytoplasm is checked, a value of the dye amount corresponding to the moderate or strong expression is inputted into the corresponding input box B46, and a value of the expression rate (for example, 50% or more) corresponding to the moderate or strong expression is inputted into the corresponding input box B47, so that the target portion as described above can be extracted.

It is possible to employ a configuration in which, when the "expression is present" (+) is selected in the spin box B45, the input box B47 accepts a value input, and when the "expression is absent" (−) is selected, the input box B47 does not accept a value input. When simply extracting the target molecule expressed on the cell component, no value is inputted into the input box B47.

On the extraction condition setting screen configured as described above, the user sets the extraction condition by selecting the molecule target dye for labeling the target molecule and the presence or absence of expression of the target molecule, selecting the cell component in which the target molecule is present, and inputting the expression density and the expression rate on the selected cell component as necessary. As described above, the target specimen S to be observed and diagnosed in the first embodiment is a specimen obtained by labeling the specimen by coloring of the DAB reaction using the EGFR antibody that recognizes the EGFR receptor. In the first embodiment, the example is described in which a portion where the EGFR receptor is expressed on the cell membrane in the target specimen S is extracted as the target portion. In this case, the DAB dye is selected in the spin box B43 in the target portion setting screen W41-1, and the "expression is present" (+) is selected in the spin box B45. The checkbox CB42 is checked to select the cell membrane, and the value of the dye amount of the DAB dye for determining that the target molecule is present is inputted into the input box B46. The value of the expression rate is inputted into the input box B47 if necessary.

The extraction condition setting screen does not prevent a case where the same molecule target dye is selected in the spin box B43 in different target portion setting screens W41. For example, there is a case in which the target molecule that is expressed on the cell membrane and is not expressed on the cytoplasm is desired to be extracted as the target portion. In this case, the molecule target dye for labeling the target molecule is selected in the spin box B43 in the target portion setting screen W41-1 and the "expression is present" (+) is selected in the spin box B45, and further the same molecule target dye is selected in the spin box B43 in the target portion setting screen W41-2 and the "expression is absent" (−) is selected in the spin box B45. Then, the AND condition is selected in the spin box B41 for setting the AND/OR condition between the target portion setting screen W41-1 and the target portion setting screen W41-2.

The extraction condition is not limited to the exemplified expression density and expression rate. For example, the extraction condition may be set with respect to the morphology of the cell component. Specifically, the morphological characteristic amounts of the cell components checked in the checkboxes CB41, CB42, and/or CB43 may be set as the extraction condition. As described above, the morphological characteristic amounts are the circumscribed rectangle, the center of gravity, the area, the boundary length, the degree of circularity, the long axis, the short axis, the aspect ratio, the thickness, the presence or absence of nucleus (the number of nuclei), and so forth. As an example set in the morphological characteristic data 595, an input box of the degree of circularity is disposed as an input box corresponding to the checkbox CB42 of the cell membrane, and the degree of circularity may be inputted into the input box. Based on this, it is possible to extract the target molecule expressed on the cell membrane whose degree of circularity is a desired degree of circularity among the cell membranes identified in step d11 in FIG. 19 as the target portion.

Return to FIG. 15. The extraction condition setting unit 459 sets the extraction condition on the basis of the information manually inputted by the user on the extraction condition setting screen as described above (step b11). In the first embodiment, the extraction condition is set in which the molecule target dye is the DAB dye, the expression state is the "expression is present" (+), the cell component is the cell membrane, and the expression density on the cell membrane is an input value. When there is an input into the input box B47 in FIG. 26, the extraction condition may be set by using the input value as the expression rate on the cell membrane.

The target portion extraction unit 460 performs processing to extract the target portion (target portion extraction processing) according to the extraction condition set in step b11, and creates a target portion map (step b13).

Here, the principle of the target portion extraction processing will be described. In the target portion extraction processing, first, the target portion extraction unit 460 reads the map data 594 of the set cell component according to the extraction condition.

Next, the target portion extraction unit 460 creates an expression state map on the basis of the dye amount of the set molecule target dye according to the extraction condition. Specifically, when the "expression is present" (+) is set, a pixel where the dye amount of the set molecule target dye is included and the value of the dye amount is greater than or equal to the set value of the expression density is selected as a target portion candidate pixel. Or, a pixel where the dye amount of the set molecule target dye is included and the value of the dye amount is within the set range of the expression density is selected as the target portion candidate pixel. When the expression density is not set, a pixel where the dye amount of the set molecule target dye is included may be selected as the target portion candidate pixel. Then, the expression state map is created in which "1" is set at the position of the selected pixel.

On the other hand, when the "expression is absent" (−) is set, a pixel where the dye amount of the set molecule target dye is not included or the value of the dye amount is smaller than the set value of the expression density is selected as the target portion candidate pixel. When the expression density is not set, a pixel where the dye amount of the set molecule target dye is not included may be selected as the target portion candidate pixel. Then, the expression state map is created in which "1" is set at the position of the selected pixel.

Then, among the pixels to which "1" is set in the map data 594 of the set cell component, the target portion candidate pixels where "1" is set in the expression state map are extracted as the pixels of the area of the target portion, and the target portion map is created. Here, when the expression rate is set as the extraction condition, the expression rate is calculated for each cell component to which the same label is attached. Specifically, the cell components to which the same label is attached are to be processed sequentially, and the rate of the number of the target portion candidate pixels in the area of the cell component to be processed is obtained on the basis of the number of the pixels in the area of the cell component to be processed, so that the expression rate in the cell component to be processed is obtained. The expression rate may be obtained by using the expressing density. Specifically, among the target portion candidate pixels in the area of the cell component to be processed, the number of pixels where the expression density thereof is greater than or equal to a predetermined expression density set in advance (the value of the dye amount is greater than or equal to a predetermined value set in advance) may be counted. Then, the expression rate may be obtained by calculating the rate of the counted number to the number of pixels in the area of the cell component to be processed. When the value of the calculated expression rate is greater than or equal to the set value of the expression rate, the target portion candidate pixels in the area of the cell component to be processed are extracted as the pixels of the area of the target portion.

Figure 27:
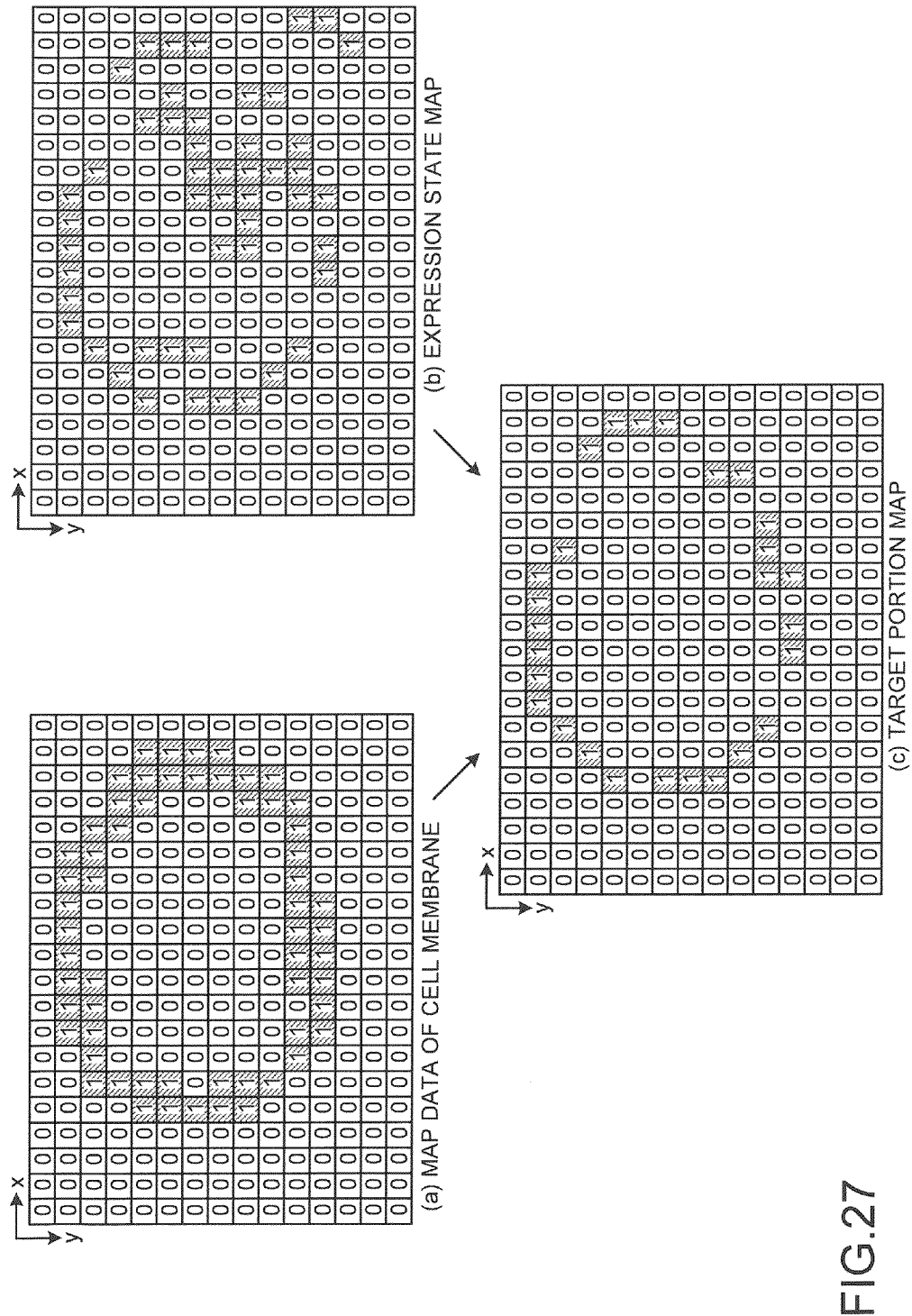
FIG. 27 illustrates a principle of target portion extraction processing according to the first embodiment.

FIG. 27 illustrates the principle of the target portion extraction processing according to the first embodiment. (a) of FIG. 27 shows an example of the map data 594 of the cell membrane, (b) of FIG. 27 shows an example of the expression state map, and (c) of FIG. 27 shows an example of the target portion map. In the same manner as in FIG. 20 or the like, (a) to (c) of FIG. 27 illustrate the map data, the expression state map, and the target portion map which are constituted by 20×15 blocks.

In the first embodiment, first, the map data 594 of the cell membrane shown in (a) of FIG. 27 is read. Next, as shown in (b) of FIG. 27, the target portion candidate pixels where the dye amount of the DAB dye is included and the value of the dye amount is greater than or equal to the set value of the expression density are selected from the pixels of the VS image, and the expression state map in which "1" is set to the selected target portion candidate pixels is created. Then, as shown in (c) of FIG. 27, among the pixels to which "1" is set in the map data 594 of the cell membrane, the target portion candidate pixels where "1" is set in the expression state map are extracted as the pixels of the area of the target portion.

So far, the principle of the target portion extraction processing has been described. However, in the actual target portion extraction processing, the target portion is extracted for each individual cell component to which the same label is attached. Specifically, when a target portion candidate pixel is included an area of one cell component, the cell component is defined as a cell component that includes the target portion (hereinafter referred to as "positive cell component"), and the target portion candidate pixel is extracted as the pixel of the area of the target portion. For example, when the set cell component is the cell membrane, the cell membrane identification information 592 (refer to FIG. 24) is referred to. Then, the pixels of the area of the target portion are extracted depending on whether or not each of the pixels at the position coordinates (1) to (p)/(1) to (q) 5982 is selected as the target portion candidate pixel for each identification component information (1) to (k) 598 (refer to FIG. 25) set in the identification component list 596.

Figure 28:
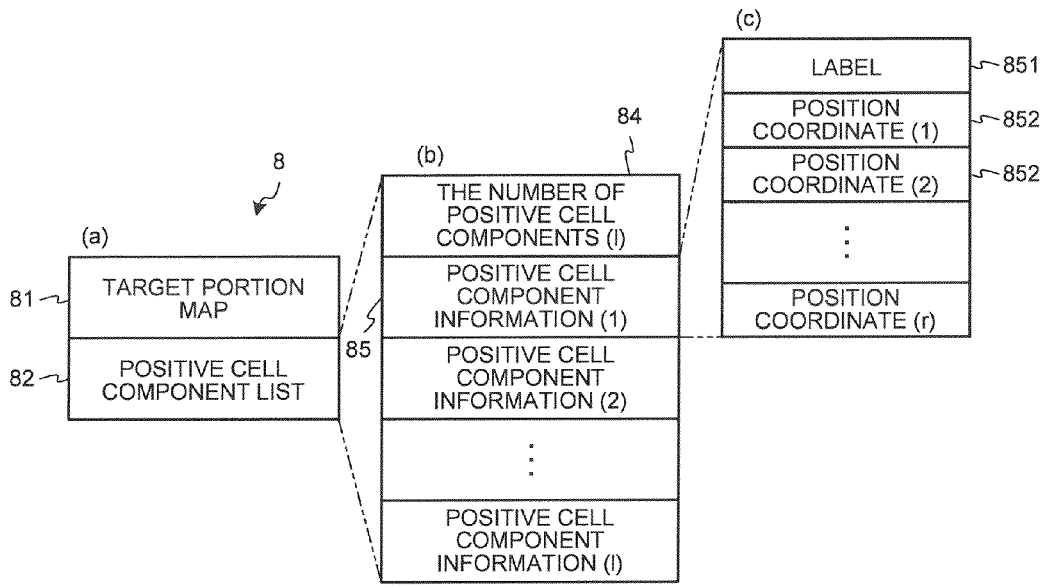
FIG. 28 is a diagram for explaining a data configuration example of target portion information.

Data of the target portion map created as described above is recorded in the recording unit 47 as the target portion information. FIG. 28 is a diagram for explaining a data configuration example of target portion information 8. As shown in (a) of FIG. 28, the target portion information 8 includes target portion map 81 and positive cell component list 82.

As shown in (a) of FIG. 28, the positive cell component list 82 includes the number of positive cell components 84 and positive cell component information (1) to (l) 85, the number of which corresponds to the number of positive cell components 84.

In the number of positive cell components 84, the number of cell components (positive cell components) that includes the target portion is set. Information related to each positive cell component is set in the positive cell component information (1) to (l) 85. Specifically, as shown in (c) of FIG. 28, a label 851 attached to the area of the positive cell component and position coordinates (1) to (r) 852 which are the pixel position list of the target portion in the area of the positive cell component are set in the positive cell component information (1) to (l) 85.

There is a case in which a plurality of cell components are set in one extraction condition and the expression density and the expression rate thereof are also set. A specific example is, as described above, a case in which a portion where the same target molecule is expressed on the cell membrane and on the cytoplasm located inside the cell membrane is extracted as the target portion. In this case, the target portion map is created for each set cell component, and then a target portion map in which the created target portion maps for each cell component are combined together is created.

Figure 29:
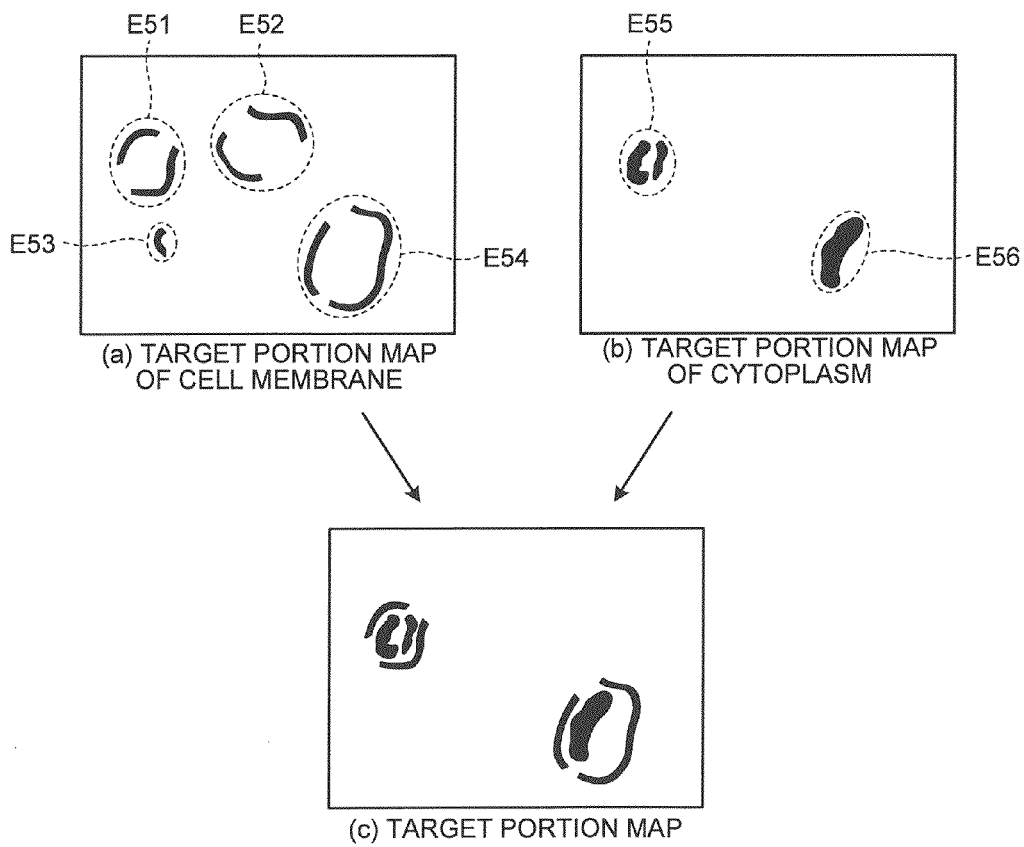
FIG. 29 illustrates a specific procedure of the target portion extraction processing according to a modified example.

Here, a procedure of the target portion extraction processing will be described using an example in which the cell nucleus and the cytoplasm are set and the expression density and the expression rate with respect to each cell component are set. It is assumed that "expression is present" (+) is set as the expression state. FIG. 29 illustrates a specific procedure of the target portion extraction processing in this case, (a) of FIG. 29 shows an example of the target portion map created for the cell membrane, (b) of FIG. 29 shows an example of the target portion map created for the cytoplasm, and (c) of FIG. 29 shows an example of the target portion map in which these two target portion maps are combined together. In (a) to (c) of FIG. 29, pixel positions to which "1" is set are shown as black blocks.

First, the target portion map of the cell membrane is created on the basis of the dye amount of the set molecule target dye in accordance with the expression density and the expression rate set for the cell membrane. The procedure for creating this target portion map is the same as the procedure described above. Based on this, as shown in (a) of FIG. 29, the target portion map of the cell membrane is created in which portions where the target molecule is expressed on the cell membrane and the condition of the expression density and the expression rate thereof is satisfied are set.

In the same way, the target portion map of the cytoplasm is created on the basis of the dye amount of the set molecule target dye in accordance with the expression density and the expression rate set for the cytoplasm. Based on this, as shown in (b) of FIG. 29, the target portion map of the cytoplasm is created in which portions where the target molecule is expressed on the cytoplasm and the condition of the expression density and the expression rate thereof is satisfied are set.

Next, the created target portion map of the cell membrane and the created target portion map of the cytoplasm are combined together, and whether or not the extraction condition is satisfied is determined for each cell. Here, when observing a certain cell, the cytoplasm is located inside the cell membrane. Therefore, the pixels to which "1" is set in the target portion map of the cell membrane are processed for each pixel group constituting the same cell membrane to which the same label is attached, and whether or not the target molecule is expressed inside the pixels is determined.

For example, in (a) of FIG. 29, it is assumed that four areas E51 to E54 enclosed by dashed lines show portions where the target molecule is expressed on different cell membranes to which a label different from each other is attached. On the other hand, in (b) of FIG. 29, it is assumed that two areas E55 and E56 enclosed by dashed lines show portions where the target molecule is expressed on different cytoplasms to which a label different from each other is attached. In the examples of (a) and (b) of FIG. 29, the target molecule expression portion E55 on the cytoplasm shown in (b) of FIG. 29 is located inside the target molecule expression portion E51 on the cell membrane shown in (a) of FIG. 29. In the same way, the target molecule expression portion E56 on the cytoplasm shown in (b) of FIG. 29 is located inside the target molecule expression portion E54 on the cell membrane shown in (a) of FIG. 29. In this case, the expression portion E51 on the cell membrane and the expression portion E55 on the cytoplasm are extracted as the target portion, and the expression portion E54 on the cell membrane and the expression portion E56 on the cytoplasm are extracted as the target portion, and thus, as shown in (c) of FIG. 29, the target portion map is created. The expression portion E52 on the cell membrane and the expression portion E53 on the cell membrane are not extracted as the target portion.

As described above, there is a case in which a plurality of extraction conditions are set on the extraction condition setting screen of FIG. 26 and the AND condition or the OR condition is set between the extraction conditions. In this case, the target portion map is created for each extraction condition, and then a target portion map in which the created target portion maps for each extraction condition are combined together is created.

Figure 30:
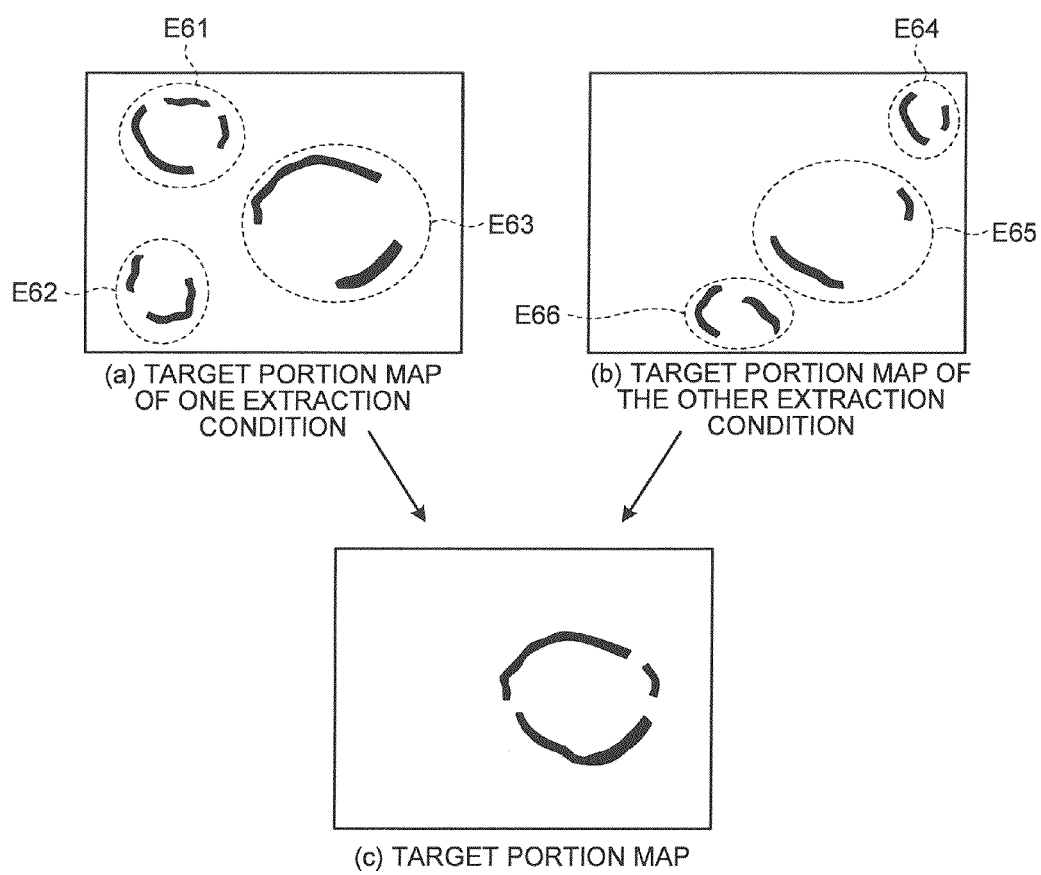
FIG. 30 illustrates a specific procedure of the target portion extraction processing according to another modified example.

Here, the target portion extraction processing will be described using an example in which two extraction conditions are set which are, for example, an extraction condition that a portion where a target molecule α is expressed on the cell membrane is the target portion and an extraction condition that a portion where a target molecule β is expressed on the cell membrane is the target portion, and the AND condition is set between them. FIG. 30 illustrates a specific procedure of the target portion extraction processing in this case, (a) of FIG. 30 shows an example of the target portion map created for one extraction condition, (b) of FIG. 30 shows an example of the target portion map created for the other extraction condition, and (c) of FIG. 30 shows an example of the target portion map in which these two target portion maps are combined together. In (a) to (c) of FIG. 30, pixel positions to which "1" is set are shown as black areas.

First, the target portion map is created in accordance with one extraction condition. The procedure for creating the target portion map with respect to one extraction condition is the same as the procedure described above. Based on this, as shown in (a) of FIG. 30, the target portion map with respect to one extraction condition that sets the expression portion of the target molecule α on the cell membrane is created.

In the same way, the target portion map is created in accordance with the other extraction condition. Based on this, as shown in (b) of FIG. 30, the target portion map with respect to the other extraction condition that sets the expression portion of the target molecule β on the cell membrane is created.

Thereafter, the created target portion maps with respect to the extraction conditions are combined together, and a combined target portion map is created. In this example, the AND condition is set, so that it is necessary to determine whether or not the extraction condition is satisfied for each cell. Specifically, for example, the pixels to which "1" is set in the target portion map of one extraction condition are processed for each pixel group constituting the same cell membrane to which the same label is attached, and whether or not pixels constituting the same cell membrane to which the same label is attached are included in the pixels to which "1" is set in the target portion map of the other extraction condition is determined.

For example, in (a) of FIG. 30, it is assumed that three areas E61 to E63 enclosed by dashed lines show portions where the target molecule α is expressed on different cell membranes to which a label different from each other is attached. On the other hand, in (b) of FIG. 30, it is assumed that three areas E64 and E66 enclosed by dashed lines show portions where the target molecule is expressed on different cell membranes to which a label different from each other is attached. It is assumed that the expression portion E63 in (a) of FIG. 30 and the expression portion E65 in (b) of FIG. 30 are pixels constituting the same cell membrane to which the same label is attached. In this case, the expression portions E63 and E65 on the same cell membrane are extracted as the target portion, and as shown in (c) of FIG. 30, the target portion map is created. The expression portions E61, E62, E64, and E66 on the cell membrane are not extracted as the target portion.

When the OR condition is set, pixels to which "1" is set in either one of the target portion maps, which are the target portion map of one extraction condition shown in (a) of FIG. 30 and the target portion map of the other extraction condition shown in (b) of FIG. 30, are extracted as the area of the target portion, and a target portion map in which "1" is set to each extracted pixel is created.

Figure 31:
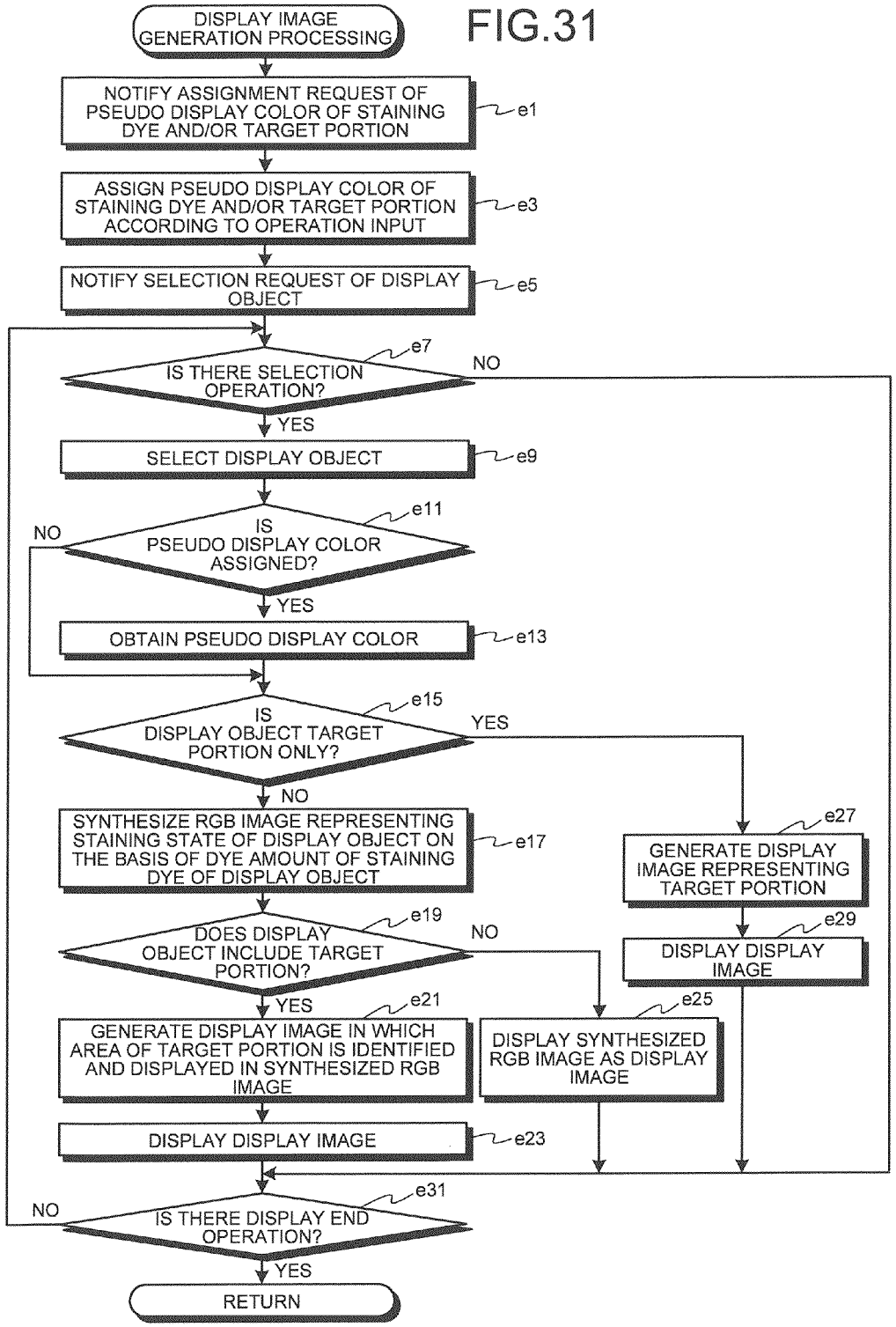
FIG. 31 is a flowchart showing a processing procedure of display image generation processing.

When the target portion map is created in the manner described above, as shown in FIG. 15, the process proceeds to display image generation processing (step b15). FIG. 31 is a flowchart showing a processing procedure of the display image generation processing.

In the display image generation processing, first, the pseudo display color assignment unit 463 performs processing for displaying a notification of an assignment request of a pseudo display color to be assigned to the molecule target dye included in the staining dye (step e1). For example, the pseudo display color assignment unit 463 shows a list of prepared pseudo display colors and receives a selection operation of a pseudo display color to be assigned to the molecule target dye included in the staining dye. When a plurality of molecule target dyes are included in the staining dye, the pseudo display color assignment unit 463 individually receives a selection operation of a pseudo display color to be assigned to each molecule target dye. The pseudo display color assignment unit 463 assigns the pseudo display color to the molecule target dye included in the staining dye in accordance with an operation input by a user responding to the notification of the assignment request (step e3).

Next, the display object selection processing unit 461 performs processing for displaying a notification of a selection request of a staining dye and/or a target portion to be displayed on the display unit 43 (step e5). The user responds to the notification of the selection request and selects one or more of staining dyes and target portions to be displayed. If the selection operation responding to the notification of the selection request is not inputted (step e7: No), the process proceeds to step e31. On the other hand, if the selection operation of a staining dye and/or a target portion to be displayed is inputted (step e7: Yes), the display object selection processing unit 461 selects a display object in accordance with the operation input (step e9).

Next, when the staining dye selected as a display object in step e9 includes a molecule target dye and a pseudo display color is assigned to the molecule target dye (step e11: Yes), the display image generator 462 reads and obtains a spectrum of the corresponding pseudo display color from the pseudo display color data 475 (step e13), and thereafter the process proceeds to step e15. On the other hand, when the staining dye selected as a display object does not include a molecule target dye, and when the staining dye includes a molecule target dye but a pseudo display color is not assigned (step e11: No), the process proceeds to step e15.

In the next step e15, the display image generator 462 determines the display object selected in step e9. When at least one staining dye is selected as a display object and the display object is not only the target portion (step e15: No), the display image generator 462 synthesizes an RGB image of the VS image representing the staining state thereof on the basis of the dye amount of the staining dye selected as a display object (step e17). Specifically, the display image generator 462 calculates RGB values of each pixel on the basis of the dye amount of the staining dye to be displayed in each pixel, and synthesizes the RGB image.

At this time, when the staining dye to be displayed includes the molecule target dye to which the pseudo display color is assigned in step e3, the display image generator 462 calculates the RGB values using the spectrum of the pseudo display color obtained in step e13 as a reference dye spectrum of the molecule target dye. Specifically, when calculating the RGB values, the display image generator 462 performs spectral estimation by replacing the reference dye spectrum $k_n(\lambda)$ of the corresponding molecule target dye with the spectrum of the pseudo display color obtained in step e13, and calculates the RGB values on the basis of the estimation result.

Here, the processing for calculating the RGB values on the basis of the dye amount and synthesizing the RGB image can be realized by, for example, applying the publicly known technique described in Japanese Laid-open Patent Publication No. 2008-51654. Processing procedure will be briefly described. First, the dye amounts $d_1, d_2, \ldots, d_n$, which are set in the dye amount data 582 (calculated is step c9 in FIG. 16), are multiplied by selection coefficients $\alpha_1, \alpha_2, \ldots, \alpha_n$ respectively, the obtained values are substituted into Equation (2), and the following Equation (7) is obtained. The selection coefficient $\alpha_n$ which is multiplied to the staining dye to be displayed is set to 1, and the selection coefficient $\alpha_n$ which is multiplied to the staining dye not to be displayed is set to 0, so that a spectral transmission rate $t^*(x, \lambda)$ targeting only the dye amount of the staining dye to be displayed is obtained.

$$t^*(x,\lambda)=e^{-(k_1(\lambda)\cdot\alpha_1 d_1+k_2(\lambda)\cdot\alpha_2 d_2+\ldots+k_n(\lambda)\cdot\alpha_n d_n)} \quad (7)$$

With respect to a given point (pixel) x in a captured multi-band image, a relationship of the following Equation (8) based on a camera response system is established between a pixel value g (x, b) in band b and the spectral transmission rate $t^*(x, \lambda)$ of a corresponding point on a specimen.

$$g(x,b)=\int_\lambda f(b,\lambda)s(\lambda)e(\lambda)t(x,\lambda)d\lambda+n(b) \quad (8)$$

λ represents a wavelength, f(b, λ) represents a spectral transmission rate of bth filter, s(λ) represents a spectral sensitivity characteristic of camera, e(λ) represents a spectral radiation characteristic of illumination, and n(b) represents observation noise in band b. b is a serial number for identifying band, and here, b is an integer satisfying 1≤b≤6.

Therefore, by substituting Equation (7) into Equation (8) described above and obtaining a pixel value in accordance with the following Equation (9), it is possible to obtain a pixel value g*(x, b) of a display image displaying the dye amount of the staining dye to be displayed (a display image representing the staining state by the staining dye to be displayed). In this case, the pixel values can be calculated assuming that the observation noise n(b) is zero.

$$g^*(x,b) = \int_\lambda f(b,\lambda) s(\lambda) e(\lambda) t^*(x,\lambda) d\lambda \qquad (9)$$

Next, the display image generator 462 determines whether or not the display object selected in step e9 includes the target portion. When the display object includes the target portion (step e19: Yes), the display image generator 462 generates a display image of the VS image in which the area of the target portion is identified and displayed in the RGB image synthesized in step e17 (step e21). Specifically, the display image generator 462 generates a display image in which the area of the target portion in the synthesized RGB image is displayed with a predetermined display color on the basis of the target portion map created in step b13 in FIG. 15. Specifically, the display image generator 462 generates the display image by replacing the pixel values of the pixel position at which "1" is set in the target portion map with a predetermined display color. The display color representing the area of the target portion may be a predetermined fixed color, or may be a color that can be arbitrarily changed by a user operation. The VS image display processing unit 454 performs processing for displaying the display image generated in step e21 on the display unit 43 (step e23).

On the other hand, when the display object does not include the target portion (step e19: No), the VS image display processing unit 454 performs processing for displaying the RGB image synthesized in step e17 on the display unit 43 as a display image of the VS image (step e25).

When it is determined that the display object is only the target portion in step e15 (step e15: Yes), the display image generator 462 generates a display image of the VS image in which the area of the target portion is displayed on the basis of the target portion map created in step b13 in FIG. 15 (step e27). Specifically, the display image generator 462 generates a display image in which pixel positions at which "1" is set in the target portion map are represented by a predetermined display color. The VS image display processing unit 454 performs processing for displaying the display image generated in step e27 on the display unit 43 (step e29).

Thereafter, the process proceeds to step e31, and the VS image display processing unit 454 determines whether the VS image display processing ends or not. For example, the VS image display processing unit 454 receives a display end operation. If the display end operation is inputted (step e31: Yes), the processing ends, and the process returns to step b15 shown in FIG. 15, and then proceeds to step b17. On the other hand, if the display end operation is not inputted (step e31: No), the process returns to step e7.

In step b17, an extraction condition change instruction operation is monitored, and when the change instruction operation is inputted (step b17: Yes), the process returns to step b9. On the other hand, when the extraction condition change instruction operation is not inputted (step b17: No), it is determined whether the VS image display processing ends or not, and when it is determined that the VS image display processing ends (step b19: Yes), the processing ends. When it is determined that the VS image display processing does not end (step b19: No), the process returns to step b17.

Here, when a target portion is selected as a display object, pixel positions at which "1" is set in the target portion map are displayed with a predetermined display color. On the other hand, when "expression is present" is set as the expression state which is one of the extraction conditions, the area of the target portion may be displayed by displaying the staining state of the corresponding molecule target dye at the pixel positions.

For example, in the first embodiment, an example is described in which a portion where the EGFR receptor is expressed on the cell membrane, in other words, a portion where the DAB dye is expressed on the cell membrane is extracted as the target portion. In this case, when the target portion is selected as a display object, the area of the target portion may be displayed by generating a display image representing the staining state of the DAB dye at each pixel constituting the area of the target portion. Specifically, the RGB values may be calculated on the basis of the dye amount of the DAB dye with respect to pixels to which "1" is set in the target portion map. At this time, a fixed pseudo display color may be assigned to the target portion, or a pseudo display color may be assigned to the target portion in accordance with a user operation. The area of the target portion may be displayed with a pseudo display color by replacing the reference dye spectrum $kn(\lambda)$ of the DAB dye with the spectrum of the pseudo display color and calculating the RGB values.

As shown and described in FIG. 29, when the target portion maps are individually created for each cell component, and then these target portion maps are combined to create a combined target portion map, if the target portion is selected as the display object, it is possible to generate a display image by using a different display color for each source target portion map before being combined. For example, when the target portion is selected as the display object, among the pixels to which "1" is set in the target portion map of (c) of FIG. 29, the pixels generated from the target portion map of (a) of FIG. 29 and the pixels generated from the target portion map of (b) of FIG. 29 may be displayed with a display color different from each other to create a display image.

In the same way, as shown and described in FIG. 30, when the target portion maps are individually created for each extraction condition, and then these target portion maps are combined to create a combined target portion map, if the target portion is selected as the display object, it is possible to generate a display image by using a different display color for each source target portion map before being combined. For example, when the target portion is selected as the display object, among the pixels to which "1" is set in the target portion map of (c) of FIG. 30, the pixels generated from the target portion map of (a) of FIG. 30 and the pixels generated from the target portion map of (b) of FIG. 30 may be displayed with a display color different from each other to create a display image.

Figure 32:
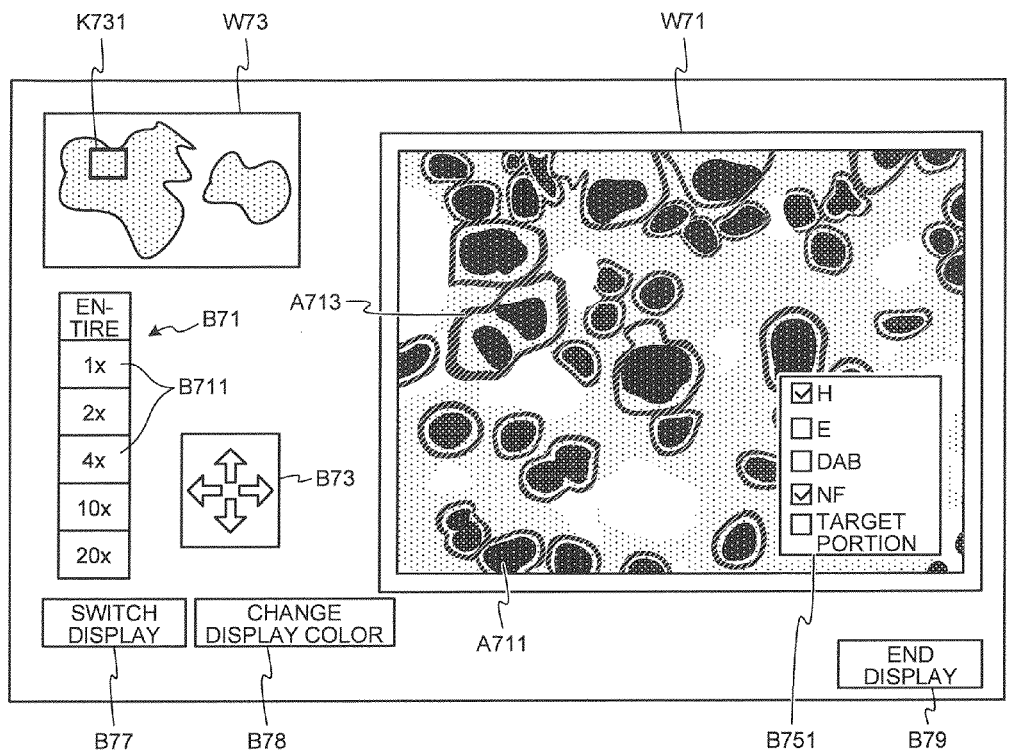
FIG. 32 is a diagram showing an example of a VS image observation screen.

Next, an operation example when displaying the display image on the display unit 43 and observing the VS image will be described. FIG. 32 is a diagram showing an example of a VS image observation screen. As shown in FIG. 32, the VS image observation screen includes a main screen W71, an entire specimen image navigation screen W73, a magnification selection unit B71, an observation range selection unit B73, a switch display button B77, a change display color button B78, and a end display button 379.

On the main screen W71, the display image is displayed which is generated to be displayed on the basis of the VS image obtained by combining specimen area segment images that are high resolution images. On the main screen W71, the user can observe the entire area of the target specimen S or each partial area of the target specimen S with high resolution in the same manner as that of the case where the target specimen S is actually observed using a high magnification objective lens in the microscope device 2.

When a mouse is right-clicked on the display image displayed on the main screen W71, a selection menu (hereinafter simply referred to as "display object selection menu") B751 of the staining dyes and/or the target portion as illustrated in FIG. 32 is displayed. In the display object selection menu B751, for example, the staining dyes and the target portion are displayed as options, and the staining dyes and/or the target portion checked in the display object selection menu B751 are selected as display objects. In the first embodiment, the staining dyes "H", "E", "DAB", and "NF", and "target portion" are displayed as five options, and when the display object is selected in the display object selection menu B751, the processing from step e9 to step e23 in FIG. 31 is performed. For example, as shown in FIG. 32, "H" and "NF" are checked. In this case, the display image generator 462 synthesizes an RGB image representing the staining state of the H dye and the NF dye on the basis of the dye amounts of the H dye and the NF dye in pixels in the current observation range of the VS image, and generates a display image in which the area of the target portion is identified and displayed on the synthesized RGB image. Then, the VS image display processing unit 454 displays the display image on the display unit 43 (specifically, on the main screen W71). This is the same when selecting "E", "DAB", and/or "target portion", or changing the combination of the display objects.

On the entire specimen image navigation screen W73, a reduced entire slide specimen image is displayed. On the entire slide specimen image, a cursor K731 is displayed which indicates an observation range that is a range of the display image currently displayed on the main screen W71. On the entire specimen image navigation screen W73, the user can understand easily which portion of the target specimen S is observed.

The magnification selection unit B71 selects a display magnification of the display image of the main screen W71. In the example illustrated in FIG. 32, magnification changing buttons B711 that are used to select display magnifications of "entire", "1×", "2×", "4×", "10×", and "20×" are disposed. In the magnification selection unit B71, for example, the magnification of the high magnification objective lens that is used to observe the target specimen S is provided as the maximum display magnification. When the user uses the mouse constituting the input unit 41 to click the desired magnification changing button B711, the display image displayed on the main screen W71 is expanded or reduced according to the selected display magnification and displayed.

The observation range selection unit B73 moves the observation range of the main screen W71. For example, when the user clicks arrows of the upper, lower, left, and right using the mouse, a display image where the observation range is moved in a desired movement direction is displayed on the main screen W71. For example, the observation range may be configured to be moved according to an operation of arrow keys included in a keyboard constituting the input unit 41 or a drag operation of the mouse on the main screen W71. The user can observe each portion of the target specimen S on the main screen W71 by operating the observation range selection unit B73 and moving the observation range of the main screen W71.

Figure 33:
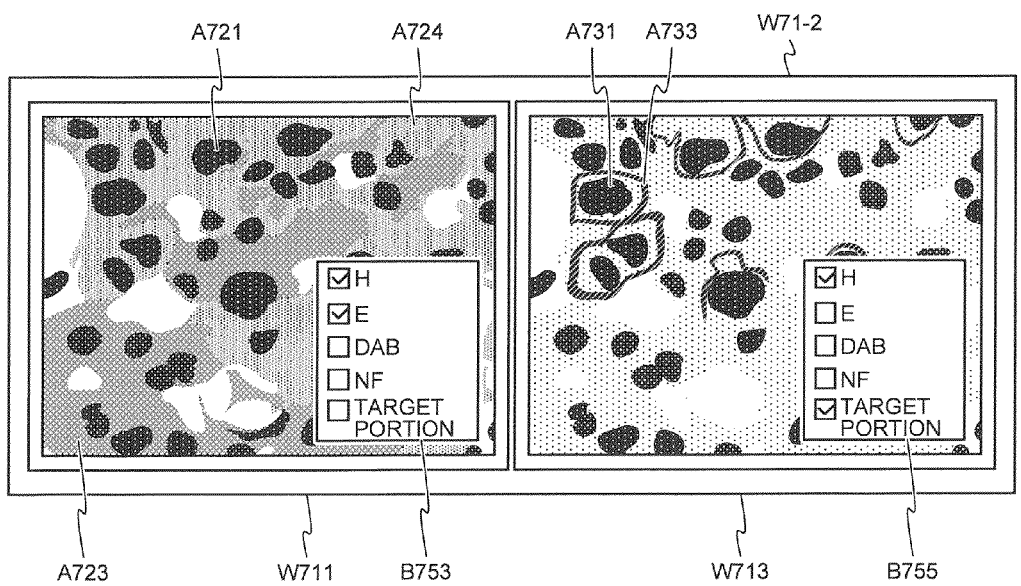
FIG. 33 is a diagram showing an example of a main screen that is switched by pressing a switch display button.

The switch display button B77 switches the display of the main screen W71. FIG. 33 is a diagram showing an example of a main screen W71-2 that is switched by pressing the switch display button B77. As shown in the main screen W71 of FIG. 32 and the main screen W71-2 of FIG. 33, if the switch display button B77 is pressed, a single mode where one display image is displayed on the main screen W71 and a multi mode where the main screen W71-2 is divided into two or more screens and a plurality of display images are displayed can be switched. In FIG. 33, the main screen W71-2 of two-screen configuration as the multi mode is illustrated. However, the main screen may be divided into three or more screens and three or more display images may be displayed.

In divided screens W711 and W713 of the main screen W71-2, the staining dye and/or the target portion to be displayed can be individually selected, and a display image where the dye amount thereof is displayed is displayed. Specifically, as illustrated in FIG. 33, if the user right-clicks the mouse on the divided screen W711, a display object selection menu B753 is displayed. In the display object selection menu B753, if the staining dye and/or the target portion to be displayed is checked, a display image where the dye amount of the desired dye is displayed or a display image where the target portion is displayed can be displayed. In the same way, if the user right-clicks the mouse on the divided screen W713, a display object selection menu B755 is displayed. In the display object selection menu B755, if the staining dye and/or the target portion to be displayed is checked, a display image where the dye amount of the desired dye is displayed or a display image where the target portion is displayed can be displayed.

For example, "H" and "E" are selected in the display object selection menu B753 on the divided screen W711 on the left side of FIG. 33. The display image of the divided screen W711 displays the staining states of the two dyes on the basis of the dye amounts of the staining dyes "H" and "E". On the other hand, "H" and "target portion" are selected in the display object selection menu B755 on the divided screen W713 on the right side of FIG. 33. The display image of the divided screen W713 displays the staining state of the "H" dye on the basis of the dye amount of the staining dye "H" and the area of the target portion that is identified and displayed. Since the "H" dye mainly stains the cell nucleus, the display image of the divided screen W713 represents the expression state of the target molecule as contrast staining of the cell nucleus. The display object selection menus B753 and B755 and the display object selection menu B753 shown in FIG. 32 are configured to disappear when the user left-clicks the mouse on the screen away from the display of the menus. The menus can be displayed when needed.

According to this configuration, for example, in the single mode, as shown in the main screen W71 of FIG. 32, a display image where the staining states of the staining dyes of H dye and NF dye are displayed can be observed. Here, in the main screen W71 of FIG. 32, for example, an area A711 represents the stating state of the H dye, and for example, an area A713 represents the stating state of the NF dye.

On the other hand, in the multi mode, as illustrated in the main screen W71-2 of FIG. 33, it is possible to juxtapose the display image which represents the staining states of the H dye and the E dye and the display image which represents the staining state of the H dye and identifies and displays the area of the target portion, and observe both screens while comparing both screens. More specifically, in the example of FIG. 33, it is possible to perform a conventional morphological observation performed by performing HE staining on the target specimen S (divided screen W711) and an observation of the target portion by the conventional IHC method in which contrast staining with H dye is performed on the target specimen S (divided screen W713) at the same time. Here, in the divided screen W711 of FIG. 33, for example, an area A721 represents the stating state of the H dye, and for example, areas A723 and A724 represent the stating state of the E dye. On the other hand, in the divided screen W713 of FIG. 33, for example, an area A731 represents the stating state of the H dye, and an area A733 represents the stating state of the target portion. In the first embodiment, as described above, "a portion where the EGFR receptor is expressed on the cell membrane in the target specimen" is defined as the target portion, and as shown in divided screen W71 of FIG. 33, the corresponding area (specifically, an area such as the area A733 where the EGFR receptor is expressed on the cell membrane) can be displayed with good visibility for the user.

When assigning a pseudo display color as the display color of a molecule target dye, the user presses the change display color button B78. Then, the user selects a desired molecule target dye and performs an operation to select a pseudo display color to be assigned to the selected molecule target dye from a displayed list of pseudo display colors. When ending the observation of the VS image, the user presses the end display button B79.

As described above, in the first embodiment, the target specimen S is observed and diagnosed on which staining is performed by the cell component identification dye that specifically stains at least a desired cell component and further staining is performed by the molecule target dye that visualizes a desired target molecule. By performing image processing on the specimen image obtained by capturing an image of the target specimen S, the area of the desired cell component present in the target specimen S can be identified. The area of the target portion can be extracted by using the presence or absence of the target molecule on the desired cell component as an extraction condition. It is possible to generate a display image of the VS image representing the area of the target portion. Base on this, it is possible to generate a display image on which the presence or absence of the expression of the target molecule on the desired cell component can be visually checked easily and display the display image on the display unit 43. Therefore, it is possible to properly identify the area of the desired cell component and the presence or absence of the expression of the desired target molecule on the cell component can be displayed with good visibility.

More specifically, when performing observation, the single mode and the multi mode are arbitrarily switched to display the VS image observation screens shown in FIGS. 32 and 33, and desired staining dyes and/or target portion are freely checked in the display object selection menu B751, B753, or B755, so that it is possible to arbitrarily combine the staining states of the staining dyes and/or the target portion to display them, or juxtapose display images having different display objects. Therefore, the observation of the expression state of the target molecule can be efficiently preformed with good visibility in combination with the morphology observation, so that diagnosis efficiency can be improved. A user such as a medical doctor can actively use the observation/diagnosis result for selecting medical treatment and predicting prognosis.

A pseudo display color can be arbitrarily assigned to the molecule target dye. As the reference dye spectrum of the molecule target dye, a spectrum different from the original spectrum (here, spectral transmittance characteristic) of the dye can be used. For example, for the staining state of the morphological observation dye, the same color as that of the dye which actually stains the specimen can be reproduced to display the staining state of the morphological observation dye, and for the staining state of the molecule target dye, for example, a pseudo display color that improves contrast against the morphological observation dye can be used to display the staining state of the molecule target dye. Based on this, for example, the staining state of the molecule target dye can be displayed in high contrast. Therefore, even when the morphology observation dye and the molecule target dye, or different types of molecule target dyes are visualized by using similar colors, these dyes can be displayed so that the dyes can be easily identified, and thus visibility can be improved when performing observation.

In a second embodiment, a cell is recognized on the basis of an identification result of a cell component, and normality/abnormality thereof is determined. In the description below, it is assumed that cell component identification staining for identifying three cell components, which are cell nucleus, cell membrane, and cytoplasm, is performed on the target specimen S, and the three components are identified.

Figure 34:
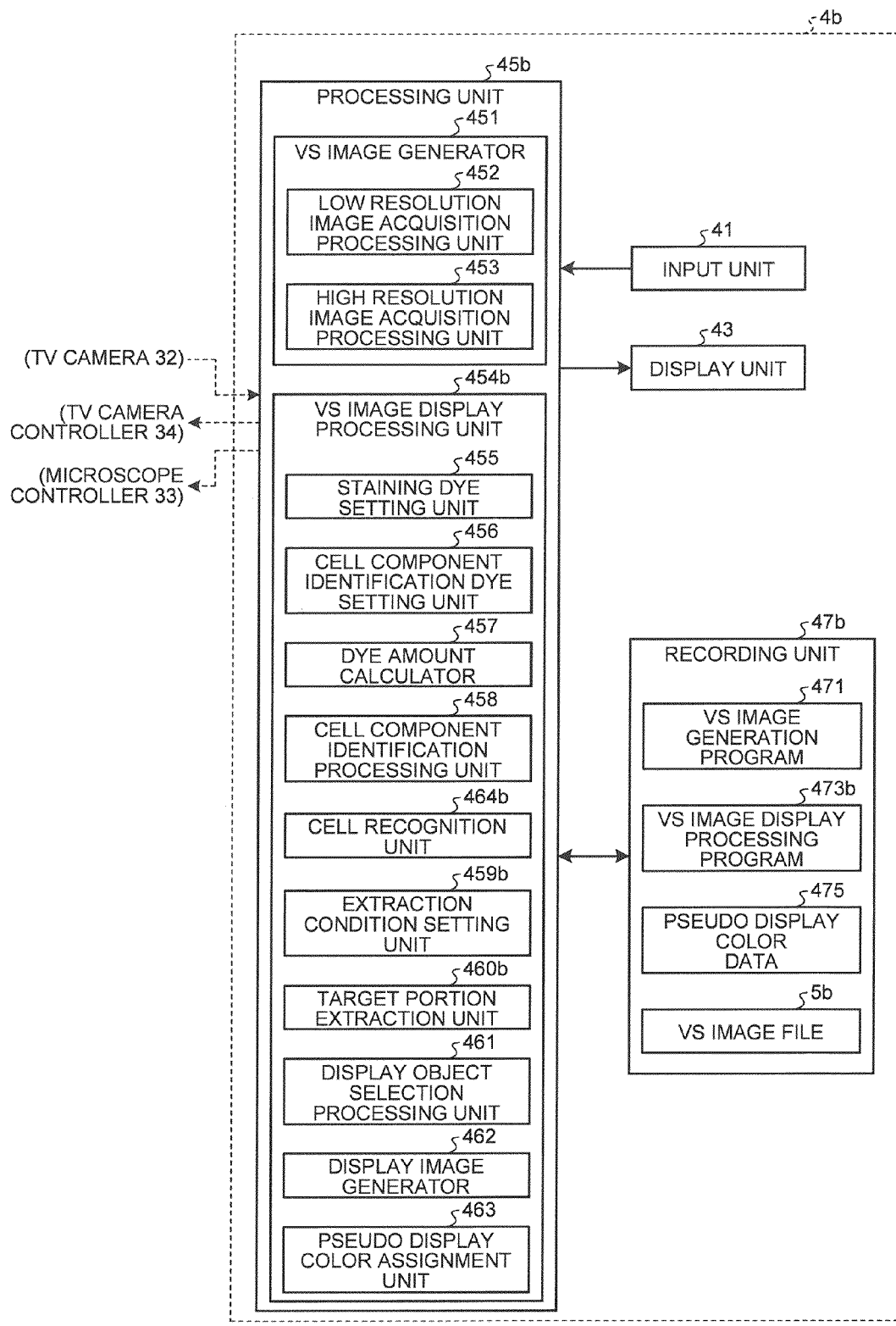
FIG. 34 is a diagram showing main functional blocks of a host system according to a second embodiment.

FIG. 34 is a diagram showing main functional blocks of a host system 4b according to the second embodiment. The same reference numerals are given to the same components as those described in the first embodiment. As shown in FIG. 34, the host system 4b included in a microscope system according to the second embodiment includes the input unit 41, the display unit 43, a processing unit 45b, a recording unit 47b, and the like.

A VS image display processing unit 454b in the processing unit 45b includes a staining dye setting unit 455, a cell component identification dye setting unit 456, a dye amount calculator 457, a cell component identification processing unit 458, a cell recognition unit 464b as a cell area recognition unit, a characteristic amount calculator, and an abnormality degree determination unit, an extraction condition setting unit 459b, a target portion extraction unit 460b, a display object selection processing unit 461, a display image generator 462, and a pseudo display color assignment unit 463. On the other hand, in the recording unit 47b, a VS image generation program 471, a VS image display processing program 473b, pseudo display color data 475, and a VS image file 5b are recorded.

Figure 35:
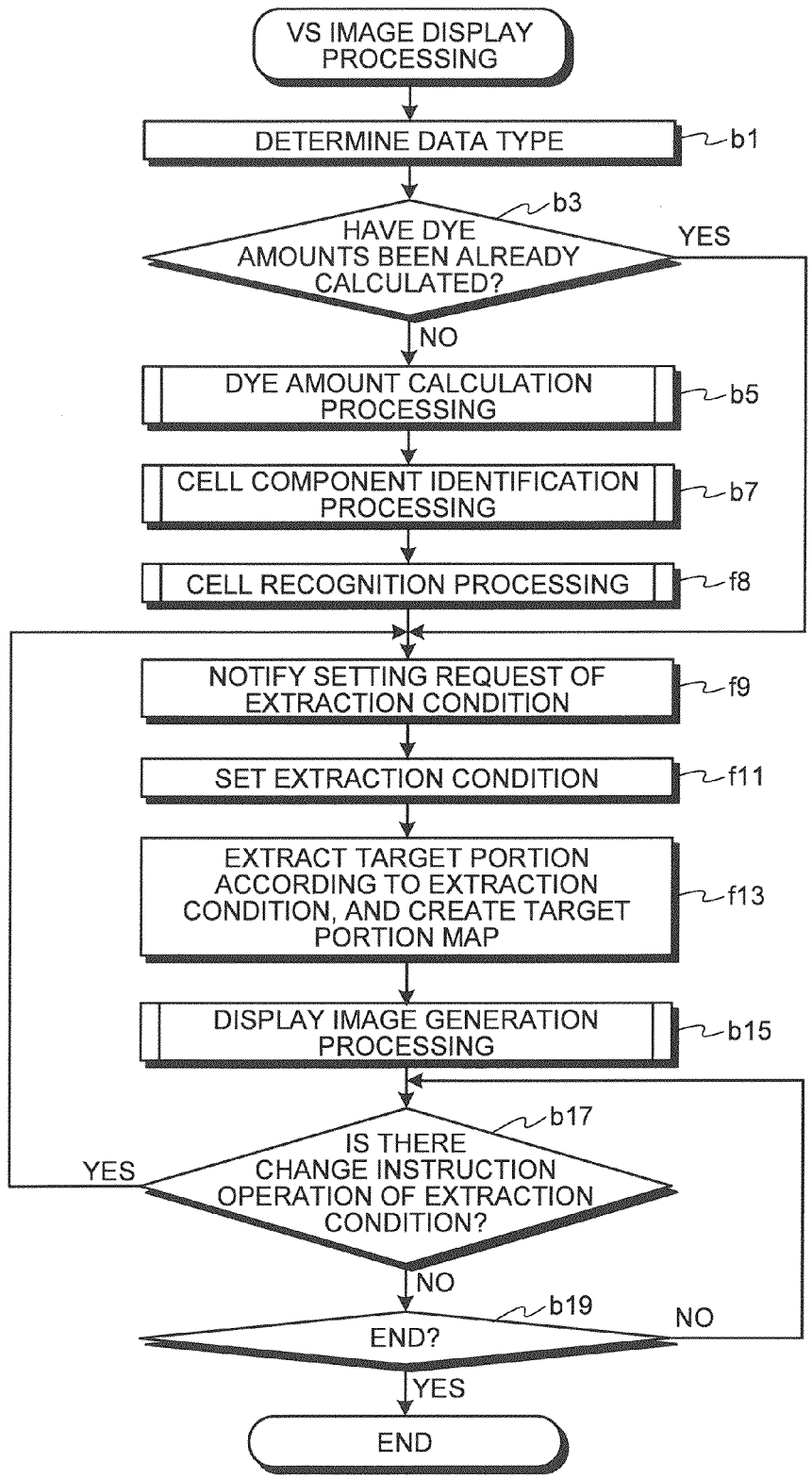
FIG. 35 is a flowchart showing a processing procedure of VS image display processing according to the second embodiment.

Next, the VS image display processing according to the second embodiment will be described. FIG. 35 is a flowchart showing a processing procedure of the VS image display processing according to the second embodiment. In FIG. 35, the same processing steps as those in the first embodiment are given the same reference symbols. The processing described here is realized by the VS image display processing unit 454b reading and executing the VS image display processing program 473b recorded in the recording unit 47b.

Figure 36:
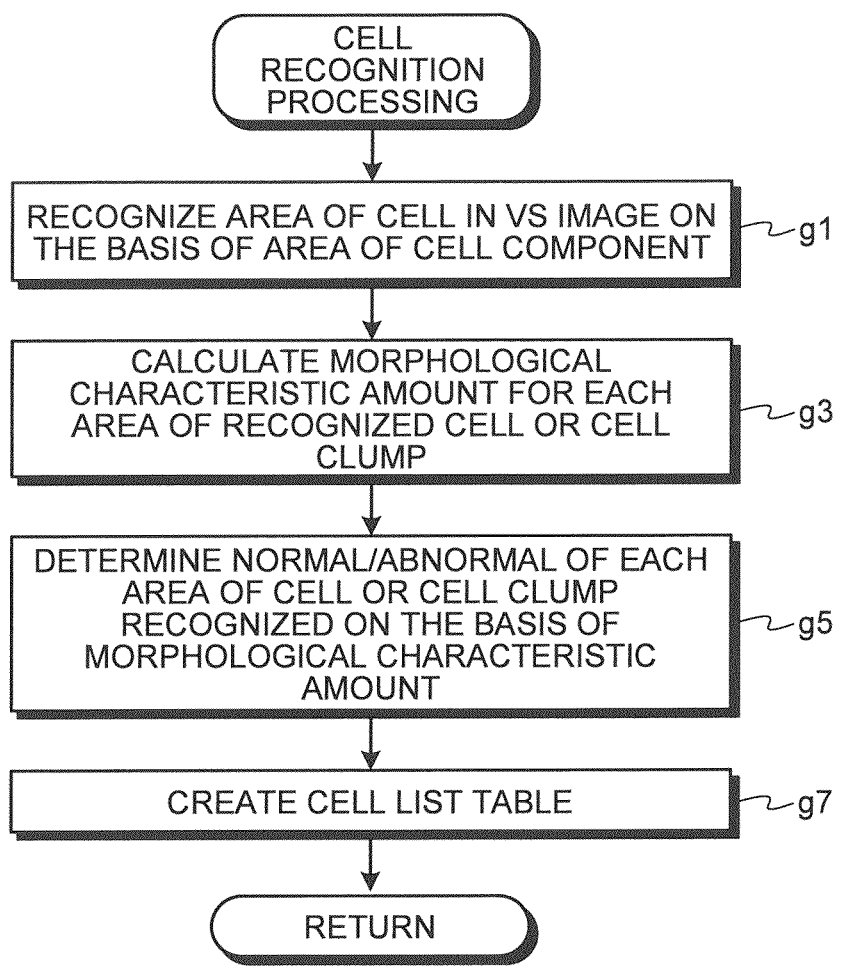
FIG. 36 is a flowchart showing a processing procedure of cell recognition processing.

As shown in FIG. 35, in the VS image display processing according to the second embodiment, after the cell component identification processing in step b7, the process proceeds to cell recognition processing (step f8). FIG. 36 is a flowchart showing a processing procedure of the cell recognition processing.

As shown in FIG. 36, in the cell recognition processing, first, the cell recognition unit 464b recognizes the area of the cell in the VS image (step g1) on the basis of the area of the cell component identified by the cell component identification processing unit 458 in step b7 of FIG. 35.

Figure 37:
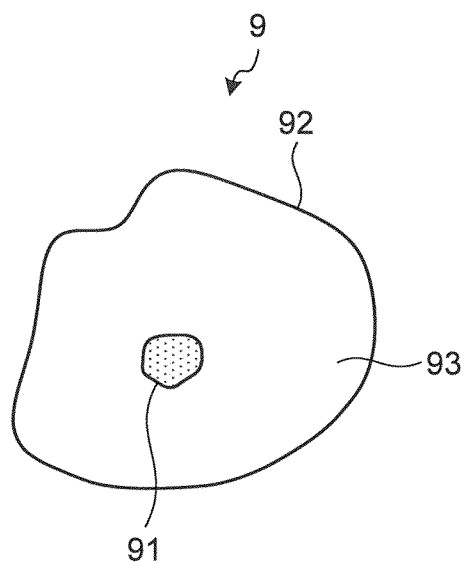
FIG. 37 is a schematic diagram for explaining a configuration of a cell.
Figure 38:
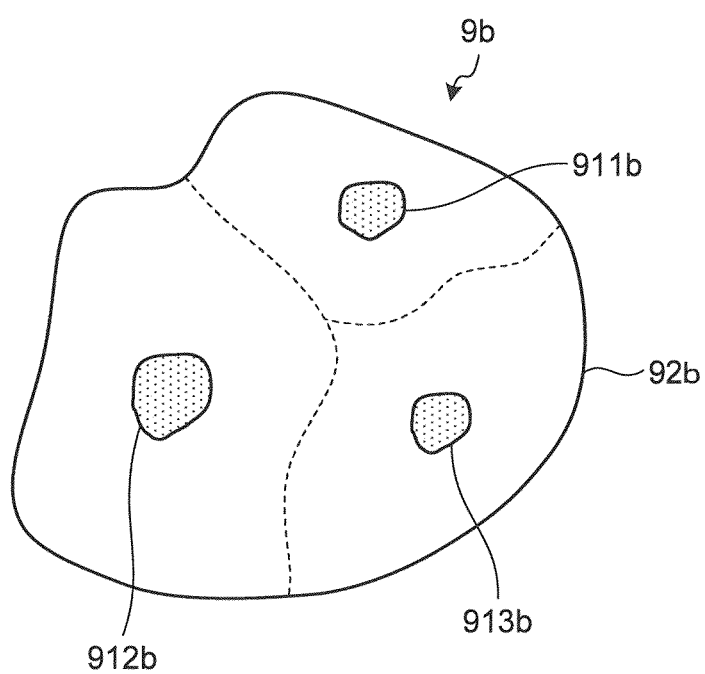
FIG. 38 is a schematic diagram for explaining another configuration of a cell.

Here, a configuration of the cell will be described. FIGS. 37 and 38 are schematic diagrams for explaining a configuration of the cell. As shown in FIG. 37, a cell 9 includes a cytoplasm 93 inside a cell membrane 92 that forms an outermost layer. Normally, there is one cell nucleus 91 inside the cell membrane 92. On the other hand, as shown in FIG. 38, there is a case in which a plurality of cells are fused together, so that part of cell membrane disappears as shown by dashed lines in FIG. 38, and thus a cell clump 9b enclosed by one cell membrane 92b is formed. The target specimen S includes such a cell clump 9b. In the example shown in FIG. 38, there are three cell nuclei 911b, 912b, and 913b inside one cell membrane 92b. In the second embodiment, an area enclosed by a cell membrane is recognized as an area of a cell or a cell clump. In other words, a cell membrane, and a cell nucleus (cell nuclei) and a cytoplasm that are located inside the cell membrane are recognized as one cell or one cell clump. If the number of the cell nuclei is one, they are recognized as a cell, and if the number is two or more, they are recognized as a cell clump.

Specifically, an area of one cell or one cell clump is recognized on the basis of the map data 594, the morphological characteristic data 595, and an identification component list 596 which are created with respect to cell nuclei, cell membranes, and cytoplasms (refer to FIGS. 24 and 25), and a unique label is attached to each area for identifying individual cells and cell clumps. At this time, the number of cell nuclei in an area recognized as one cell or one cell clump is counted.

Next, as shown in FIG. 36, the cell recognition unit 464b calculates morphological characteristic amounts showing morphological characteristics for each area of recognized cells or cell clumps (step g3). As the morphological characteristic amounts of a cell or a cell clump, there are the circumscribed rectangle, the center of gravity, the area, the boundary length, the degree of circularity, the long axis, the short axis, the aspect ratio, the number of nuclei, the area of nucleus, the dispersion of the areas of nuclei, the average dye amount of nucleus, the N/C ratio, the average dye amount of cytoplasm, and so forth. Here, the values of the circumscribed rectangle, the center of gravity, the area, the boundary length, the degree of circularity, the long axis, the short axis, and the aspect ratio can be calculated by the same calculation method as the calculation method of the morphological characteristic amounts of cell nucleus described in the first embodiment, and these values are calculated on the basis of the contour of the area of the recognized cell or cell clump. The contour of the area of the cell or the cell clump can be determined by pixels forming the boundary of the area. If the area of the cell or the cell clump is completely enclosed by the cell membrane, the outer contour of the cell membrane may be defined as the contour of the cell or the cell clump.

The number of nuclei is the number of areas of cell nuclei present inside the area of the cell or the cell clump. The average dye amount of nucleus is calculated as the average value of dye amounts of the cell nucleus identification dye (for example, H dye) of each pixel constituting the area of the cell nucleus present inside the area of the cell or the cell clump. The area of nucleus is calculated as the average value of each area of cell nucleus when a plurality of areas of cell nuclei are present inside the area of the cell or the cell clump. The dispersion of the areas of nuclei is calculated as the dispersion value of each area of cell nucleus when a plurality of areas of cell nuclei are present inside the area of the cell or the cell clump.

The N/C ratio is calculated according to, for example, the following Equation (10) on the basis of the areas of the cell nuclei and the cell membrane inside the area of the cell or the cell clump.

$$N/C \text{ ratio} = \text{total area of cell nuclei/total area of cytoplasm} \quad (10)$$

The average dye amount of cytoplasm is calculated as the average value of dye amounts of the cytoplasm identification dye (for example, E dye) of each pixel constituting the area of the cytoplasm present inside the area of the cell or the cell clump.

Next, the cell recognition unit 464b performs determination of normality/abnormality of each of the areas of the recognized cells and cell clumps (step g5). This determination of normality/abnormality can be realized by, for example, applying a publicly known technique described in Japanese Laid-open Patent Publication No. 2009-175334.

Processing procedure will be briefly described. The cell recognition unit 464b performs processing described below in which the areas of the recognized cell and cell clumps are sequentially processed. First, the cell recognition unit 464b defines a predetermined morphological characteristic amount among the morphological characteristic amounts calculated in step g3 as an abnormal level identification item, and identifies an abnormal level on the basis of the value of the morphological characteristic amount. Which morphological characteristic amount is defined as the abnormal level identification item is arbitrarily selected. The number of the morphological characteristic amounts defined as an abnormal level identification item may be one or more than one. However, an abnormal level identification table in which a correspondence relationship between the values of the morphological characteristic amounts and the abnormal levels is set for each morphological characteristic amount defined as an abnormal level identification item is prepared in advance and stored in the recording unit 47b. The abnormal level is identified on the basis of the value of the morphological characteristic amounts calculated in step g3 by referring to the abnormal level identification table.

In the second embodiment, for example, different abnormal level identification tables are prepared for cell areas and call clump areas respectively. Specifically, four abnormal level identification items, which are the N/C ratio, the average dye amount of nucleus, the area of nucleus, and the degree of circularity, are defined for cell, and an abnormal level identification table in which a correspondence relationship between the values of the morphological characteristic amounts of the four items and abnormal levels is set is prepared. On the other hand, for cell clump, four abnormal level identification items, which are the N/C ratio, the average dye amount of nuclei, the area of nuclei, and the dispersion of the areas of nuclei, are defined, and an abnormal level identification table in which a correspondence relationship between the values of the morphological characteristic amounts of the four items and abnormal levels is set is prepared. For example, the highest abnormal level is defined as level 4, and 4 levels of abnormal levels are identified by each abnormal level identification table.

For a cell area, the abnormal level is calculated using the abnormal level identification table for cell. On the other hand, for a cell clump area, the abnormal level is calculated using the abnormal level identification table for cell clump. Whether an area is a cell area or a cell clump area can be determined by the number of the cell nuclei in the area.

Thereafter, the cell recognition unit 464b determines a score of the cell or the cell clump on the basis of the abnormal level identified with respect to the predetermined morphological characteristic amounts as described above. To determine the score, a score determination table is used. FIG. 39 is a diagram showing an example of the score determination table applied to a cell area, and FIG. 40 is a diagram showing an example of the score determination table applied to a cell clump area. These score determination tables are tables in which a determination result ("normal" or "abnormal") and a score are associated with each other for each combination of the abnormal levels of the abnormal level identification items. The score determination tables are prepared in advance and stored in the recording unit 47b. For example, values of 10 levels from "1" to "10" are defined as scores. The smallest value (smallest abnormality) is defined as "1" and the greatest value (greatest abnormality) is defined as "10".

Specifically, in FIG. 39, the score determination table for cell is illustrated in which a combination of the abnormal levels of the four abnormal level identification items, the N/C ratio, the average dye amount of nucleus, the area of nucleus, and the degree of circularity, is associated with the determination result thereof for each combination. On the other hand, in FIG. 40, the score determination table for cell clump is illustrated in which a combination of the abnormal levels of the four abnormal level identification items, the N/C ratio, the average dye amount of nuclei, the area of nuclei, and the dispersion of the areas of nuclei, is associated with the determination result thereof for each combination.

When determining a score of a cell, the score is determined by obtaining a corresponding classification and a score from the score determination table shown in FIG. 39 on the basis of the combination of the abnormal levels of the N/C ratio, the average dye amount of nucleus, the area of nucleus, and the degree of circularity which are identified for the area of the cell. When determining a score of a cell clump, the score is determined by obtaining a corresponding classification and a score from the score determination table shown in FIG. 40 on the basis of the combination of the abnormal levels of the N/C ratio, the average dye amount of nuclei, the area of nuclei, and the dispersion of the areas of nuclei which are identified for the area of the cell clump.

When the score is determined, as shown in FIG. 36, the cell recognition unit 464b associates the morphological characteristic amounts calculated in step g3 with the classification and the score obtained in the process of the processing of step g5, and creates a cell list table (step g7). FIGS. 41A and 41B are diagrams for explaining a data configuration example of the cell list table. As shown in FIG. 41A, the cell list table is configured by associating the morphological characteristic amounts of the circumscribed rectangle, the center of gravity, the area, the boundary length, the degree of circularity, the long axis, the short axis, and the aspect ratio calculated in step g3 of FIG. 36 with the label attached to the cell or the cell clump and the labels attached to the cell nucleus, the cell membrane, and the cytoplasm constituting the cell or the cell clump by the cell component identification processing in step b7 of FIG. 35. Further, in addition to the cell list table shown in FIG. 41A, as shown in FIG. 41B, the cell list table is configured by associating the morphological characteristic amounts of the number of nuclei, the area of nucleus, the dispersion of the areas of nuclei, the average dye amount of nuclei, the N/C ratio, and the average dye amount of cytoplasm, and the classification and the score obtained in the process of the processing of step g5 in FIG. 36 with the label attached to the cell or the cell clump and the labels attached to the cell nucleus, the cell membrane, and the cytoplasm constituting the cell or the cell clump by the cell component identification processing in step b7 of FIG. 35.

The cell list table is stored, for example, in the VS image information 55 shown in (a) of FIG. 14. Therefore, the VS image file 5b has a data configuration different from that of the VS image file 5 of the first embodiment. Specifically, the VS image information 55 of the VS image file 5b stores the cell list table created here in addition to the imaging information 56, the focus map data 57, the image data 58, and the identification component information 59 shown in (b) of FIG. 14.

When the cell list table is created as described above, the cell recognition processing ends. Then, the process returns to step f8 in FIG. 35, and thereafter the process proceeds to step f9. In the next step b9, in the same manner as in the first embodiment, the extraction condition setting unit 459b performs processing for displaying a notification of a setting request of an extraction condition for extracting the target portion on the display unit 43. Then, in the same manner as in the first embodiment, the extraction condition setting unit 459b sets the extraction condition on the basis of the information manually inputted by the user (step f11). Thereafter, in the same manner as in the first embodiment, the target portion extraction unit 460b performs processing to extract the target portion (target portion extraction processing) according to the extraction condition set in step b11, and creates a target portion map (step f13).

In the second embodiment, cell areas in the VS image are recognized and a score is determined for each recognized area of the cells. Therefore, in the second embodiment, in addition to the extraction conditions described in the first embodiment, the classification of normality/abnormality and the score with respect to the cell or cell clump to which the set cell component belongs can be set as extraction conditions and the target portion can be extracted in accordance with the set extraction conditions. The processing of the above is performed from step f9 to step f13. Based on this, for example, it is possible to extract a portion where a desired target molecule is expressed on a desired cell component and the score of the cell including the cell component as a constituent element thereof is a desired score (for example, "10"). Or, it is possible to extract a portion where a desired target molecule is not expressed on a desired cell component and the classification of the cell including the cell component as a constituent element thereof is a desired classification (for example, "abnormal").

As described above, according to the second embodiment, it is possible to recognize an area of a cell in the VS image, in other words, an area of a cell present in the target specimen S, and determine whether the recognized area of the cell is normal or abnormal. Also, it is possible to extract the target portion considering the abnormality or the normality of the cell.

Also, it is possible to display only the cells determined to be abnormal and observe and diagnose the expression state of the target molecule by displaying the VS image observation screen shown in FIGS. 32 and 33 and checking the target portion on the display object selection menus B751, B753, and B755 when performing observation. Therefore, a user such as a medical doctor can easily understand molecular biological characteristics of the cell determined to be abnormal. The user can actively use the observation/diagnosis result for selecting medical treatment and predicting prognosis.

In the second embodiment, the case is described in which an area where a plurality of cell nuclei are present inside the cell membrane is recognized as a cell clump where a plurality of cells are fused together. However, there is a cell which includes a plurality of cell nuclei as constituent elements thereof. Therefore, an area where a plurality of cell nuclei are present inside the cell membrane as shown in FIG. 38 may be recognized as one cell.

When using the cell nucleus identification information 591, the cell membrane identification information 592, and cytoplasm identification information 593 (refer to FIGS. 24 and 25) described in the first embodiment and the target portion information 8 (refer to FIG. 28), it is possible to calculate the number of cells that include the target portion, in other words, the number of cells that include a positive cell component as a constituent element thereof (hereinafter referred to as "positive cell") and an amount of statistics such as the rate of the positive cells.

Figure 42:
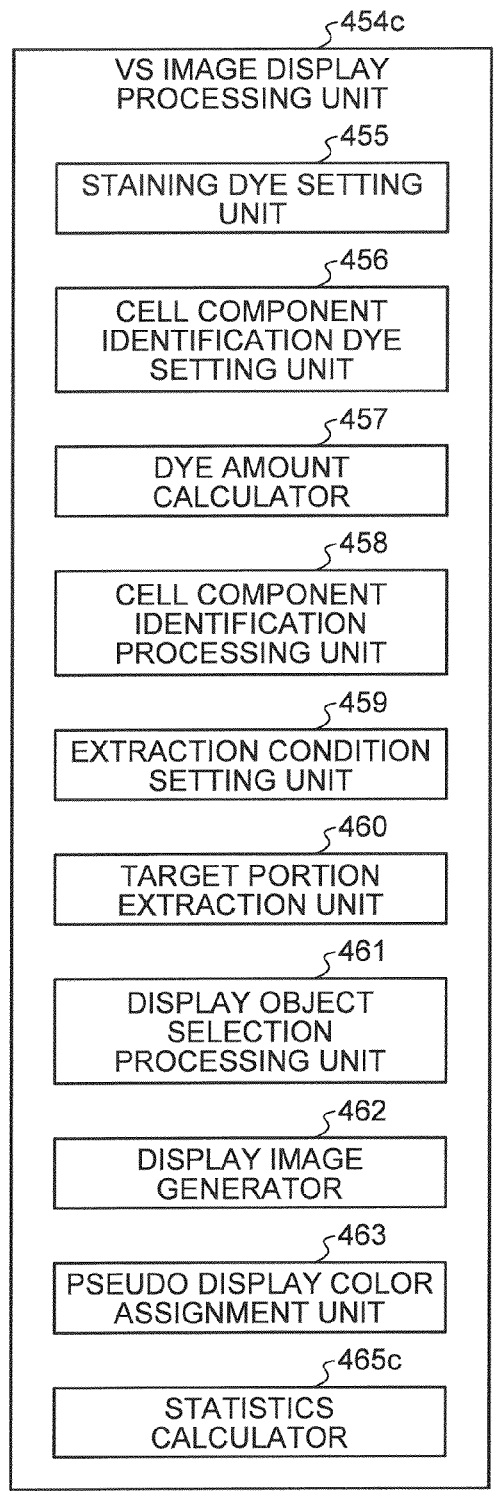
FIG. 42 is a diagram showing functional blocks of a VS image display processing unit according to a third embodiment.

FIG. 42 is a diagram showing functional blocks of a VS image display processing unit 454c included in a processing unit of a host system according to a third embodiment. The host system of the third embodiment can be realized by replacing the VS image display processing unit 454 in the processing unit 45 shown in FIG. 2 in the host system 4 of the first embodiment with the VS image display processing unit 454c shown in FIG. 42.

As shown in FIG. 42, the VS image display processing unit 454c according to the third embodiment includes the staining dye setting unit 455, the cell component identification dye setting unit 456, the dye amount calculator 457, the cell component identification processing unit 458, the extraction condition setting unit 459, the target portion extraction unit 460, the display object selection processing unit 461, the display image generator 462, the pseudo display color assignment unit 463, and a statistics calculator 465c. The statistics calculator 465c may not only be applied to the first embodiment, but also may be applied to the second embodiment, and in this case, the configuration can be realized by adding the statistics calculator 465c in the VS image display processing unit 454b in the processing unit 45b shown in FIG. 34.

The statistics calculator 465c counts the number of positive cells and calculates the rate of positive cells at a predetermined timing after the target portion extraction unit 460 extracts an area of the target portion.

Here, as shown and described in FIG. 37 in the second embodiment, regarding simple cells, the number of cells=the number of cell nuclei=the number of cell membranes. Therefore, the number of positive cells is the same as the number of positive cell components set in the number of positive cell components 84 (refer to (b) of FIG. 28), and calculated as the value of the number of positive cell components 84.

On the other hand, the rate of positive cells is calculated according to the following equation (11). As described above, since the number of cells=the number of cell nuclei=the number of cell membranes, the number of cells appearing in the VS image, in other words, the number of cells in the target specimen S (the total number of cells) is either one of the number of cell nuclei and the number of cell membranes (the number of identification components 597 shown in (a) of FIG. 25).

The rate of positive cells (%)=(the number of positive cells/the total number of cells)×100     (11)

However, in the target specimen S, there are cell clumps 9b shown and described in FIG. 38 in the second embodiment. Therefore, when handling such a cell clump as a group of a plurality of cells as described in the second embodiment, the rate of positive cells is calculated using the number of cell nuclei as the total number of cells.

The statistics of the number of positive cells and the rate of positive cells counted and calculated as described above are displayed on the display unit 43 at a given timing such as, for example, when the user inputs a display instruction operation of the statistics.

As described above, there are cells which includes a plurality of cell nuclei as constituent elements thereof. Therefore, there is a case in which an area where a plurality of cell nuclei are present inside the cell membrane as shown in FIG. 38 is desired not to be handled as a cell clump where a plurality of cells are fused together, but to be handled as one cell. Considering such a case, when an area where a plurality of cell nuclei are present inside the cell membrane as shown in FIG. 38 is desired to be handled as one cell, the number of cell membranes may be used as the total number of cells. Whether the number of cell nuclei is used as the total number of cells or the number of cytoplasms is used as the total number of cells may be configured to be able to be set, for example, according to a user operation.

As described above, according to the third embodiment, it is possible to calculate statistics such as the number of positive cells and the rate of positive cells on the basis of the areas of identified cell components and the areas of extracted cell components. The calculated statistics can be displayed on the display unit 43 and shown to a user. Therefore, a user such as a medical doctor can actively use the values of the statistics for selecting medical treatment and predicting prognosis.

Although, in the description of the third embodiment, the number of positive cells and the rate of positive cells are calculated with respect to the entire area of the VS image, in actual diagnosis of cancer, it is generally performed that the number of positive cells and the rate of positive cells in a tumor area are calculated and used. Therefore, in the main screen W71 in the VS image observation screen shown in FIG. 32, an area selection operation may be accepted. The number of positive cells and the rate of positive cells present in the area selected by the user on the main screen W71 may be calculated.

According to the microscope system, the specimen observation method, and the computer program product of the present invention, it is possible to obtain the dye amounts of the element identification dye and the molecule target dye that stain corresponding positions on a specimen for each pixel in a specimen image, and identify an area of a predetermined cell constituent element in the specimen image on the basis of the obtained dye amount of the element identification dye. In addition, it is possible to extract an area of the target portion by using the presence or absence of a predetermined target molecule at least on the predetermined cell constituent element as an extraction condition, and generate a display image representing the extracted area of the target portion. Therefore, it is possible to properly identify an area of a desired cell constituent element and the presence or absence of the expression of a desired target molecule on the cell constituent element can be displayed with good visibility.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A microscope system comprising:
an image acquisition unit that obtains, using a microscope, a specimen image acquired by capturing an image of the specimen stained by a plurality of cell element identification dyes that identifies two or more predetermined cell constituent elements based upon stain intensities produced by an interaction of the cell element identification dyes and the predetermined cell constituent elements, and a molecule target dye that identifies a predetermined target molecule based upon a stain intensity produced by an interaction of the molecule target dye and the predetermined target molecule;
a stain intensity obtaining unit that obtains stain intensities of the cell element identification dyes and the molecule target dye that stain corresponding positions on the specimen for each pixel of the acquired specimen image;
an element area identification unit that identifies areas of the two or more predetermined cell constituent elements within the specimen image on the basis of the obtained stain intensities of the cell element identification dyes;

a cell area recognition unit for recognizing an area of a cell determined by at least one of the areas of the two or more cell constituent elements;

a characteristic amount calculator that calculates a morphological characteristic amount of the cell;

an extraction condition setting unit that sets the presence or absence of the predetermined target molecule on the basis of the morphological characteristic amount of the cell and the obtained stain intensity of the molecule target dye, at least within the plurality of the identified area of the predetermined cell constituent elements as an extraction condition;

a target portion extraction unit that extracts an area of a target portion that satisfies the set extraction condition on the basis of identifying within at least one of the identified areas of the predetermined cell constituent element of the specimen image pixels that represent the presence of the stain intensities of the molecule target dye, if any, and considering the calculated morphological characteristic amount of the cell to which at least one of the two predetermined cell constituent elements belongs;

a display image generator that generates a display image representing the area of the target portion; and a display processing unit that performs processing for displaying the display image on a display unit.

2. The microscope system according to claim 1, wherein the extraction condition setting unit further sets a presence density of the predetermined target molecule within at least one of the identified areas of the predetermined cell constituent elements as the extraction condition, and the target portion extraction unit extracts the area of the target portion based on the obtained stain intensity of the molecule target dye.

3. The microscope system according to claim 1, wherein the extraction condition setting unit further sets a presence rate of the predetermined target molecule within at least one of the identified area of the predetermined cell constituent elements as the extraction condition, and the target portion extraction unit extracts the area of the target portion based on the number of pixels that include the molecule target dye within at least one of the identified area of the predetermined cell constituent elements.

4. The microscope system according to claim 1, wherein the specimen is stained by a plurality of molecule target dyes that identify two or more target molecules, and the extraction condition setting unit sets the presence or absence of each of a plurality of target molecules within at least one of the identified area of the predetermined cell constituent elements as the extraction condition.

5. The microscope system according to claim 1, further comprising an abnormality degree determination unit for determining an abnormality degree of the cell on the basis of the morphological characteristic amount calculated by the characteristic amount calculator, wherein the extraction condition setting unit further sets an abnormality degree of a cell as the extraction condition, and the target portion extraction unit extracts the area of the target portion considering an abnormality degree of a cell to which at least one of the predetermined cell constituent elements belongs.

6. The microscope system according to claim 1, further comprising a statistics calculator for calculating at least one of the number of the predetermined cell constituent elements that include the area of the target portion extracted by the target portion extraction unit and a rate of the number of the predetermined cell constituent elements that include the area of the target portion to the total number of the identified predetermined cell constituent elements present in the specimen.

7. The microscope system according to claim 1, wherein the at least one of the predetermined cell constituent elements is a cell membrane, a cell nucleus, or a cytoplasm.

8. The microscope system according to claim 1, wherein the image acquisition unit acquires a plurality of specimen images by capturing images of portions of the specimen while relatively moving the specimen and an objective lens in a plane perpendicular to an optical axis of the objective lens, and The microscope system further includes a specimen image generator for generating a single specimen image by combining the plurality of specimen images.

9. A specimen observation method comprising:

obtaining, using a microscope, a specimen image acquired by capturing an image of the specimen stained by a plurality of cell element identification dyes that identifies two or more predetermined cell constituent elements based upon stain intensities produced by an interaction of the cell element identification dyes and the predetermined cell constituent elements, and a molecule target dye that identifies a predetermined target molecule based upon a stain intensity produced by an interaction of the molecule target dye and the predetermined target molecule;

obtaining stain intensities of the cell element identification dyes and the molecule target dye that stain corresponding positions on the specimen for each pixel of the specimen image;

identifying area of the predetermined cell constituent elements in the specimen image on the basis of the obtained stain intensities of the cell element identification dyes;

recognizing an area of a cell determined by at least one of the areas of the two or more cell constituent elements;

calculating a morphological characteristic amount of the cell;

setting the presence or absence of the predetermined target molecule on the basis of the morphological characteristic amount of the cell and the obtained stain intensity of the molecule target dye, at least within the plurality of the identified areas of the predetermined cell constituent elements as an extraction condition;

extracting an area of a target portion that satisfies the extraction condition on the basis of identifying within the at least one identified area of the predetermined cell constituent elements of the specimen image pixels that represent the presence of the stain intensities of the molecule target dye, if any, and considering the calculated morphological characteristic amount of the cell to which at least one of the two predetermined cell constituent elements belongs;

generating a display image representing the area of the target portion; and displaying the display image.

10. A computer program product having a non-transitory computer readable medium including programmed instructions, wherein the instructions, when executed by a computer, cause the computer to perform:

obtaining, using an operation instruction to a microscope, a specimen image acquired by capturing an image of the specimen stained by a plurality of cell element identification dyes that identifies two or more predetermined cell constituent elements based upon stain intensities produced by an interaction of the cell element identification dyes and the predetermined cell constituent elements, and a molecule target dye that identifies a predetermined target molecule based upon a stain intensity produced by an interaction of the molecule target dye and the predetermined target molecule;

obtaining stain intensities of the cell element identification dyes and the molecule target dye that stain corresponding positions on the specimen for each pixel of the specimen image;

identifying areas of the predetermined cell constituent elements in the specimen image on the basis of the obtained stain intensities of the cell element identification dyes;

recognizing an area of a cell determined by at least one of the areas of the two or more cell constituent elements;

calculating a morphological characteristic amount of the cell;

setting the presence or absence of the predetermined target molecule on the basis of the morphological characteristic amount of the cell and the obtained stain intensity of the molecule target dye, at least within the plurality of the identified areas of the predetermined cell constituent elements as an extraction condition;

extracting an area of a target portion that satisfies the extraction condition on the basis of identifying within the at least one identified areas of the predetermined cell constituent elements of the specimen image pixels that represent the presence of the stain intensities of the molecule target dye, if any, and considering the calculated morphological characteristic amount of the cell to which at least one of the two predetermined cell constituent elements belongs;

generating a display image representing the area of the target portion; and displaying the display image.

* * * * *

UNITED STATES PATENT AND TRADEMARK OFFICE
CERTIFICATE OF CORRECTION

| | | |
|---|---|---|
| PATENT NO. | : 9,110,305 B2 | Page 1 of 1 |
| APPLICATION NO. | : 12/950268 | |
| DATED | : August 18, 2015 | |
| INVENTOR(S) | : Tatsuki Yamada et al. | |

It is certified that error appears in the above-identified patent and that said Letters Patent is hereby corrected as shown below:

On the title page item (73), should read:

--OLYMPUS CORPORATION, Tokyo (JP);
JAPANESE FOUNDATION FOR CANCER RESEARCH, Tokyo (JP)--

Signed and Sealed this
First Day of March, 2016

Michelle K. Lee
*Director of the United States Patent and Trademark Office*